United States Patent
Satake et al.

(10) Patent No.: US 9,377,445 B2
(45) Date of Patent: Jun. 28, 2016

(54) IONIZATION METHOD, IONIZATION APPARATUS, AND MASS ANALYSIS SYSTEM

(75) Inventors: Hiroyuki Satake, Tokyo (JP); Hideki Hasegawa, Tokyo (JP); Yuichiro Hashimoto, Tokyo (JP); Masao Suga, Tokyo (JP); Izumi Waki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/383,607

(22) PCT Filed: Aug. 27, 2012

(86) PCT No.: PCT/JP2012/071534
§ 371 (c)(1),
(2), (4) Date: Sep. 8, 2014

(87) PCT Pub. No.: WO2013/132676
PCT Pub. Date: Sep. 12, 2013

(65) Prior Publication Data
US 2015/0102232 A1    Apr. 16, 2015

(30) Foreign Application Priority Data

Mar. 9, 2012  (JP) .................................. 2012-052485

(51) Int. Cl.
*H01J 49/16*    (2006.01)
*H01J 49/04*    (2006.01)
*G01N 30/72*    (2006.01)
*G01N 27/62*    (2006.01)

(52) U.S. Cl.
CPC ............ *G01N 30/7266* (2013.01); *G01N 27/62* (2013.01); *H01J 49/0409* (2013.01); *H01J 49/0445* (2013.01); *H01J 49/165* (2013.01); *G01N 30/7233* (2013.01)

(58) Field of Classification Search
CPC . G01N 30/7266; G01N 35/085; H01J 49/165; H01J 49/0409; H01J 49/0445
See application file for complete search history.

(56) References Cited

U.S. PATENT DOCUMENTS

| | | | |
|---|---|---|---|
| 6,245,227 B1 | 6/2001 | Moon et al. | |
| 7,364,913 B2 | 4/2008 | Andrien, Jr. et al. | |
| 7,902,499 B2 | 3/2011 | Hiraoka et al. | |
| 2004/0166504 A1 | 8/2004 | Rossier et al. | |
| 2006/0145069 A1 | 7/2006 | Andrien, Jr. et al. | |
| 2008/0223455 A1* | 9/2008 | Fukuhara et al. | 137/488 |
| 2009/0140137 A1* | 6/2009 | Hiraoka et al. | 250/282 |
| 2009/0256072 A1* | 10/2009 | Reilly | 250/288 |
| 2010/0187092 A1* | 7/2010 | Weist et al. | 204/176 |

FOREIGN PATENT DOCUMENTS

| | | |
|---|---|---|
| JP | 2000-009693 A | 1/2000 |
| JP | 2005-501231 A | 1/2005 |
| JP | 2011-133245 A | 7/2011 |
| WO | 99/19899 A1 | 4/1999 |
| WO | 2007/126141 A1 | 11/2007 |

* cited by examiner

*Primary Examiner* — Robert Kim
*Assistant Examiner* — Sean Luck
(74) *Attorney, Agent, or Firm* — Mattingly & Malur, PC

(57) ABSTRACT

In order to achieve an ionization method of high robustness with a small carry-over or less crosstalk, an ionization method is disclosed. A method includes the steps of: joining an ionization unit to a tube; sucking the sample from a sample container into a sample holder of the ionization unit to hold the sample; moving the ionization unit holding the sample to near the ionization unit using an ionization unit drive unit; and applying a voltage to the ionization unit using a power supply to ionize the sample by electrostatically spraying the sample from the holding unit.

14 Claims, 45 Drawing Sheets

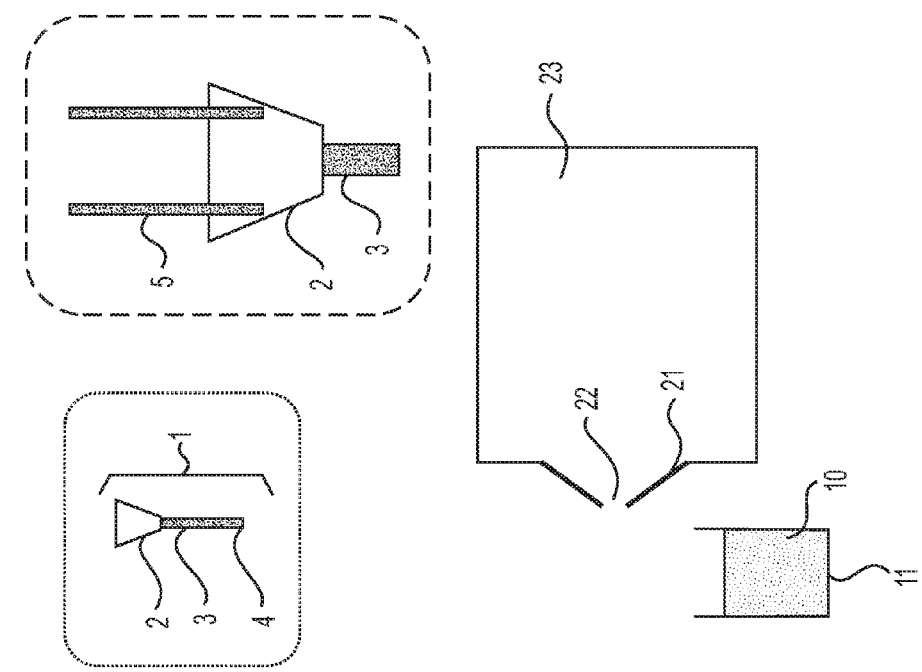
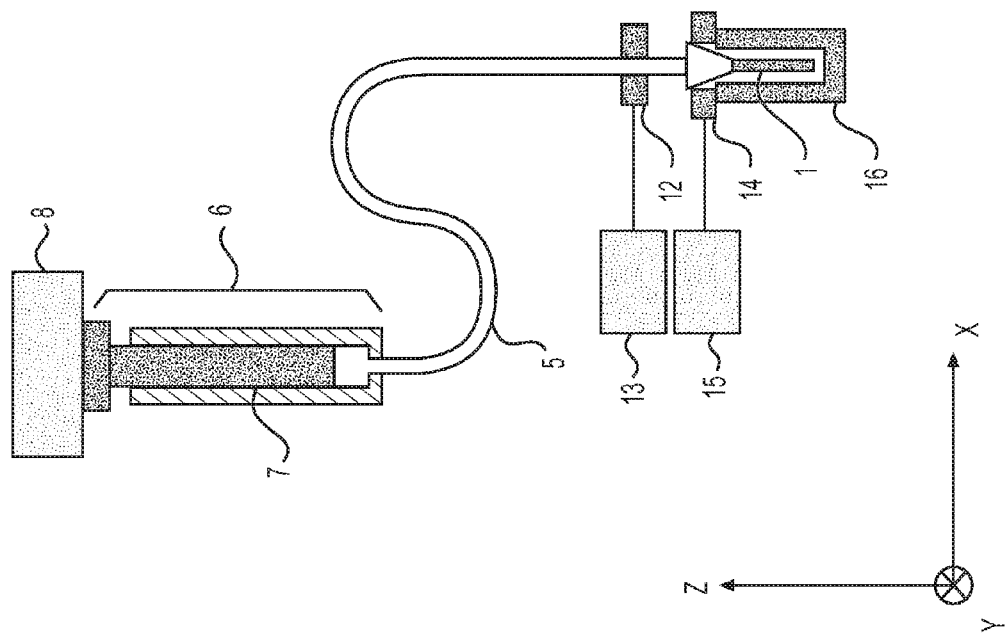
FIG. 2

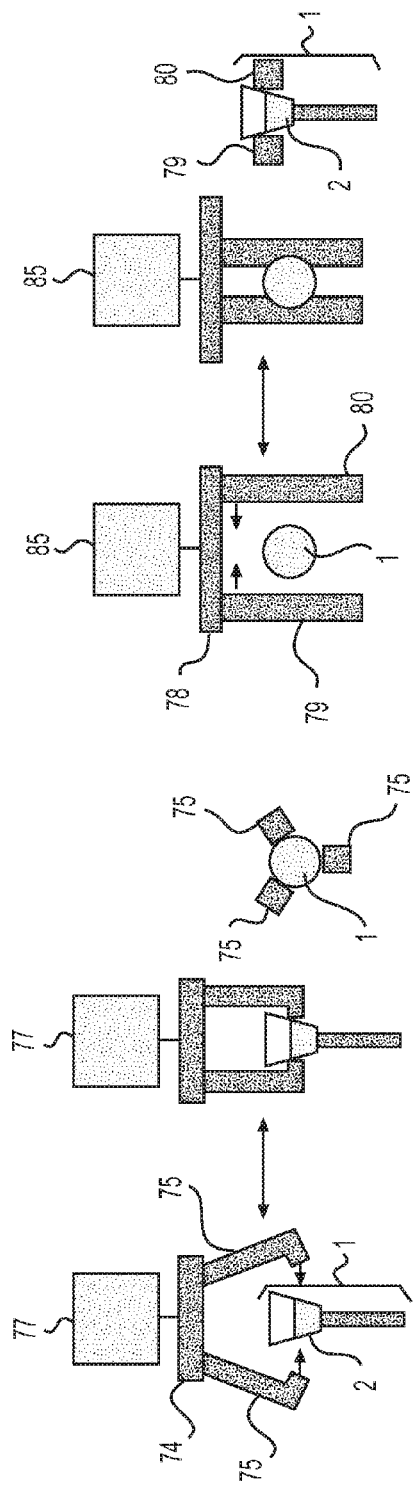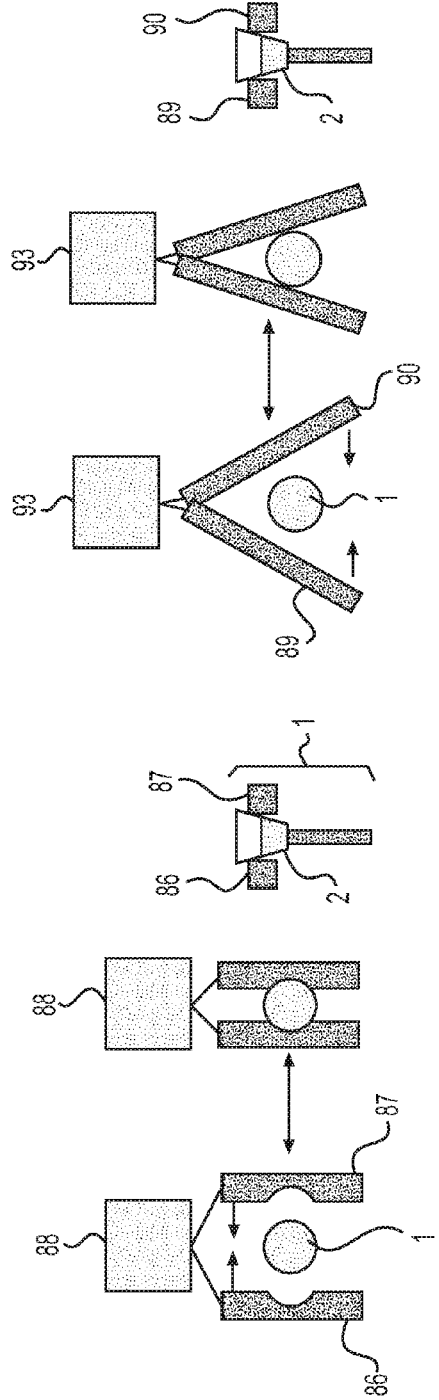
FIG. 12A  FIG. 12B  FIG. 12C  FIG. 12D

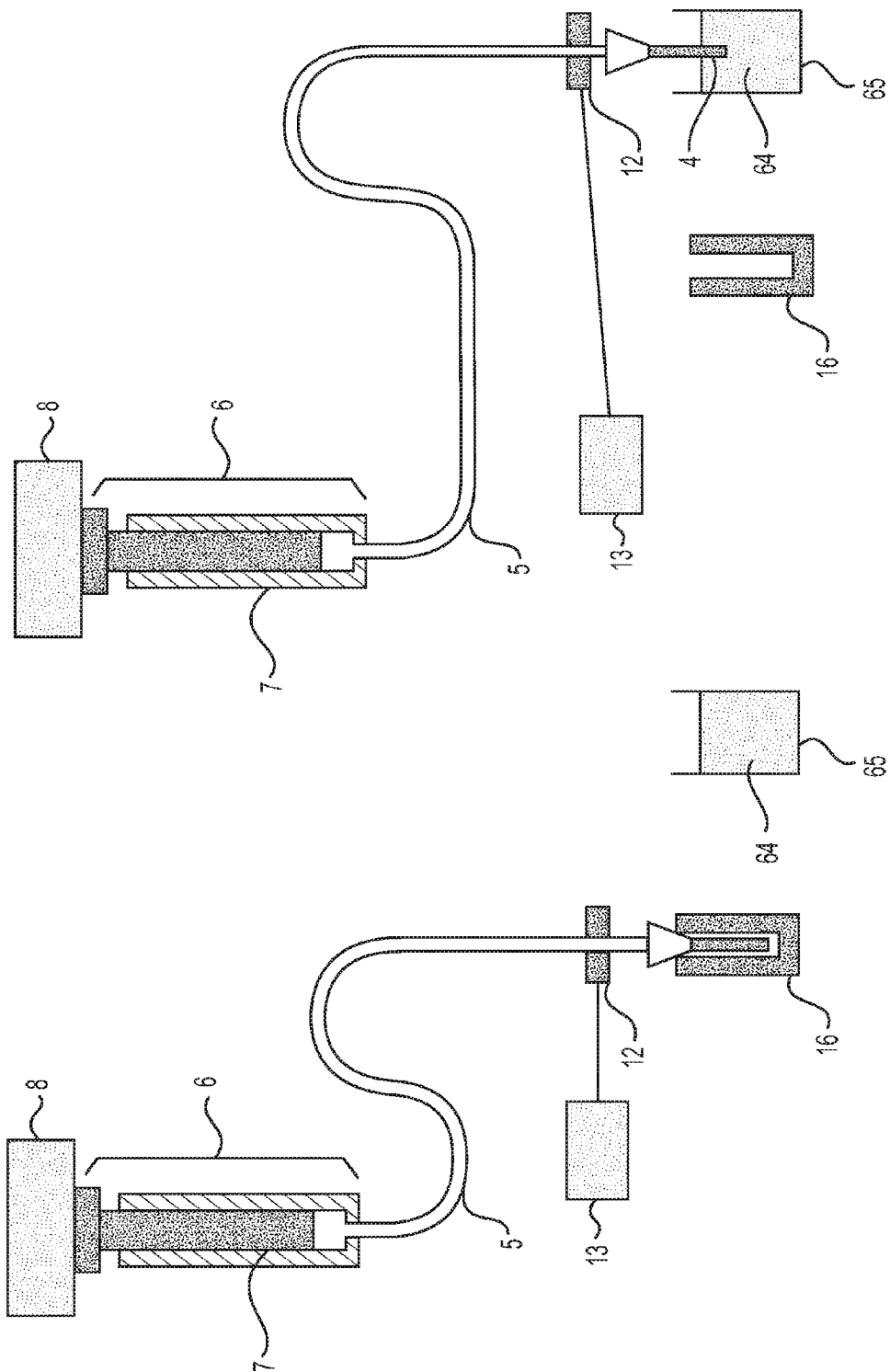

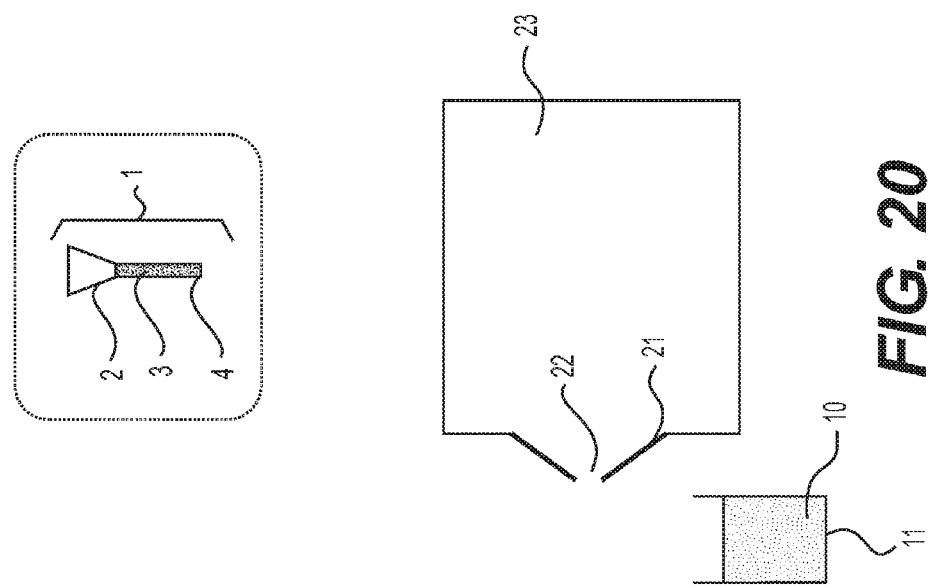
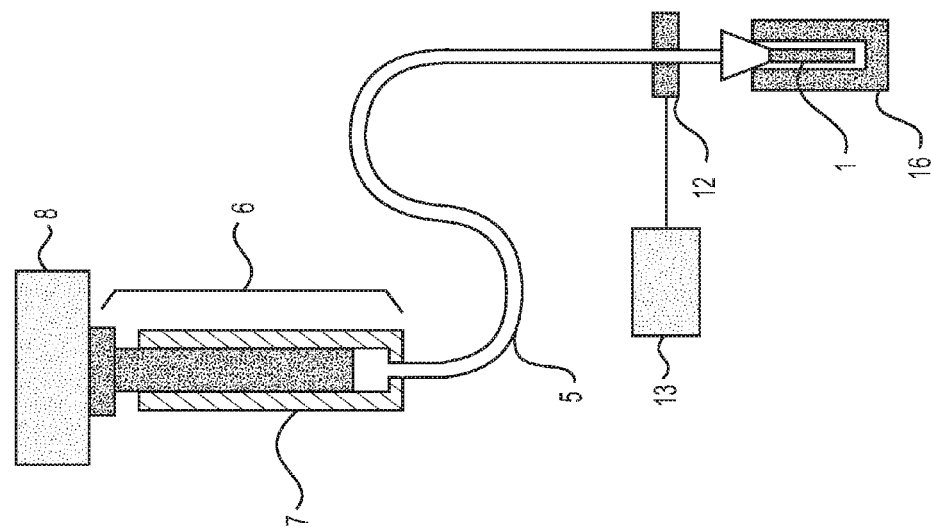
FIG. 20

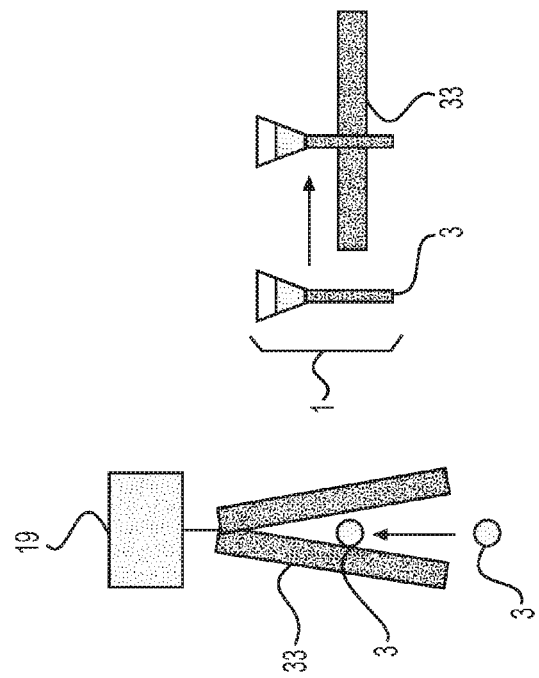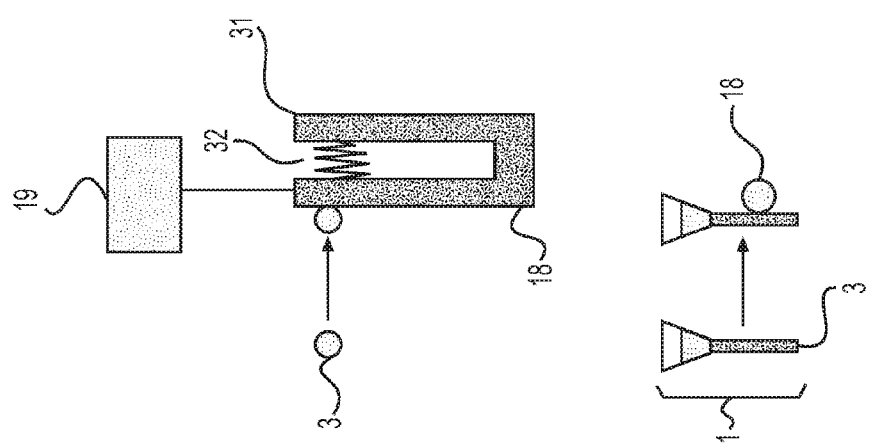
FIG. 26A
FIG. 26B

IONIZATION METHOD, IONIZATION APPARATUS, AND MASS ANALYSIS SYSTEM

TECHNICAL FIELD

The present invention relates to a technique that ionizes a sample and a technique that analyzes an ionized sample.

BACKGROUND ART

A liquid chromatography/mass spectrometer (LC/MS) is widely used in the analysis of biometric samples, for example. In the ion source of the LC/MS, gaseous ions are generated from a liquid sample separated in the LC, and introduced into amass analyzing unit. For an ionization method in the ion source, a spray ionization method according to electrospray ionization (ESI) is widely used. A capillary that is a tube in the inner diameter generally ranging from about a few μm to a few 100 μm is used between the LC and the ion source of the mass spectrometer. The electrsospray ionization is generally performed at an atmospheric pressure, in which a high voltage is applied across the liquid sample at the end portion of the capillary tubed to the LC and a counter electrode (the inlet of the mass analyzing unit), and charged droplets are generated by the electrostatic spraying phenomenon. The generated charged droplets are evaporated, and gaseous ions are generated. The efficiency of generating gaseous ions is more increased, as the size of the first generated charged droplet is smaller and the charge amount is higher.

In electrospray ionization in these years, nano-electrospray is being conducted in which the inner diameter of a capillary used for introducing a sample is downscaled to about 100 μm to about 1 to 2 μm in order to reduce the flow velocity of liquid sample. The nano-electrospray allows the measurement of a small amount of a sample for a longer time, and a small amount of biometric molecules can be analyzed.

Because of the advent of the nano-spray, the flow velocity of liquid sample for ionization is roughly divided into nano-spray at a few 100 nL/minute or less and the flow velocity at a few tens μL/minute or greater, which is the micro flow velocity. In the case of a fast flow velocity of liquid sample at a few tens μL/minute or greater, a heated spray gas is generally used in order to promote the desolvation of a liquid sample.

CITATION LIST

Patent Literatures

PTL 1: U.S. Pat. No. 6,245,227
PTL 2: WO 2007/126141
PTL 3: U.S. Pat. No. 7,364,913

SUMMARY OF INVENTION

Technical Problem

In electrospray and nano-electrospray, a slim capillary (tube) in the inner diameter ranging from a few μm to a few 100 μm is used in the tube and the ion source. More specifically, a tube used in the LC/MS has a complicated, long passage tube using a switch valve, for example. In order to reduce a carry-over, it is necessary to clean the long tube every time when samples are changed. Moreover, it is necessary to clean the tube for at least about a few minutes. When a measurement sample is insufficiently washed by cleaning and remains as a contaminant in the capillary, a problem arises in that a carry-over is taken place, which is detected as noise in measuring the subsequent sample, and accurate analysis is not enabled. Therefore, careful cleaning is needed, and it is necessary to entirely clean the switch valve and the tube (capillary) through which a sample is passed. For the cleaning, an enormous amount of a solvent to be supplied is necessary, which is formed of water, methanol, acetonitrile, or the like, costs are expensive, and there is also a concern of the influence on the environment. Furthermore, another problem arises in that a capillary tube is clogged due to a sample or foreign particles and impurities included in the sample in measurement. Therefore, a novel electrospray ion source that can solve the problems is desired.

Meanwhile, PTL 1 to PTL 3 that are publicly known documents disclose an ion source that does not use a passage and a solvent for supplying as in the LC/MS. A method is described in which easily replaceable ionization needles and probes are used and a liquid sample can be introduced. The following is the advantages of the ion source. Since a liquid sample is not supplied through a long passage as in the LC/MS, the amount of a solvent supplied can be reduced. Moreover, since ionization needles and probes are used which are easily replaceable as compared with conventional ion sources, a problem of clogged foreign particles is hardly taken place and cleaning is unnecessary. Furthermore, it is expected that a carry-over in the tube and in the ion source is greatly improved. However, it is assumed that the publicly known techniques have some problems. In the following, the characteristics and problems of the exemplary publicly known techniques will be described.

PTL 1 discloses a method in which a silicon substrate having a plurality of holes is used and the individual holes are used as ionization needles for ionization. This method is a method in which a liquid sample suction-and-transport chip on which a liquid sample is held is joined to an ionization needle, and the sample is sprayed and ionized, and the method is a method that can change an ionization needle and a chip for every sample. Ionization needles and chips to which a sample is attached are all disposable, and are unnecessary to be cleaned, and the problems of clogging and a carry-over are greatly reduced. However, there is a problem in that a silicon chip substrate is expensive. More specifically, since microfabrication is necessary to form a silicon substrate having a large number of holes in a diameter of a few μm, it is predicted that the component itself becomes expensive, and there is a practical problem for the analysis of a large number of samples. Moreover, since it is necessary to clean the tube to which a sample is supplied, a problem is not completely solved in that the tube is contaminated by every sample.

PTL 2 discloses an ionization method in which a probe (a needle) is vertically reciprocated between the position of the origin point and a sample unit and the probe is repeatedly attached to a sample (sampling) and performs ionization. Since a liquid sample is attached to the surface of the probe and the liquid sample flows to the tip end along the probe, ionization is performed by applying a high voltage to the probe. Since a hollow tube like a capillary is not used and a liquid is supplied along the surface of a needle, a problem does not arise in that a tube is clogged, and only the surface of the needle is cleaned, so that the needle is cleaned more easily than in cleaning the tube, and a carry-over is also reduced. When a probe is replaced for every sample, it is unnecessary to clean the probe, and a problem of a carry-over is also solved. However, it is assumed that the ionization method in which the needle is vibrated has a problem in that since a sample is not ionized in sampling, ionization is performed intermittently and discretely, and the throughput of analysis is reduced. Moreover, since the needle is reciprocated at high speed, there is a concern that ionization becomes unstable and ion intensity of sample does not become stable.

PTL 3 discloses a method in which a sample suction-and-transport chip and a syringe are used as ionization needles as they are for ionization. This is a method in which after a sample is sucked into the ionization needle, the ionization needle is joined to the gas spray tube of an ion source unit for ionization, and then ionization is performed. Even though the chip and the needle are disposable, the ion source unit including the gas spray tube is not disposable, so that the ion source portion is contaminated, and a problem of a carry-over arises.

The present disclosure discloses a solution that can solve the problems of the publicly known literatures.

Solution to Problem

The problems are solved by the following solution, for example. The solution is an ionization method using an ionization unit having a sample holder configured to hold a sample, an ionization unit drive unit configured to drive the ionization unit, a power supply configured to apply a voltage to the ionization unit, and a tube connected to the ionization unit, the method including the steps of: joining the ionization unit to the tube; sucking the sample from a sample container into a sample holder of the ionization unit to hold the sample; moving the ionization unit holding the sample to near the ionization unit using the ionization unit drive unit; and applying a voltage to the ionization unit using the power supply to ionize the sample by electrostatically spraying the sample from the sample holder.

Advantageous Effects of Invention

According to the present disclosure, there is provided an ionization method using an ionization needle disposable for every sample and easily replaceable. Thus, the carry-over of a sample and crosstalk between measurements are reduced, which are problems so far. Moreover, the clogging of the tube and the needle with foreign particles and a sample, for example, is greatly reduced. Furthermore, the cleaning step is unnecessary, so that the throughput of analysis is improved. As these results, the reproducibility of analyzed data is improved, and it is possible to perform the analysis of high quantitative precision and the analysis of a high throughput.

BRIEF DESCRIPTION OF DRAWINGS

FIG. 2 is a diagram of an exemplary structure and a use form of an ion source according to a first embodiment (a joining step).

FIGS. 12A to 12D are diagrams of other structures and motions of arms.

FIGS. 19A and 19B are diagrams of still yet another cleaning method according to the second embodiment.

FIG. 20 is a diagram of an exemplary structure and a use form of an ion source according to a third embodiment (a joining step).

FIGS. 26(A) and 26(B) are diagrams of another method for applying a voltage.

DESCRIPTION OF EMBODIMENTS

In the following, embodiments of the present invention will be described with reference to the drawings. It is noted that the content of device configurations and the operations of processes, described later, is an example, and other embodiments can be achieved by combining and replacing the embodiment with known techniques.

First Embodiment

Figure 1:
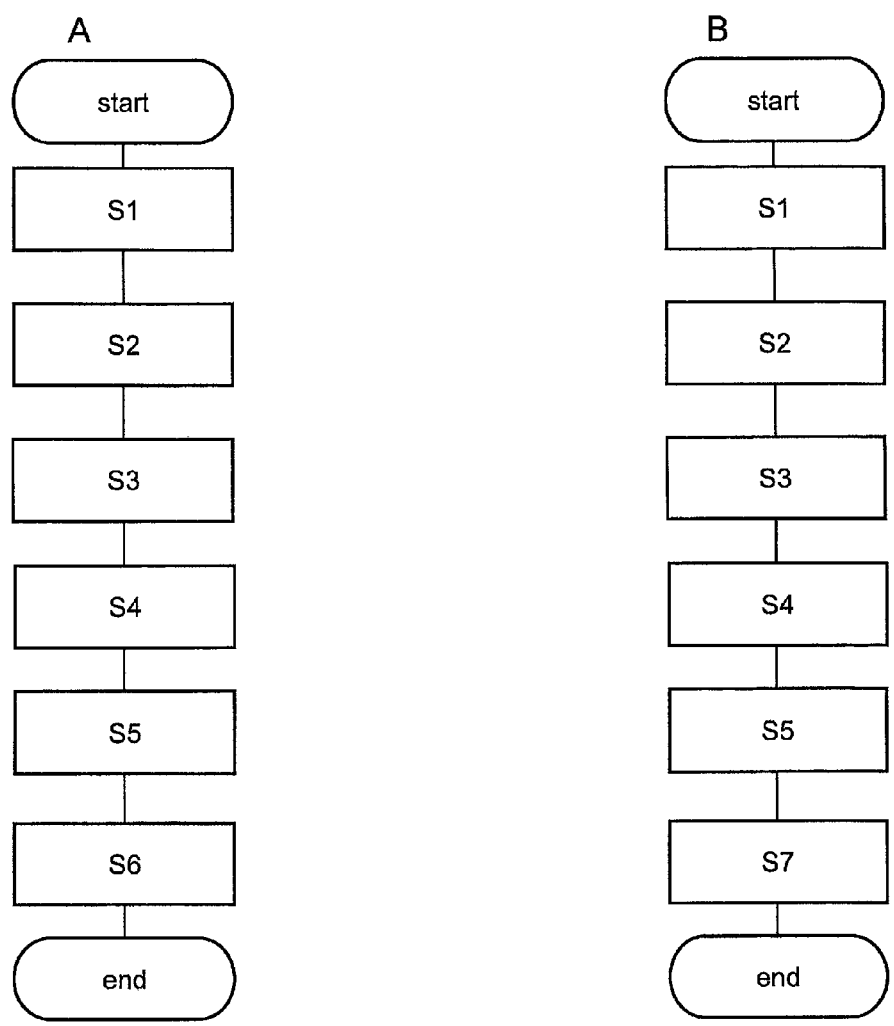
FIGS. 1A and 1B are flowcharts of an embodiment.

In the embodiment, a transport operation and an ionization method for an ionization needle and a sample will be described in the sampling unit and the ionization unit of a mass spectrometer. In an ion source according to the embodiment, a method is that a tube was not used as in the conventional methods, a disposable needle is used for the ionization needle, and the ionization needle only contacts a sample. The method is a method in which a syringe is used for the supply (suction) of a sample to the ionization needle, and the sample supplying (discharge) from the ionization needle in ionization is performed according to gravity drip (gravity drop) by gravity. FIGS. 1A and 1B are flowcharts of the ionization operation, and FIGS. 2 to 7 are schematic diagrams of the configuration and the operation of an ion source and a mass analyzer according to an embodiment of the present invention when seen from the lateral side, and FIG. 8 is an overall diagram when seen from above.

The steps of the measurement operation according to the embodiment includes a joining step S1, a moving step S2, a sucking step S3, a moving step S4, an ionization step S5, and a discarding step S6 (FIG. 1A).

The joining step S1 is the step of joining a tube 5 to a sample container 2 of an ionization needle 1 (FIG. 2). The ionization needle 1 includes the sample container 2 that holds and ionizes a sample and a metal capillary 3, and a plurality of the ionization needles 1 is arranged and disposed in a needle storage unit 16. The upper part of the sample container 2 of the ionization needle 1 is opened, the diameter of the opening is wider than the diameter on the metal capillary 3 side, and the sample container 2 is in a tapered shape as illustrated in the drawing. The sample container 2 is in a tapered shape, so that the tube 5 can be intimately joined to the inner wall of the sample container 2, and can prevent the leakage of a liquid (FIG. 2). The tube 5 is mounted with an arm 12 whose operation is controllable by a transport drive unit 13, and the arm 12 can be moved in X-, Y-, and Z-directions.

Figure 3:
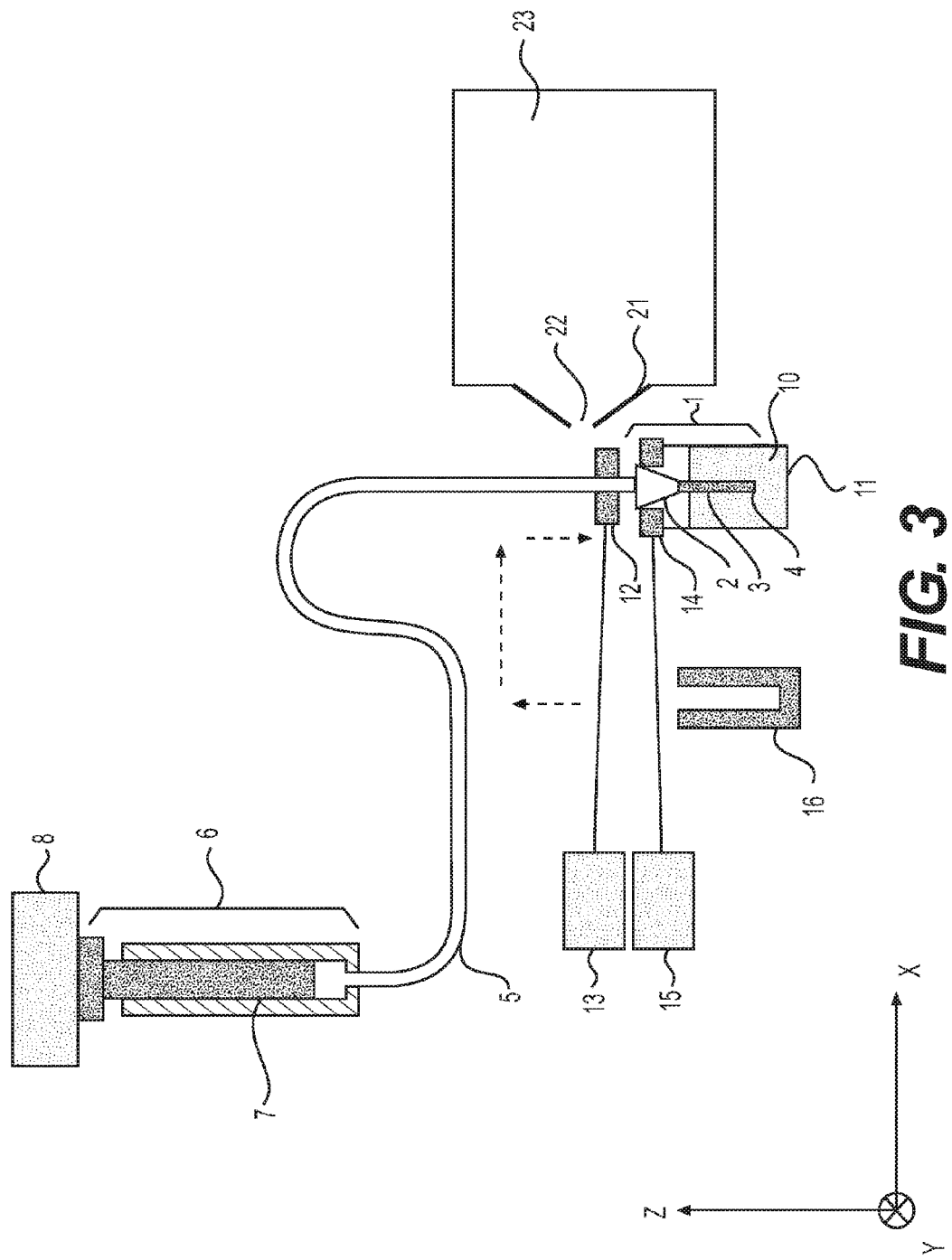
FIG. 3 is a diagram of an exemplary structure and a use form of the ion source according to the first embodiment (a moving step).

The moving step S2 is the step of moving a needle tip end 4 of the ionization needle 1 into a liquid sample 10 in order to suck the sample (FIG. 3). The ionization needle 1 is mounted with an arm 14, and the ionization needle 1 is moved by a transport drive unit 15 that drives the arm 14. In moving, it may be fine that the arm 12 is moved as the same motion as the arm 14 while being mounted on the tube 5, or that the arm 12 is detached from the tube 5. The ionization needle 1 is temporarily moved upwardly by the arm 14 connected to the transport drive unit 15 (in the positive Z-axis direction), and is moved horizontally to above a sample pot 11 containing the liquid sample 10 (in the positive X-axis direction). After that, the ionization needle 1 is moved downwardly (in the negative Z-axis direction) until the needle tip end 4 of the ionization needle 1 is dipped into the liquid sample 10.

Figure 4:
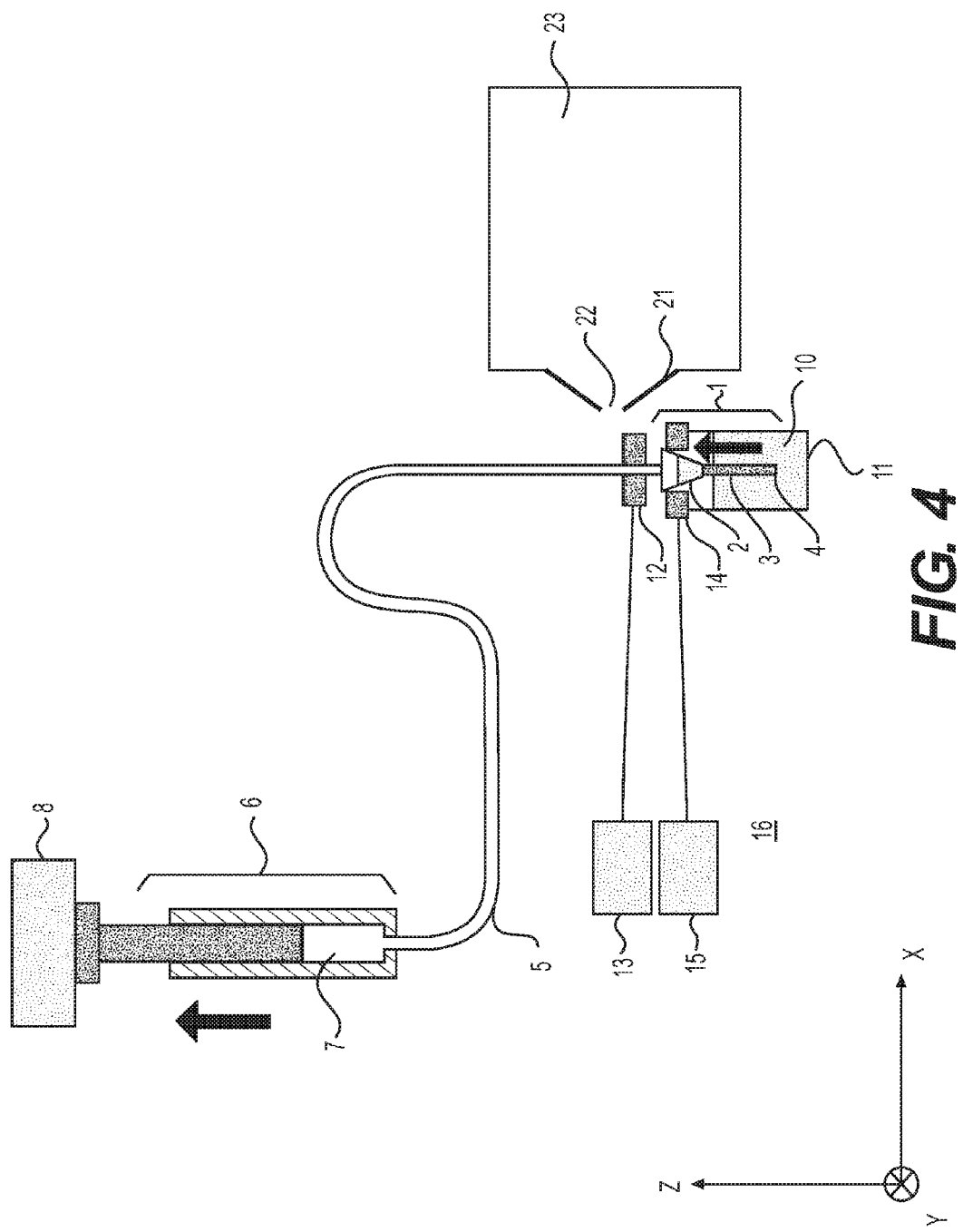
FIG. 4 is a diagram of an exemplary structure and a use form of the ion source according to the first embodiment (a sucking step).

The sucking step S3 is the step of sucking the liquid sample 10 into the sample container 2 (FIG. 4). The inside of the metal capillary 3 of the ionization needle 1 is in a tube structure through which the liquid sample 10 can be passed. A syringe 6 is used to suck the sample, and a syringe piston 7 is vertically operated in the Z-axis direction by a syringe pump 8. The tube 5 is connected to the syringe 6, and the pressure of the inside of the sample container 2 is reduced by lifting the piston 7 in the positive Z-axis direction by the syringe pump 8. At this time, the liquid sample 10 contained in the sample pot 11 is sucked from the needle tip end 4, passed through the inside of the metal capillary 3, and introduced into the sample container 2. After sucking a predetermined liquid amount, the syringe pump 8 stops the operation, and the piston 7 of the syringe 6 also stops the operation. The piston 7 stops and maintains the position, so that it is possible to prevent the liquid sample from flowing out of the needle tip end 4 of the ionization needle 1. Desirably, the sucked amount of the liquid sample is an amount to the extent that the liquid does not contact the tube 5, that is, to the extent that the tube 5 is not contaminated. Thus, it is possible to eliminate the cleaning of the tube 5.

Figure 5:
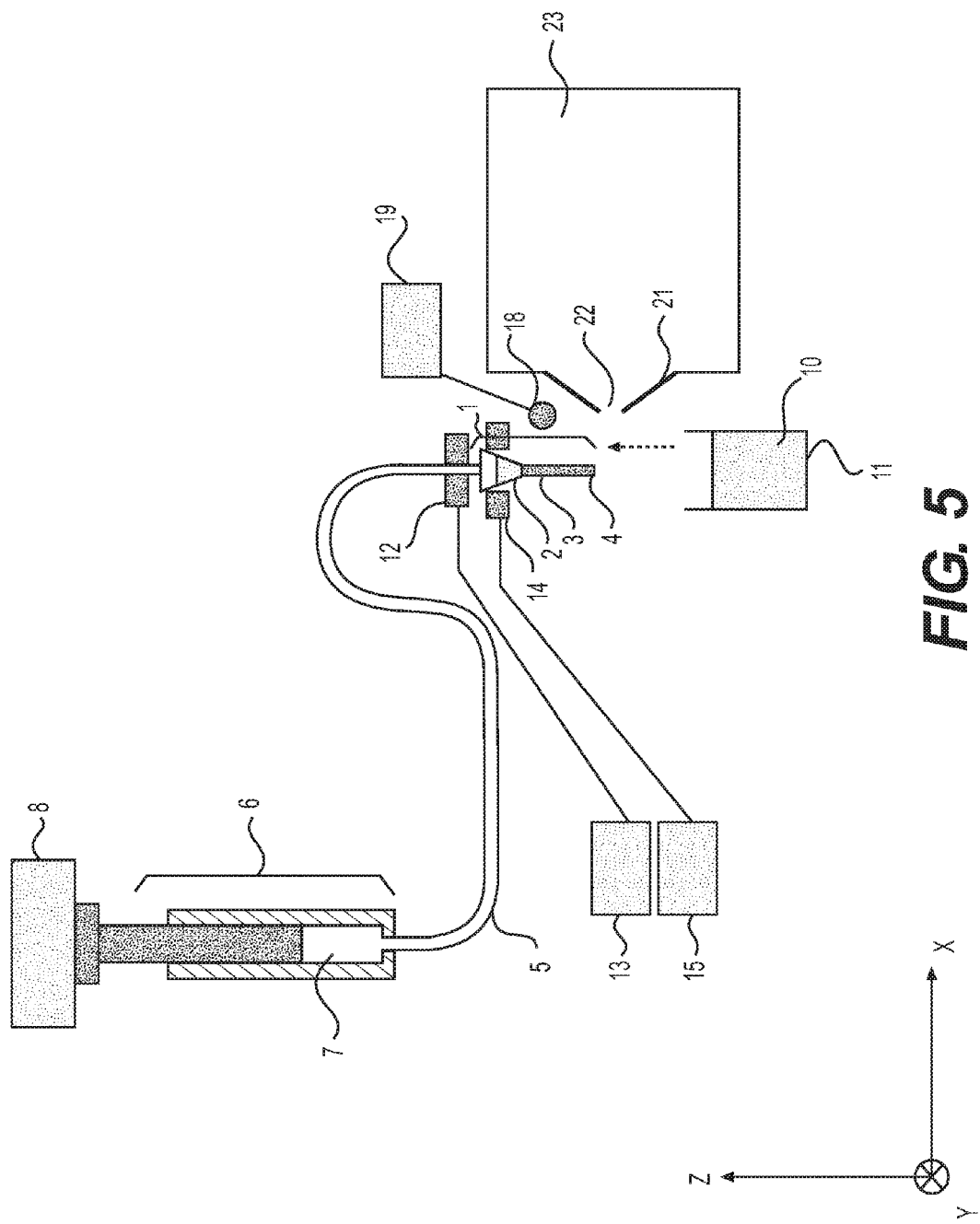
FIG. 5 is a diagram of an exemplary structure and a use form of the ion source according to the first embodiment (a moving step).

The moving step S4 is the step of moving the ionization needle 1 to the position at which ionization is performed in the mass spectrometer (FIG. 5). The ionization needle 1 in which the liquid sample 10 is filled in the sample container 2 is moved upwardly (in the positive Z-axis direction) by the transport drive unit 15 that drives the arm 14. The needle tip end 4 of the ionization needle 1 is moved so as to come to near a pore 22 of a counter electrode 21, which is the inlet port of the mass spectrometer.

Figure 6:
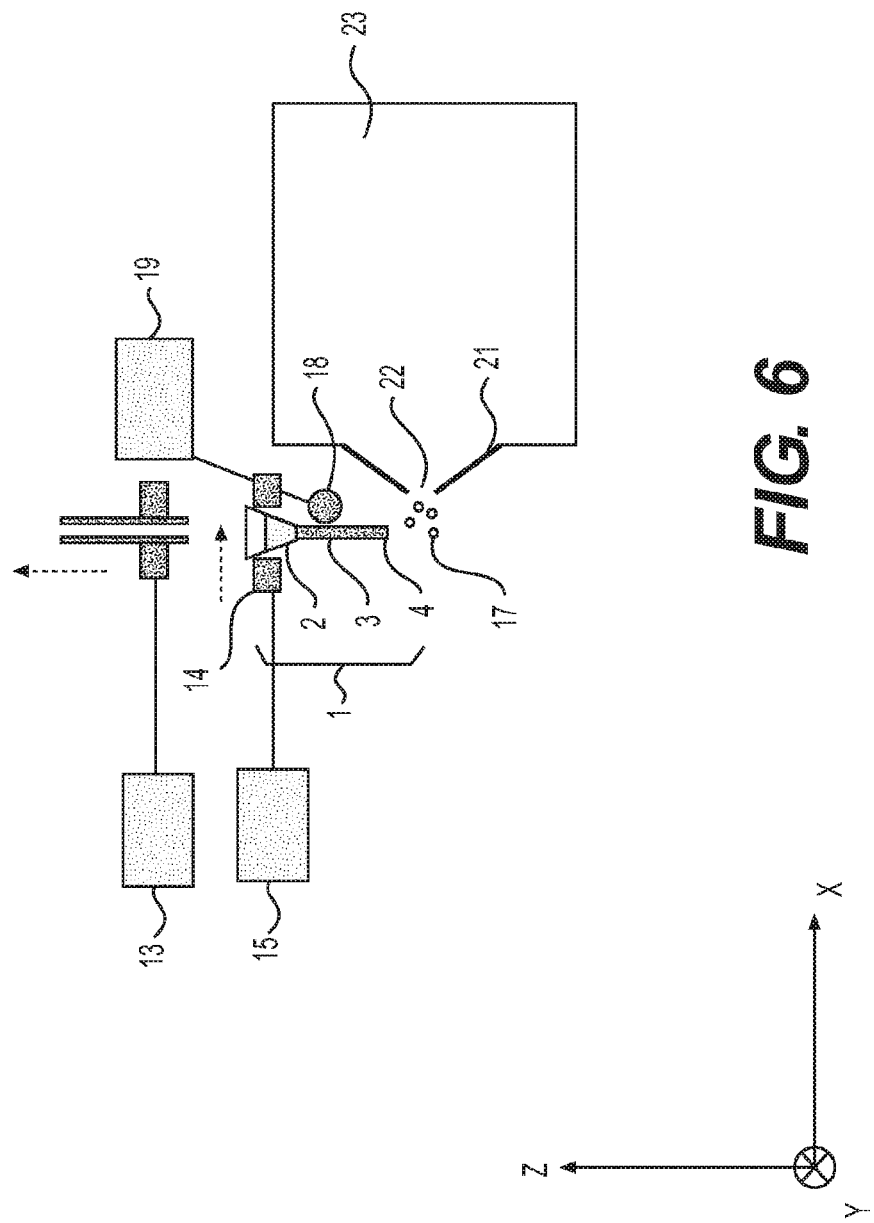
FIG. 6 is a diagram of an exemplary structure and a use form of the ion source according to the first embodiment (an ionization step).

The ionization step S5 is the step in which a voltage is applied to the metal capillary 3 of the ionization needle 1 and ionization is performed by supplying the liquid sample (FIG. 6). The ionization step includes two steps, the step of applying a voltage and the step of supplying the sample. The step of applying a voltage is performed by the following method. A voltage is applied from a high voltage power supply 19 to the metal capillary 3 for electrostatic spraying from the tip end 4 of the metal capillary 3. The transport drive unit 15 and the arm 14 are used to move the ionization needle 1 in the positive X-axis direction, the metal capillary 3 is contacted to a contact terminal 18 connected to the high voltage power supply 19, and a voltage is applied to the metal capillary 3. After a voltage is applied to the metal capillary 3, the supplying of the liquid sample 10 is started. The supplying of the liquid sample is started by detaching the tube 5 from the sample container 2. At the same time of the detachment, the liquid sample is electrostatically sprayed out of the tip end 4 of the ionization needle 1 due to gravity drop by gravity, and electrospray is performed. Generated ions 17 enters a detecting unit 23 from the pore 22, and is detected.

Figure 7:
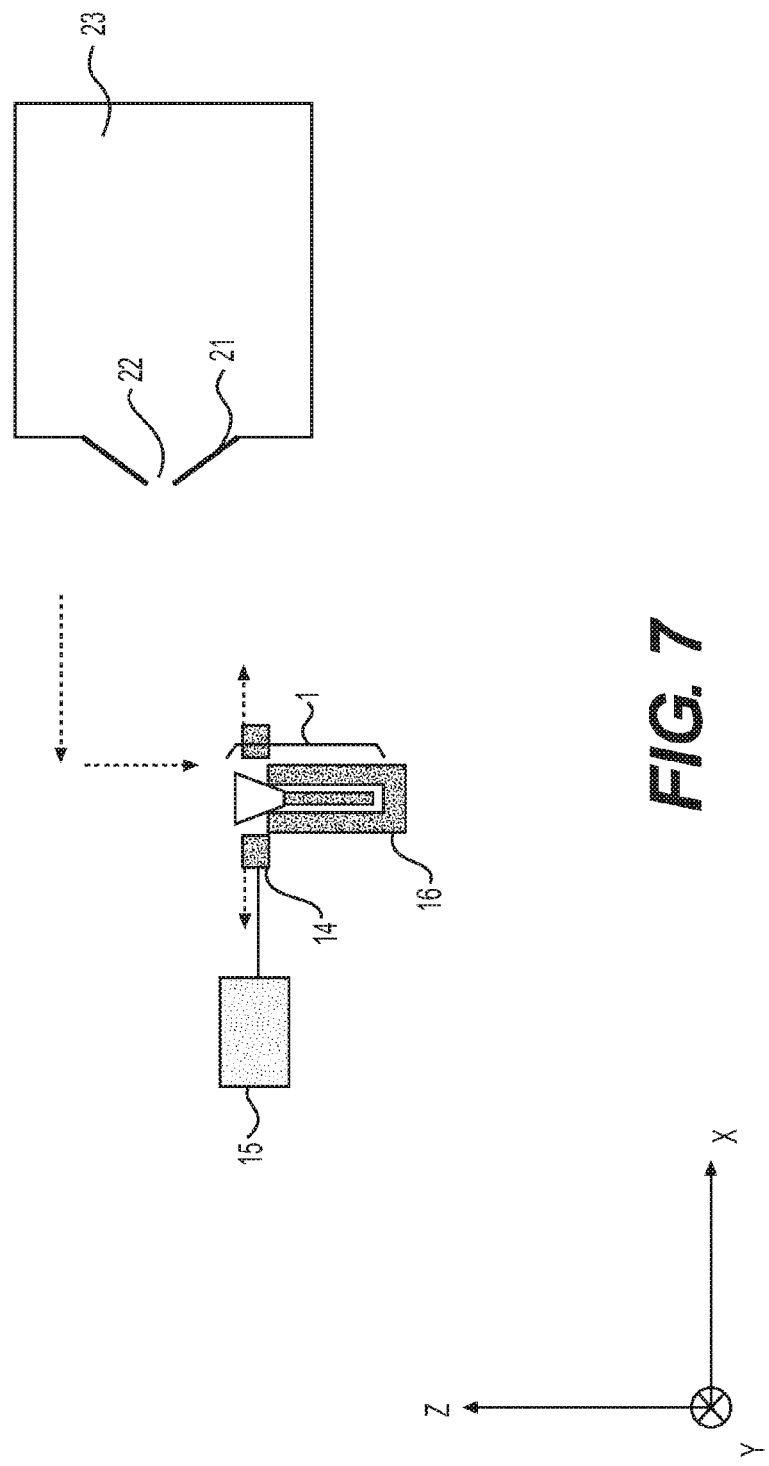
FIG. 7 is a diagram of an exemplary structure and a use form of the ion source according to the first embodiment (a discarding step).
Figure 8:
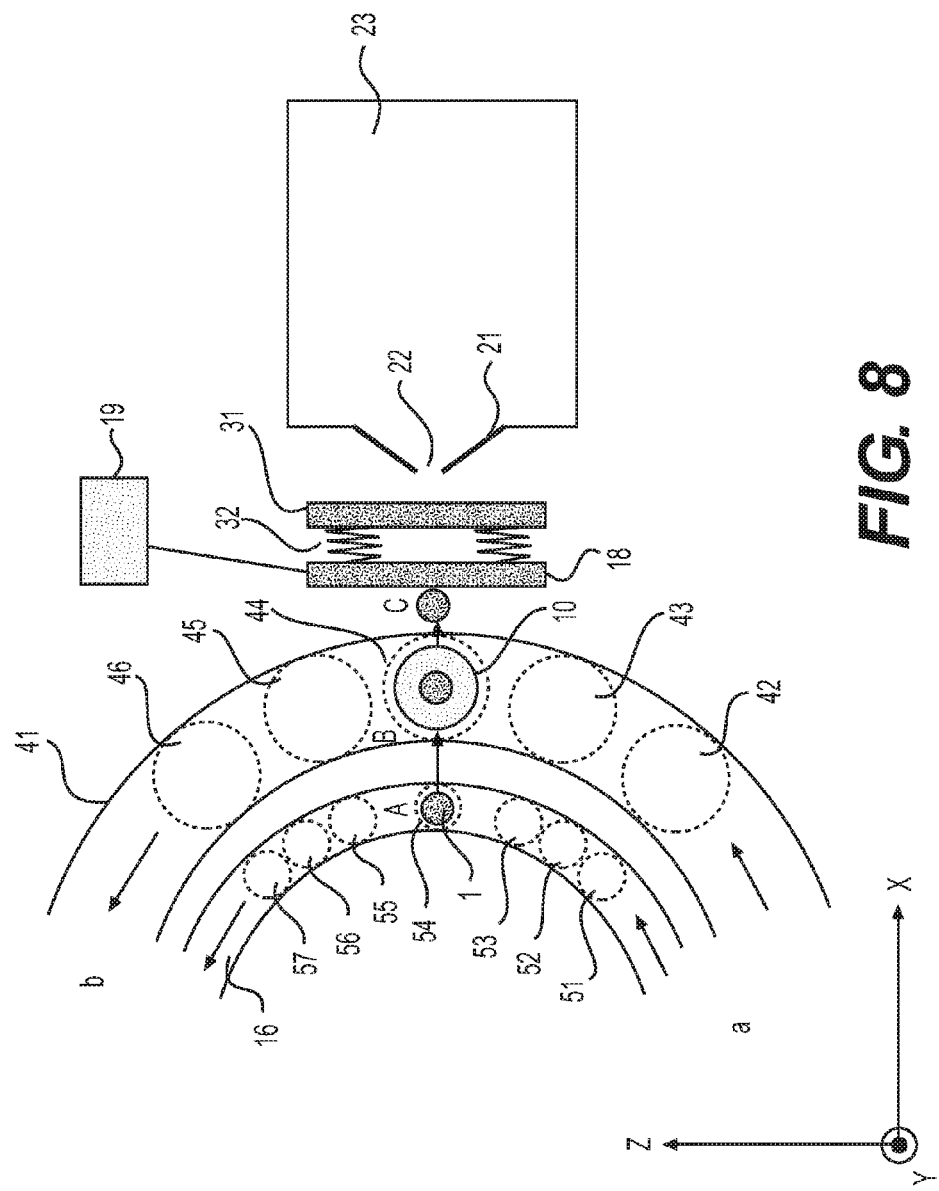
FIG. 8 is a diagram of an exemplary structure and a use form of the ion source according to the first embodiment (an overall diagram).

The discarding step S6 is the step of discarding the used ionization needle 1 (FIG. 7). The ionization needle 1 that ionization is performed for a preset time and measurement is finished is returned to the original position in the needle storage unit 16 by the drive unit 15 that drives the arm 14. At this time, the ionization needle 1 is moved in the negative X-axis direction, and moved in the negative Z-axis direction. After moving the ionization needle 1, the arm 14 is opened by the transport drive unit 15, and the ionization needle 1 is returned to the needle storage unit 16. Alternatively, the ionization needle 1 may be discarded into a trash bin separately prepared.

The ion source using the ionization needle can operate under an atmospheric pressure. The metal capillary 3 of the ionization needle 1 is a conductive material like a metal and is a slender tube that a liquid can be passed through the inside of the capillary. The tip end 4 of the metal capillary 3 is cut flat as illustrated in the drawing, at which ionization can be performed. Moreover, ionization can also be performed in one whose tip end is cut obliquely and sharply. Analysis can be performed by the sample container 2 as long as the sample container 2 is one that can hold a sample of about a few tens to a few 100 µL. A voltage for electrospray applied to the metal capillary 3 is generally a voltage of about 1 kV to 6 kV, and electrospray ionization is performed at the voltage. The solvent for the liquid sample may be the same solvent used in a general LC/MS or a mass spectrometer, and is methanol, acetonitrile, water, and the other organic solvents, and a mixture of these, for example.

The steps S1 to S6 will be described in the flow of the motion of the ionization needle 1 with reference to FIG. 8 that is a diagram seen from above the apparatus. A plurality of the ionization needles 1 is arranged in the needle storage unit 16. New ionization needles are arranged at positions 51, 52, and 53, a new ionization needle used for measurement is arranged at a position 54, and used ionization needles are arranged at positions 55, 56, and 57. The ionization needle is moved from the position 51 to the positions 52, 53, 54 to 57 over the needle storage unit 16 in a belt conveyor system. The ionization needle 1 moved to the position 54 (location A) is joined to the tube 5 at location A (the joining step S1). In the moving step S2, the ionization needle 1 is moved to location B, and the sucking step S3 and the moving step S4 are performed. After that, in the ionization step S5, the ionization needle 1 is moved to location C, and again returned to location A in the discarding step S6.

Subsequently, the motion of the sample pot 11 will be described. A plurality of the sample pots 11 containing the liquid sample 10 is arranged in a sample pot storage unit 41. Sample pots before subjected to measurement are arranged at positions 42 and 43, a sample pot under measurement is arranged at a position 44 (location B), and sample pots after subjected to measurement are arranged at positions 45 and 46. The sample in the sample pot 11 moved to location B is sucked into the sample container 2 in the sucking step S3. After finishing measurement, the sample pot is in turn moved to the positions 45 and 46. Similarly to the needle storage unit 16, the sample pot storage unit 41 can transport the sample pot in a belt conveyor system, and can move the sample pot one by one. After sucking the sample, when the sample pot is immediately moved to the position 45 and is apart from the vicinity of the ionization unit prior to ionization and measurement, this is measures to prevent contamination from outside and the liquid sample can be reused. Alternatively, a lid is provided for the sample pot to prevent contamination similarly. As described above, the ionization needle and the sample pot are transported, so that the sample can be measured one by one. It may be possible that the operations of the drive unit, the sample pot storage unit 41, the needle storage unit 16, and the like are controlled using a personal computer, for example, and the operations are performed in a full automatic manner or in a semiautomatic manner.

The structure and the method for applying a high voltage to the metal capillary 3 for ionization will be described with reference to FIG. 8. A high voltage is applied from the high voltage power supply 19 to the metal capillary 3 of the ionization needle 1 using the contact terminal 18. The contact terminal 18 is mounted on a spring 32 mounted on a fixing unit 31. A material such as plastic and PEEK is used for at least one of the spring 32 and the fixing unit 31 so as not to carry an electric current. It is fine that the contact terminal 18 is a conductive material such as a metal that caries electricity. In order to apply a voltage, the metal capillary is moved in the positive X-direction, and the metal capillary 3 is contacted with the contact terminal 18. At this time, the spring 32 is compressed, so that the metal capillary 3 can be in intimate contact with the contact terminal 18, and a voltage can be stably supplied to the metal capillary 3. The spring 32 may be one, two, three, or more.

Figure 9:
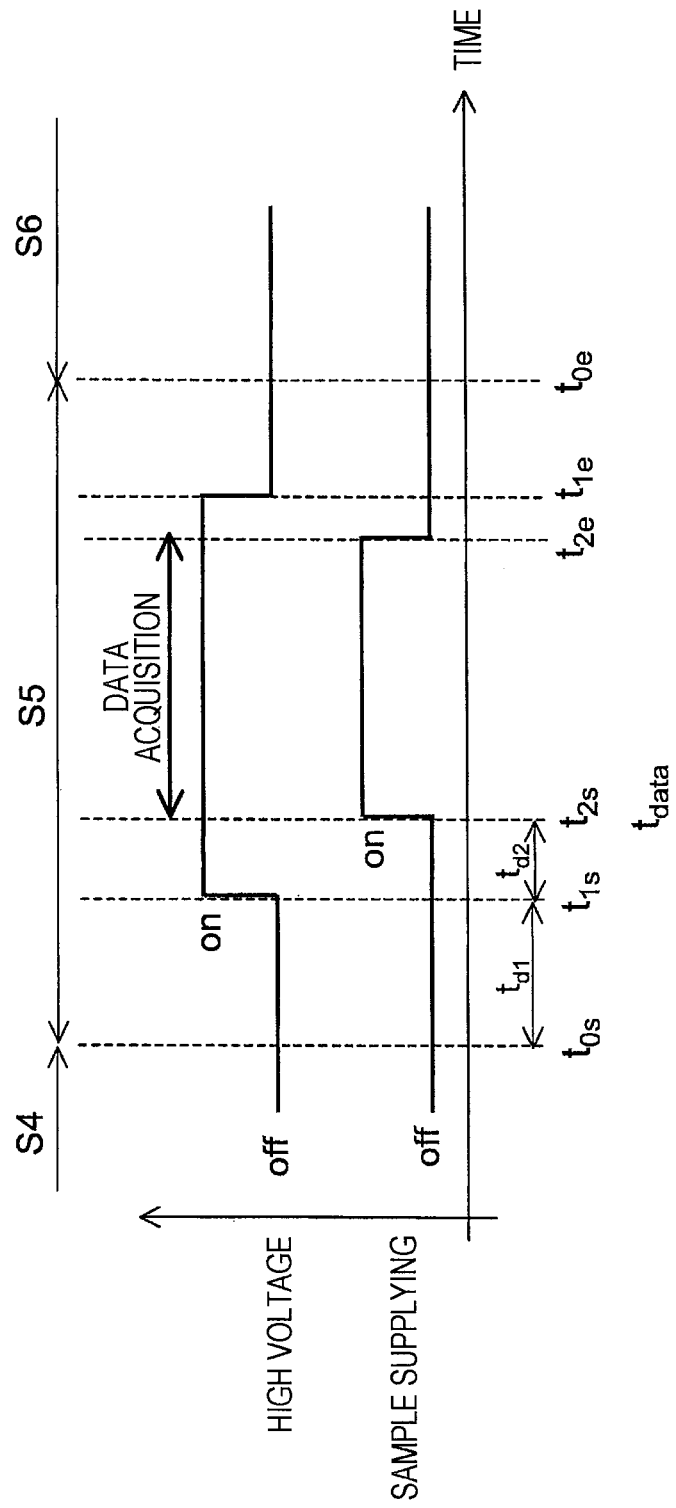
FIG. 9 is a diagram of time sequences of voltage application and sample supplying according to the first embodiment.

A desirable time sequence in the ionization step S5 will be described. FIG. 9 is the time sequence to turn on/off the high voltage of the high voltage power supply 19 and the supplying of the liquid sample in performing the ionization step S5. On the vertical axis expressing the high voltage, a voltage of a few kV is applied when the voltage of the high voltage power supply 19 is turned on, whereas 0 V is applied when turned off. Moreover, on the vertical axis expressing the supplying of the liquid sample, the states are expressed in which the liquid sample in the sample container 2 flows out of the needle tip end 4 due to gravity drop as the tube 5 is detached when sample supplying is turned on, and in which the tube 5 or the lid is attached to the sample container 2, the upper part of the sample container 2 is sealed, and sample supplying is stopped when sample supplying is turned off. Time on the horizontal axis describes time to start the ionization step S5 as $t_{0\_s}$, time to finish the ionization step S5 as $t_{0\_e}$, high voltage application start time (on) as $t_{1\_s}$, high voltage application termination time (off) as $t_{1\_e}$, sample supplying start time (on) as $t_{2\_s}$, and sample supplying termination time (off) as $t_{2\_e}$.

The high voltage application and sample supplying are performed along the following sequence. The application of a high voltage is started at $t_{1\_s}$ after a lapse of delay time $t_{d1}$ (zero to about a few seconds) from the start time $t_{0\_s}$ for the ionization step S5. After that, sample supplying is started at $t_{2\_s}$ after a lapse of delay time $t_{d2}$ (a few ms to about a few seconds) from $t_{1\_s}$. It is desirable to set the voltage application start time $t_{1\_s}$ before the sample supplying start time $t_{1\_e}$ because the consumption of the liquid sample is suppressed. Upon starting sample supplying, electrostatic spraying is started and ionization is performed, so that data can be acquired. After a lapse of a predetermined data acquisition time, sample supplying is turned off at $t_{2\_e}$, and a high voltage is turned off at $t_{1\_e}$ after a short delay time. No problem arises when $t_{1\_e}$ and $t_{2\_e}$ are set at the same time. Since ionization is terminated at a point in time when any one of the high voltage application and sample supplying is turned off, data acquisition is finished at that point in time. For the timing when sample supplying is turned off, since sample supplying is generally and naturally finished at timing when the sample container 2 becomes empty, a specific manipulation to turn off sample supplying is unnecessary. However, in the case where it is desired to stop sample supplying in the state in which the liquid sample remains in the sample container 2, the tube 5 is again joined to the sample container 2, or the opening of the upper part of the sample container 2 is covered with the lid for sealing, and then dripping the liquid sample is stopped.

Figure 10:
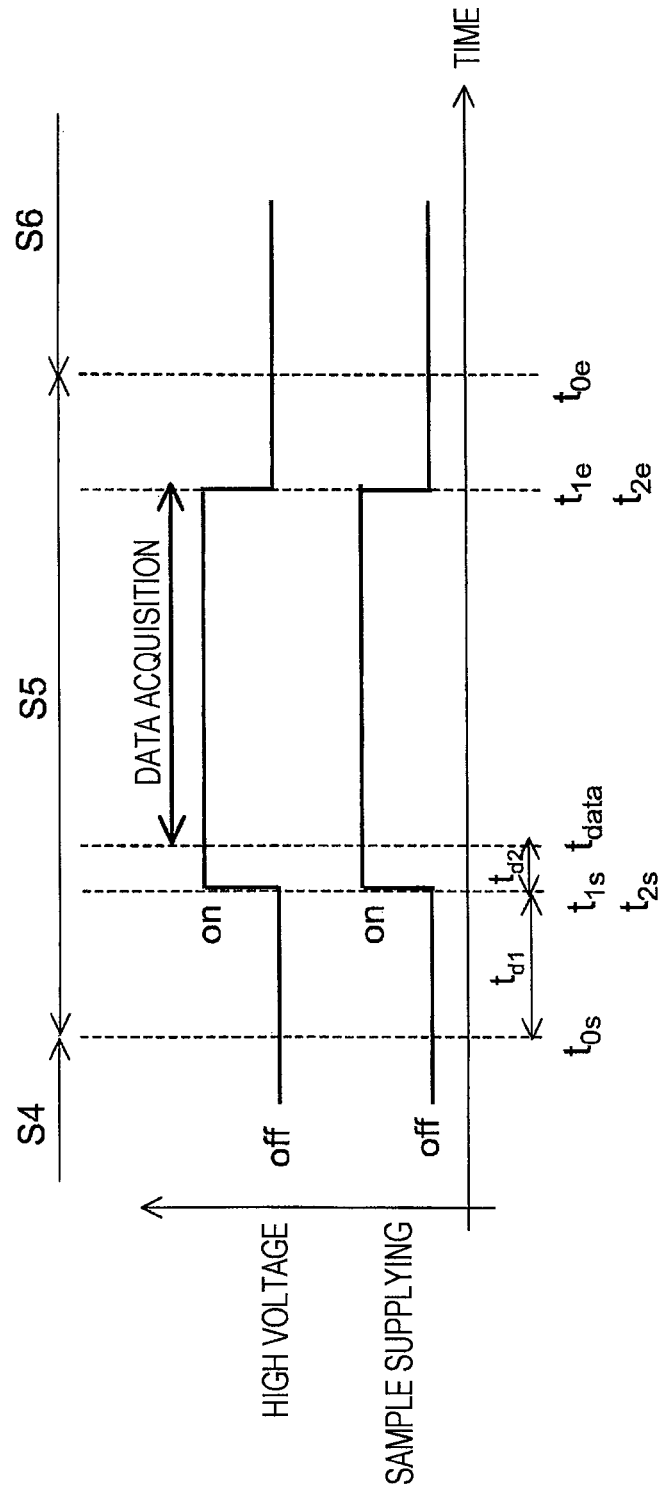
FIG. 10 is a diagram of other time sequences of voltage application and sample supplying according to the first embodiment.

FIG. 10 is an embodiment of another time sequence. In this example, after starting the ionization step, high voltage application and sample supplying are simultaneously turned on at the high voltage application start time $t_{1\_s}$ and the sample supplying start time $t_{2\_s}$ after a lapse of the delay time $t_{d1}$. After that, data acquisition is started after a lapse of the delay time $t_{d2}$. When measurement is finished, high voltage application and sample supplying are simultaneously turned off at the high voltage application termination time $t_{1\_e}$ and the sample supplying termination time $t_{2\_e}$. The delay time $t_{d2}$ may be zero.

Figure 11A:
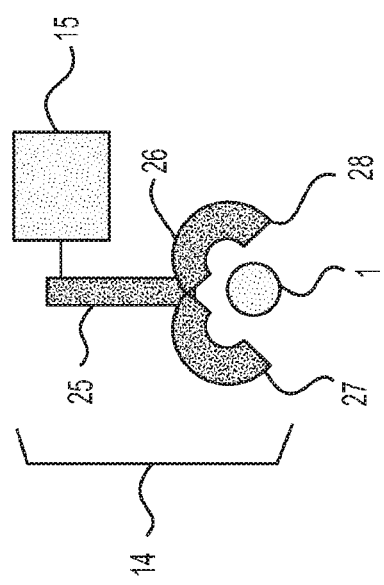
FIGS. 11A and 11B are diagrams of the structure and motion of an arm.
Figure 11B:
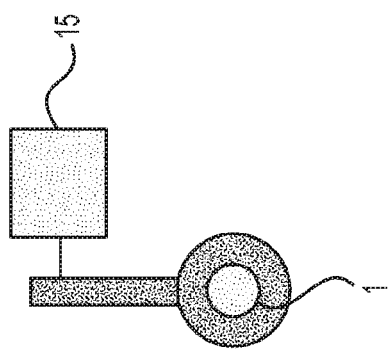

Next, the operation of the arm will be described. The shape and the size are slightly different between the arm 14 for the ionization needle 1 and the arm 12 for the tube 5 depending on a target to be lifted. However, the basic operation methods are the same. Thus, an example of the arm 14 for the ionization needle will be described with reference to FIGS. 11A and 11B. The arm 14 that can be driven by the transport drive unit 15 includes a support 25, two container holders 27 and 28, and a fixed point 26. The container holders 27 and 28 are fixed at the fixed point 26, and the arm can be opened and closed by the rotational motion about the fixed point 26. When the arm is closed, the sample container is joined to the arm due to the friction between the container holder of the arm and the sample container, and moved integrally. The flow of the operation is in which the arm 14 is moved to the position at which the ionization needle 1 can be caught as the arm is opened as illustrated in FIG. 11A, and the arm 14 is closed to catch the needle 1 with the container holders 27 and 28 as illustrated in FIG. 11B. In the state in which the arm 14 is joined to the ionization needle 1 (FIG. 11B), the arm 14 is moved by the drive of the drive unit 15, and the ionization needle 1 is moved together. After moved, the container holders 27 and 28 are opened, and the arm 14 can be detached from the ionization needle 1 as illustrated in FIG. 11A.

FIGS. 12A to 12D are other structural forms of the arm. In FIG. 12A, three container holders 75 are used to fix the sample container 2 of the ionization needle 1 from three directions as illustrated in the drawing. A drive unit 77 can operate and move the container holders 75 and a support 74. Thus, the ionization needle 1 can be fixed and moved. In the drawing, three container holders 75 are illustrated. However, two container holders 75 and four container holders 75 or greater may fix and move the ionization needle 1. Moreover, it may be possible that a single container holder 75 fixes and moves the sample container 2 using magnetic force. In this case, it may be fine that the material of the sample container 2 is a material attached to a magnet and the container holder is a magnet.

FIG. 12B is another structural form of the arm. Container holders 79 and 80 attached to a support 78 can be moved in the direction in parallel with the longitudinal direction of the support 78 by a drive unit 85. As a result, as illustrated in the drawing, the sample container 2 can be caught and fixed. Thus, the ionization needle 1 can be fixed and moved.

FIG. 12C is still another structural form of the arm. Container holders 86 and 87 connected to a drive unit 88 can catch and move the sample container 2 as illustrated in the drawing. The contacting portions of the container holders 86 and 87 with the sample container are in a rounded concave shape, so that the contact areas with the sample container 2 are large, and stable fixing is possible.

FIG. 12D is yet another structural form of the arm. Container holders 89 and 90 connected to a drive unit 93 can catch and move the sample container 2 as illustrated in the drawing. Thus, the ionization needle 1 can be fixed and moved. Similarly to FIG. 12C, the contacting portions of the sample holders 89 and 90 with the sample container may be in a rounded concave shape.

The sample holders may be a hard material such as a metal and a plastic. However, when a soft material having cushioning force such as sponge and rubber is provided on the portion contacting the sample container 2 in the sample container or the container holder, it may be prevented that the sample container 2 is damaged. Moreover, it is desirable to provide a slip resistance function on the contacting portions because the sample container can be firmly held. Arms using known techniques may be fine other than the arm structures described so far. The embodiment is feasible as long as such a mechanism is provided which can be moved as holding and fixing the sample container 2.

Figure 13:
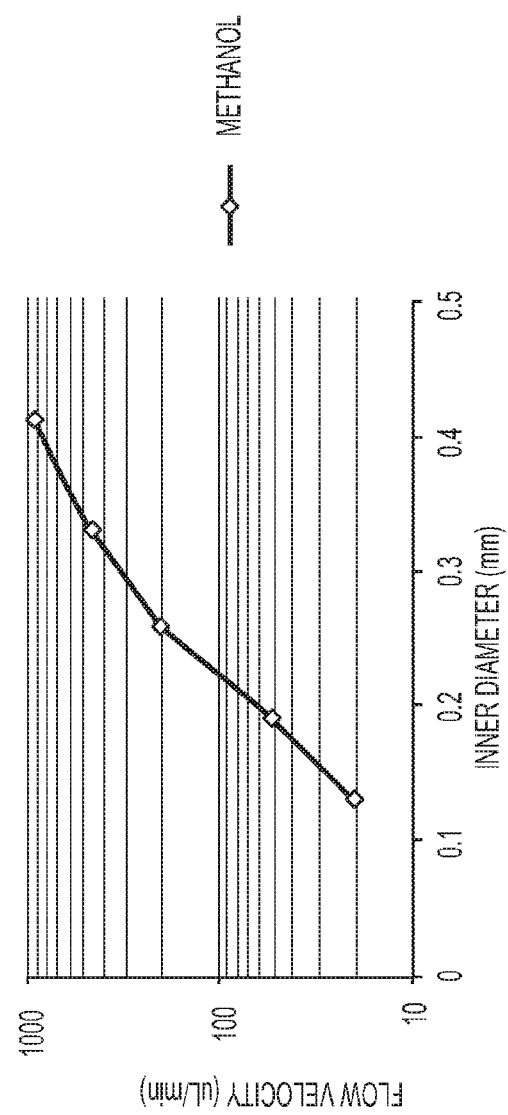
FIG. 13 is the experimental result of the inner diameter of a metal capillary and the flow velocity of liquid sample (a drop flow velocity).

In the sample supplying method according to gravity drop by gravity, the flow velocity of the liquid sample is changed depending on the inner diameter of the metal capillary and the type of a solvent. FIG. 13 is the result that the velocity of sample supplying (drop) is measured using a methanol solvent. The velocity of sample supplying was examined for the tube inner diameters of metal capillaries in a length of 25 mm in the case where solvents of 100 μL were filled in the sample container 2. The flow velocity became faster as the inner diameter of the capillary was more increased. In the methanol solvent, the velocity was changed in the range of 20 μL/min to 1,000 μL/min depending on a change in the inner diameter ranging from Φ0.1 mm to Φ0.4 mm. The flow velocity is the flow velocity often used in electrospray. It is revealed that the method according to gravity drop by gravity can cope sufficiently by the selection of the inner diameter of the metal capillary.

The detecting unit 23 may be a mass spectrometer generally often used. The mass spectrometer that is often used may include an ion trap, quadrupole mass filter, triple quadrupole mass spectrometer, time-of-flight mass spectrometer, magnetic field mass spectrometer, orbitrap mass spectrometer, Fourier-transform mass spectrometer, and Fourier-transform ion cyclotron resonance mass spectrometer, for example, and a known mass spectrometer other than the mass spectrometers. Moreover, a known detector may be fine other than mass spectrometers. For example, an electron multiplier, fluorescence detector, and charged particle detection (CAD), for example, may be fine.

In the embodiment, it is only the ionization needle 1 that contacts the sample, so that cleaning is unnecessary and a carry-over or crosstalk is greatly improved by the provision of a disposable ionization needle 1. Moreover, the clogging of the tube is also reduced. Furthermore, the supplying of a solvent is also unnecessary.

Second Embodiment

In the first embodiment, the example is described in which the ionization needle 1 is replaced for every sample. However, in the embodiment, a method will be described in which the ionization needle 1 is cleaned and reused. This is different from the first embodiment in that a cleaning step S7 is added instead of the discarding step S6. In other words, the steps according to the embodiment are performed in order of the joining step S1, the moving step S2, the sucking step S3, the moving step S4, the ionization step S5, and the cleaning step S7 (FIG. 1B). In the following, the cleaning step S7 will be described, and portions different from the first embodiment will be described.

Figure 14:
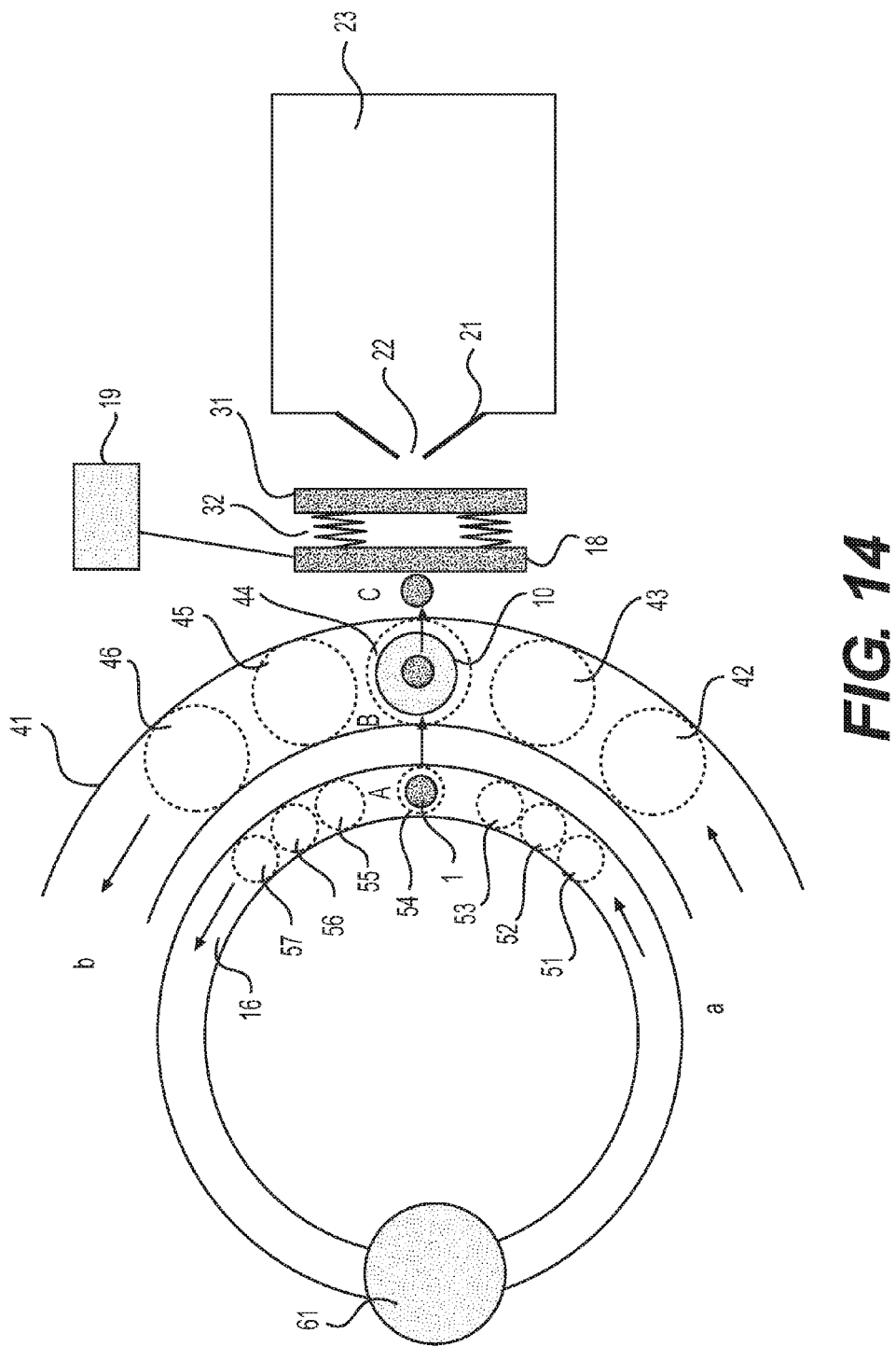
FIG. 14 is a diagram of an exemplary structure and a use form of an ion source according to a second embodiment (an overall diagram).
Figure 15B:
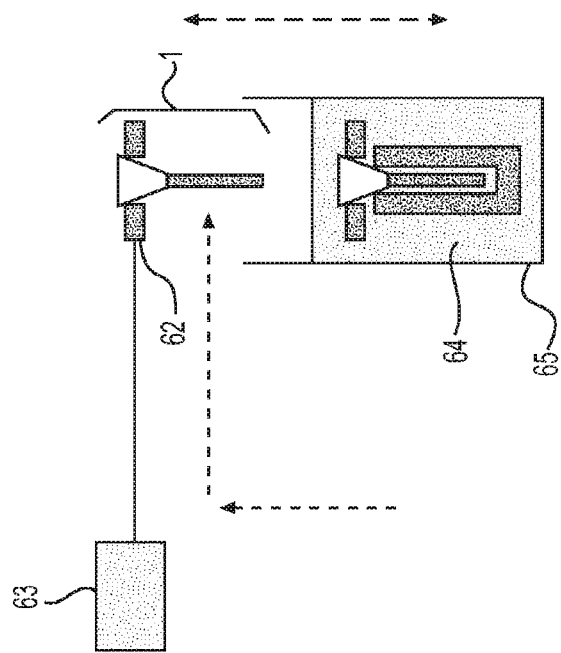
FIGS. 15A and 15B are diagrams of a cleaning method according to the second embodiment.
Figure 15A:
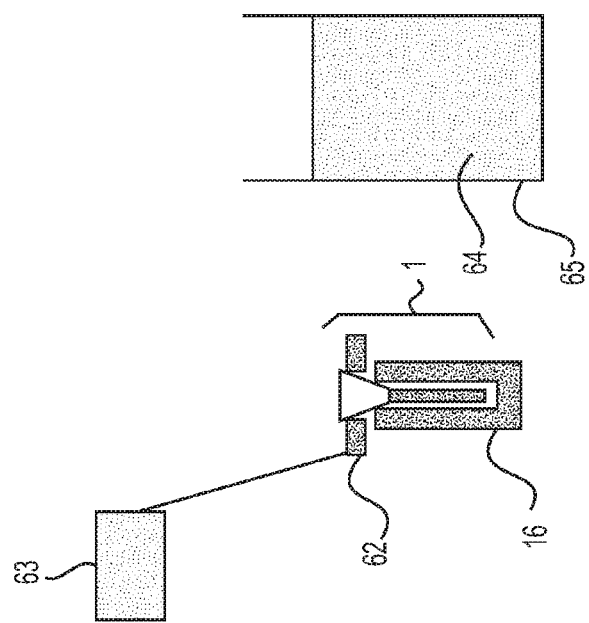

The cleaning step S7 is the step of cleaning the ionization needle 1 used for analysis and attached with a sample. After finishing the ionization step S5, the ionization needle 1 attached with the sample is moved to the position 54 similarly to the first embodiment (FIG. 14). The moved ionization needle 1 obtains the positions 55 to 57 and is moved to a cleaning position 61. At the cleaning position 61, cleaning is performed in the following flow (FIG. 15). An arm 62 is driven by a transport drive unit 63, and operates similarly to the arms 12 and 14. The arm 62 is joined to the ionization needle 1 placed on the needle storage unit 16 (FIG. 15A). After joined, the ionization needle 1 is moved above a cleaning pot 65 containing a cleaning fluid 64 by the drive unit 63 (FIG. 15B). After that, the needle 1 is lowered by the arm 62 as entirely dipped into the cleaning fluid 64. The arm 62 is moved up and down, and the ionization needle 1 is in and out of the cleaning fluid, which is repeated a plurality of times, and then the ionization needle 1 is cleaned. Generally, the ionization needle 1 is sufficiently cleaned for about a few times to a few tens times. The cleaned ionization needle 1 is returned to the needle storage unit 16, and after that, the ionization needle 1 is moved to the position 51, and can be again used for analysis (FIG. 14). The cleaning fluid 64 may include methanol, ethanol, acetonitrile, the other organic solvents, water, and a mixture of them, and may include a cleaning fluid that can clean a plastic and a metal that are often used. Since cleaning is repeated and the cleaning fluid is gradually contaminated, it is desirable to replace the cleaning fluid each time or on a regular basis. The needle is excellently cleaned by the cleaning method, so that it is possible to prevent a contaminant from being mixed, and it is possible to perform highly accurate analysis even in the measurement using a reused needle.

Figure 16B:
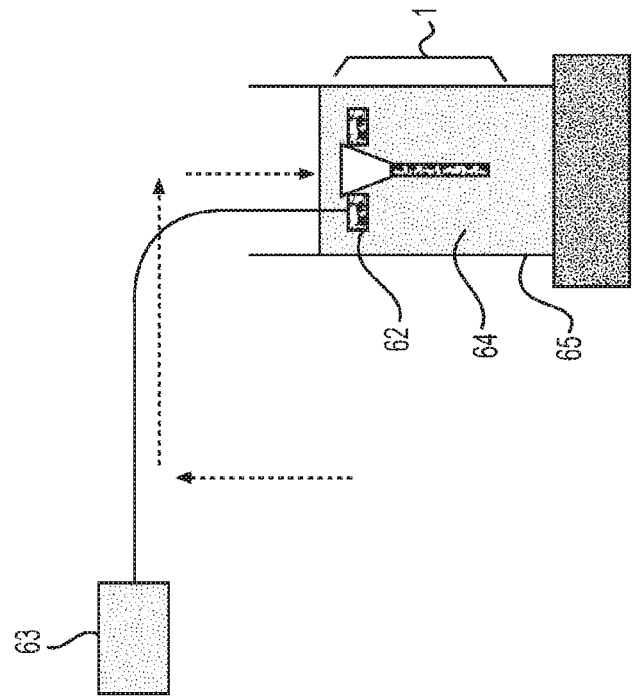
FIGS. 16A and 16B are diagrams of another cleaning method according to the second embodiment.
Figure 16A:
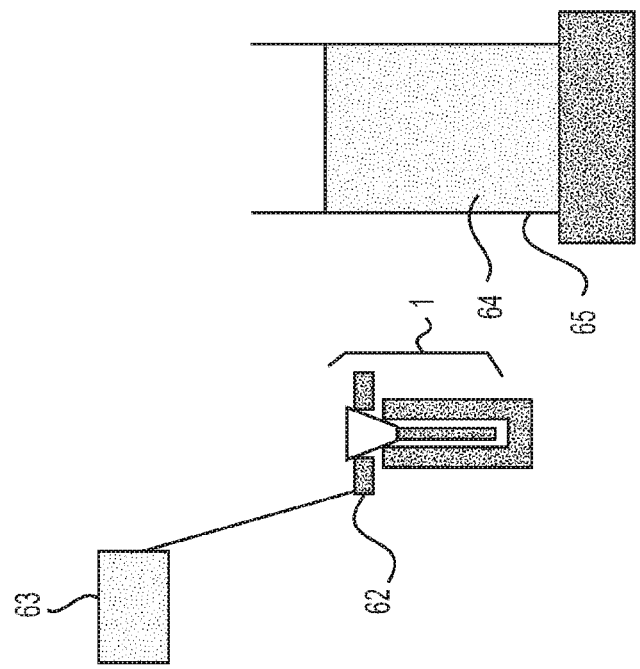

In the following, embodiments of other cleaning methods are shown. It is similar in any embodiments as in the foregoing embodiments that after finishing the ionization step S5, and the ionization needle 1 attached with a sample is moved to the cleaning position 61. An embodiment illustrated in FIGS. 16A and 16B is a cleaning method using ultrasonic waves. At the cleaning position, the arm 62 that can be driven by the drive unit 63 is used to dip the ionization needle 1 into the cleaning fluid 64 (FIG. 16A). After the ionization needle 1 is entirely dipped into the cleaning fluid, an ultrasonic cleaner 66 is used to vibrate the cleaning fluid 64 for a few seconds to a few minutes for ultrasonic cleaning (FIG. 16B).

Figure 17B:
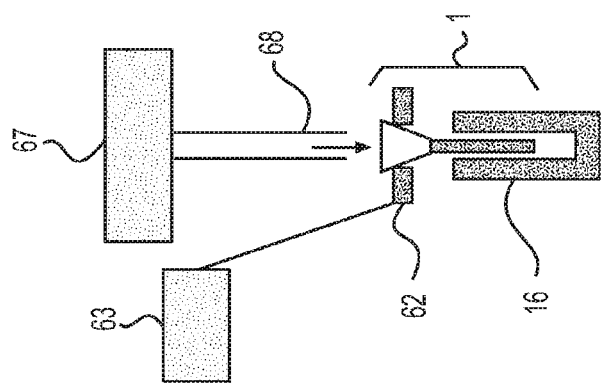
FIGS. 17A and 17B are diagrams of still another cleaning method according to the second embodiment.
Figure 17A:
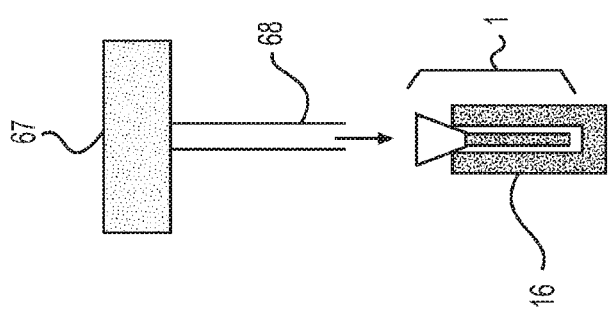

FIG. 17A is an embodiment of another cleaning method. The embodiment is a method using a high pressure cleaner. A high pressure cleaner 67 is a device in which a cleaning fluid is issued from the tip end of a cleaning tube 68 at a high pressure for cleaning the ionization needle 1. At the cleaning position 61, the ionization needle 1 is cleaned as placed on the needle storage unit 16 (FIG. 17A). The cleaning fluid issued by the high pressure cleaner 67 is blown to the ionization needle 1, and the ionization needle 1 is cleaned. Both of the inner wall and the outer wall of the ionization needle 1 are cleaned.

FIG. 17B is still another embodiment using a high pressure cleaner. The difference from FIG. 17A is in that the ionization needle 1 is lifted using the arm 62 that can be operated by the transport drive unit 63 and is floated above the needle storage unit 16. In this method, the outer wall of the ionization needle 1 and the outer wall of the metal capillary 3 can be more excellently cleaned, and the needle storage unit 16 can be excellently cleaned as well.

Figures 18A, 18B:
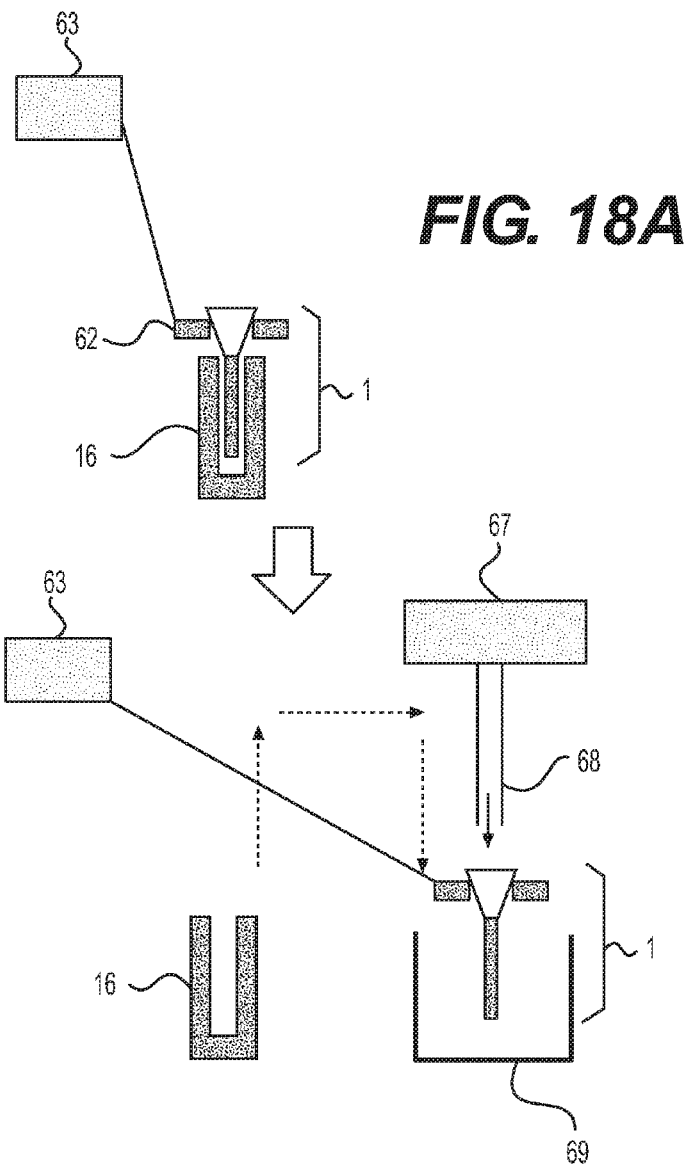
FIGS. 18A and 18B are diagrams of yet another cleaning method according to the second embodiment.

FIGS. 18A and 18B are yet another embodiment using a high pressure cleaner. After the ionization needle 1 is moved above a container 69 using the arm 62, cleaning is performed using the high pressure cleaner 67 (FIG. 18B). The container 69 is a saucer for a sprayed cleaning fluid, and the cleaning fluid used for cleaning is stored in the container 69 for recovery. The used cleaning fluid is discarded on a regular basis before the container 69 is filled. It is desirable to also clean the needle storage unit 16 simultaneously using the high pressure cleaner 67.

It is more desirable to clean the voltage application contact terminal 18 (FIGS. 8 and 14) and the other locations contaminated with a sample using the high pressure cleaner.

FIGS. 19A and 19B are an embodiment of still yet another cleaning method. The embodiment is a method using the syringe 6 and the syringe pump 8 similar to the method for sucking a sample, in which a cleaning fluid is repeatedly sucked and discharged to clean the ionization needle 1. Similarly to the first embodiment, the tube 5 is joined to the ionization needle 1 using the arm 12 movable by the drive unit 13 (FIG. 19A). After that, the ionization needle 1 is moved above the cleaning pot 65 containing the cleaning fluid 64, and the tip end 4 of the ionization needle 1 is dipped into the cleaning fluid 64 (FIG. 19B). After that, similarly to the method for introducing the liquid sample into the sample container 2, the pressure of the inside of the sample container 2 is reduced by pulling the syringe pump 8 upwardly, and the cleaning fluid 64 enters the sample container 2. The syringe pump is stopped when the sample container 2 is nearly filled with the cleaning fluid. Subsequently, in the inverse manner, the cleaning fluid 64 is discharged to the cleaning pot 65 by pushing the syringe 6 downwardly using the syringe pump 8. The operation of the syringe pump is repeated a few times for cleaning the ionization needle 1. It may be fine that in discharging the cleaning fluid 64 contained in the sample container 2, the cleaning fluid 64 is discharged to a separate waste pot, not discharged to the cleaning pot 65 containing the cleaning fluid 64. This is preferable because an unused cleaning fluid 64 contained in the pot 65 is not contaminated. It may be possible that the cleaning fluid is sucked to the tube and the tube is also cleaned simultaneously.

The foregoing cleaning methods are merely examples, and cleaning methods using the other known techniques may be fine.

Third Embodiment

In this embodiment, a method according to such a structure will be described in which a high voltage application function is further provided to the foregoing moving arm. The embodiment is a method in which the ionization needle 1 is moved using an arm 71 controlled by a transport drive unit 72, and a high voltage is applied from a high voltage power supply 73 through the arm 71. The surface of the arm 71 is made of a conductive material such as metal plating, and a voltage is applied to the metal capillary 3 of the ionization needle 1 through the conductive material. A flow of basic analysis is similar to the first embodiment, including the joining step S1, the moving step S2, the sucking step S3, the moving step S4, the ionization step S5, and the discarding step S6 (FIG. 1A). Points different from the first embodiment will be mainly described.

The joining step S1 is the step of joining the tube 5 to the sample container 2 of the ionization needle 1 (FIG. 20). The difference from the first embodiment is in that the arm is not joined to the ionization needle 1. However, the ionization needle 1 is fixed to the needle storage unit 16, so that joining can be performed smoothly. The other configurations are similar to the first embodiment.

Figure 21:
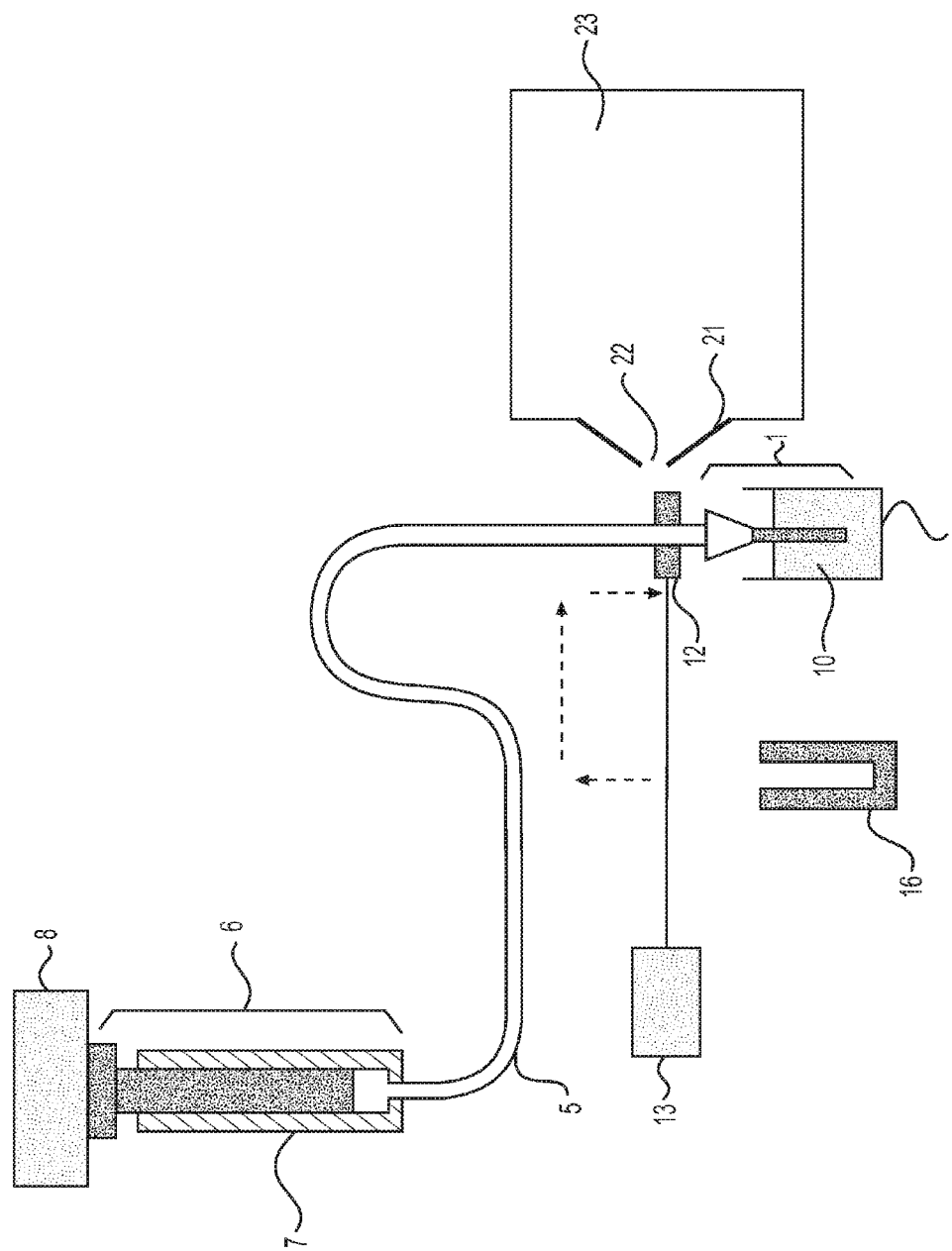
FIG. 21 is a diagram of an exemplary structure and a use form of the ion source according to the third embodiment (a moving step).

The moving step S2 is the step of moving the needle tip end 4 of the ionization needle 1 into the liquid sample 10 in order to suck the sample (FIG. 21). The ionization needle 1 is moved using the arm 12 connected to the transport drive unit 13. The ionization needle 1 is light weight, so that the tube 5 as well as the ionization needle 1 can be moved using only the arm 12 connected to the tube 5. The other configurations are similar to the first embodiment.

Figure 22:
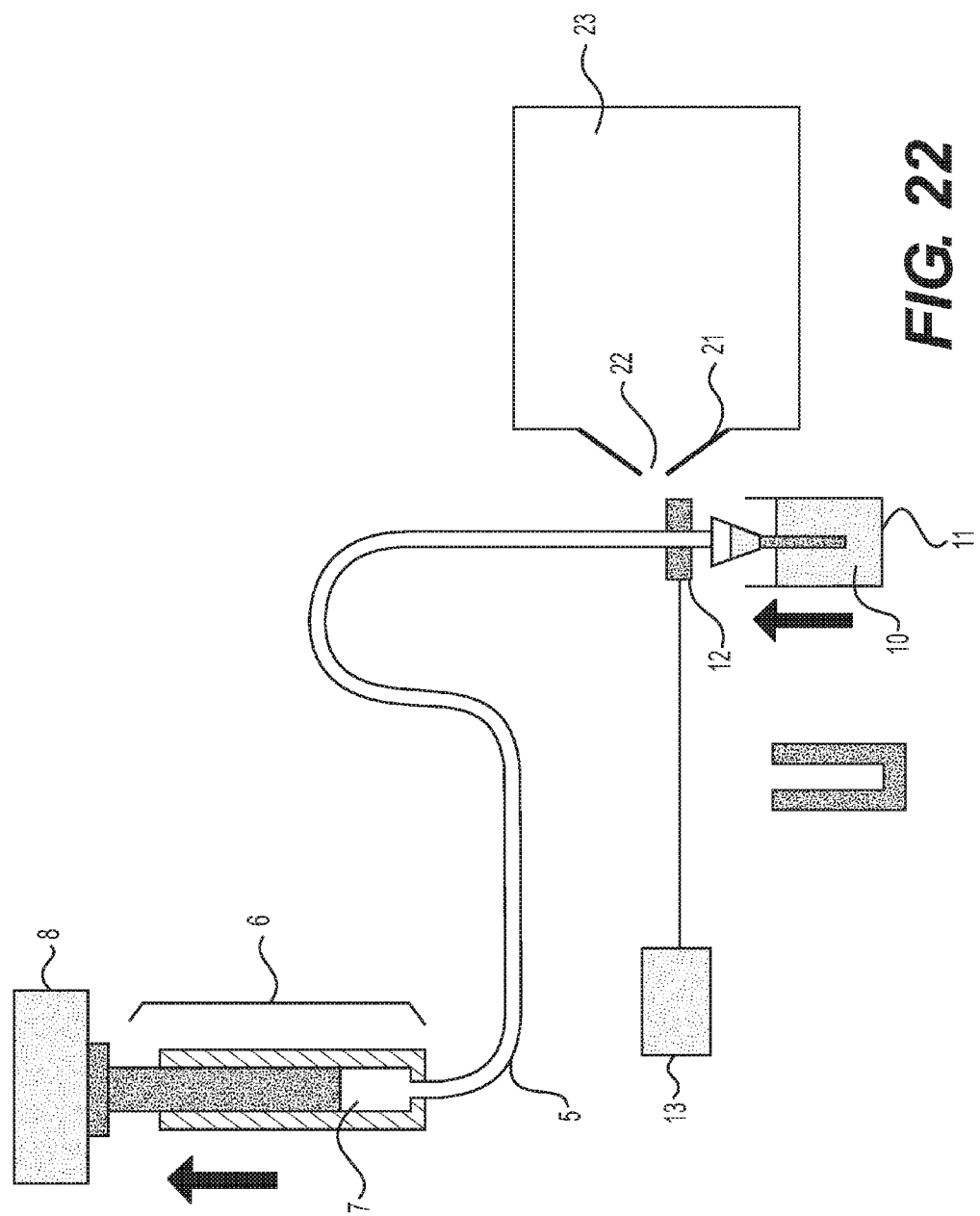
FIG. 22 is a diagram of an exemplary structure and a use form of the ion source according to the third embodiment (a sucking step).

The sucking step is omitted because the step is similar to the first embodiment (FIG. 22).

Figure 23:
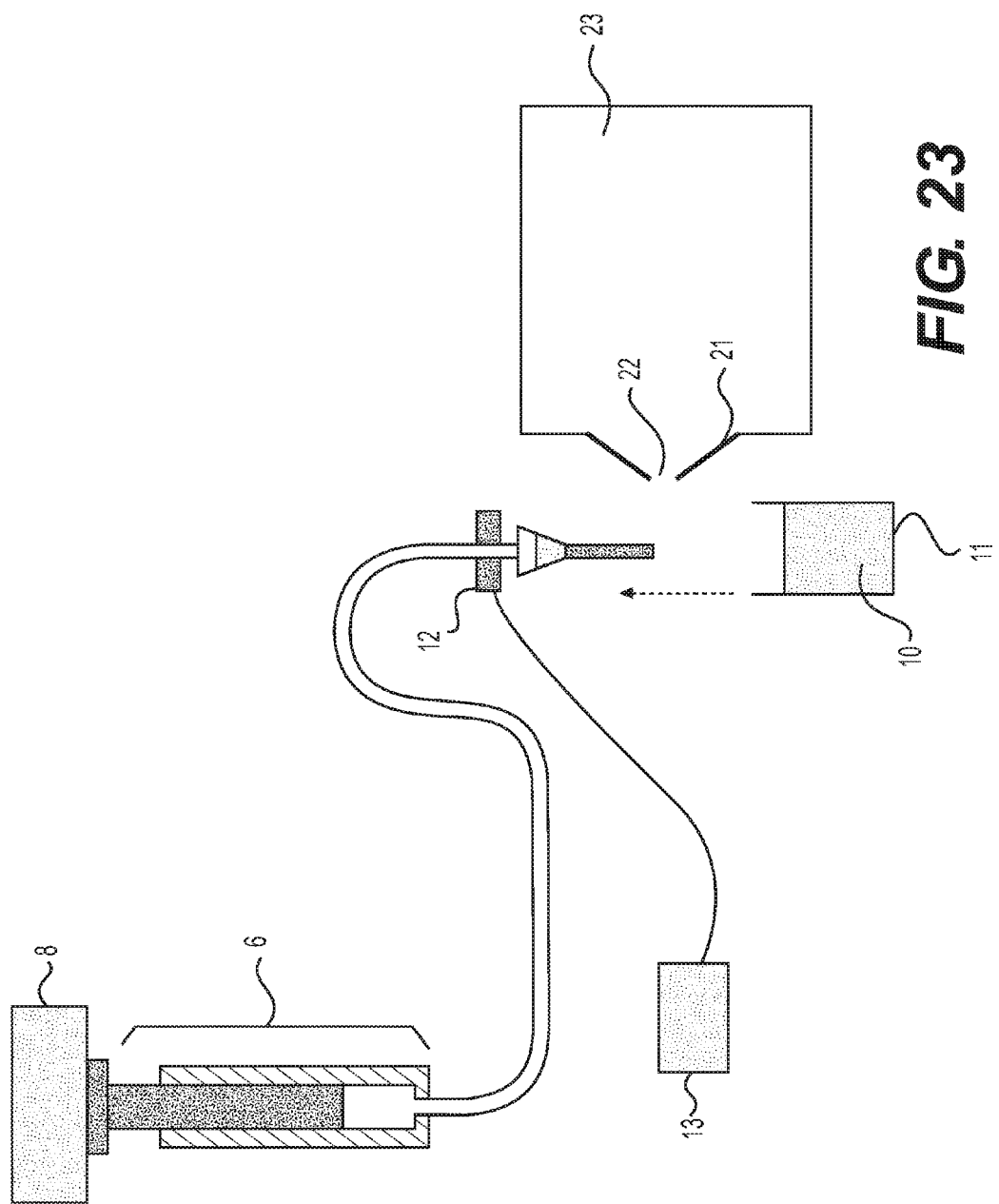
FIG. 23 is a diagram of an exemplary structure and a use form of the ion source according to the third embodiment (a moving step).

The moving step S4 is the step of moving the ionization needle 1 to the position at which ionization is performed in the mass spectrometer (FIG. 23). The ionization needle 1 in which the liquid sample 10 is filled in the sample container 2 is moved upwardly by the drive unit 13 that drives the arm 12, and the needle tip end 4 is moved to near the pore 22 of the counter electrode 21, which is the inlet port of the mass spectrometer. At this time, it may be fine that when the ionization needle 1 is detached from the tube 5 due to the weight of a liquid sample, such an arm is provided to hold the ionization needle 1.

Figure 24:
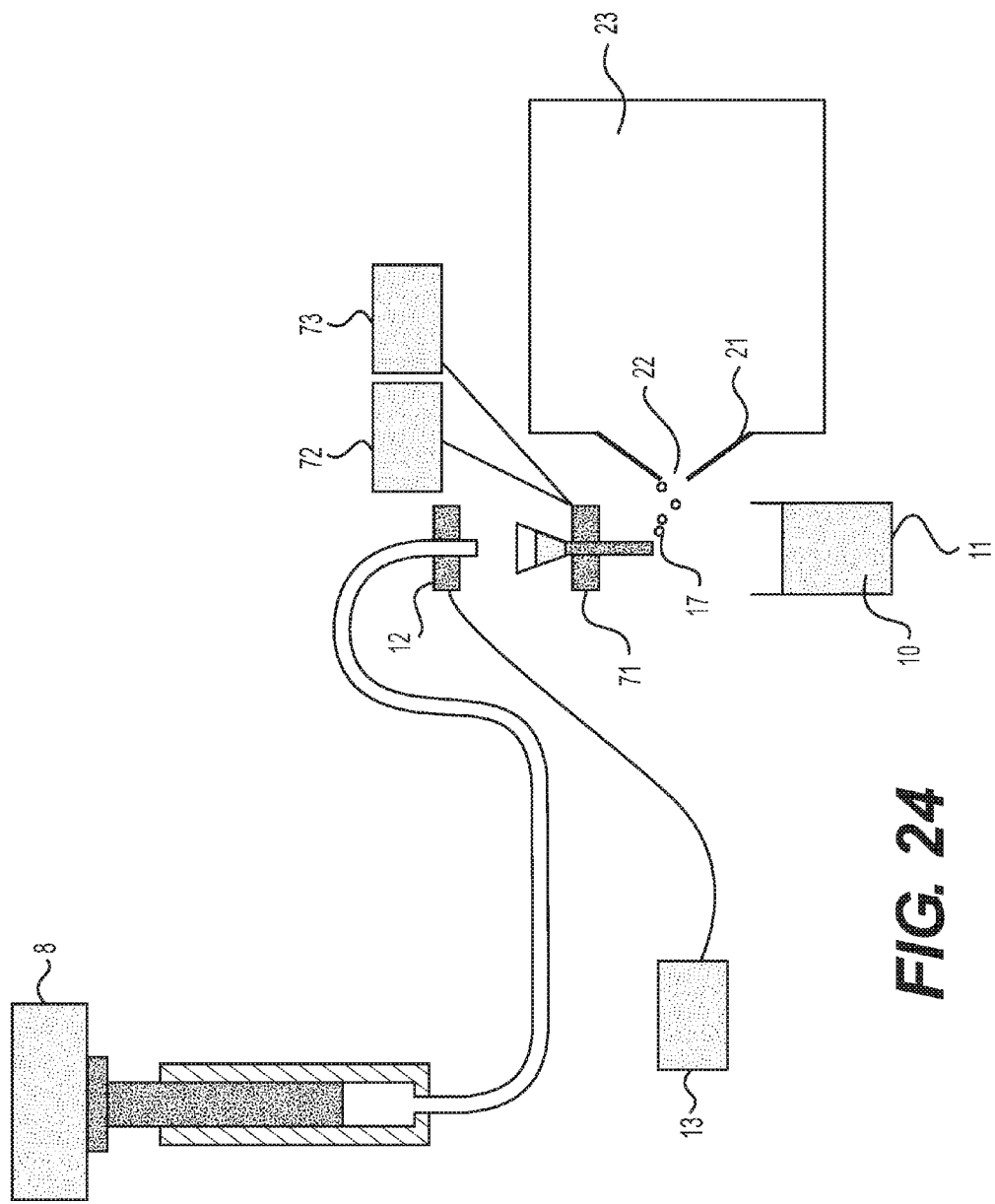
FIG. 24 is a diagram of an exemplary structure and a use form of the ion source according to the third embodiment (an ionization step).

The ionization step S5 is the step in which a voltage is applied to the metal capillary 3 of the ionization needle 1 and ionization is performed when sample supplying is started (FIG. 24). The arm 71 connected to the transport drive unit 72 is joined to the metal capillary 3 of the ionization needle 1, and serves to hold and fix the position of the ionization needle 1. The method for joining the arm 71 to the ionization needle 1 is performed by a method similar to the description in FIG. 11. First, the voltage of the high voltage power supply 73 is applied to the metal capillary 3 of the ionization needle 1 through the surface of the arm 71. In this state, the tube 5 is detached from the ionization needle 1 using the arm 12 and the arm 71. For example, it is fine that the arm 71 is fixed and the arm 12 is moved upwardly. Sample supplying is started at the same time when the tube 5 is detached, and ions 17 generated by ionization are introduced from the pore 22 into the detecting unit for analysis.

Figure 25:
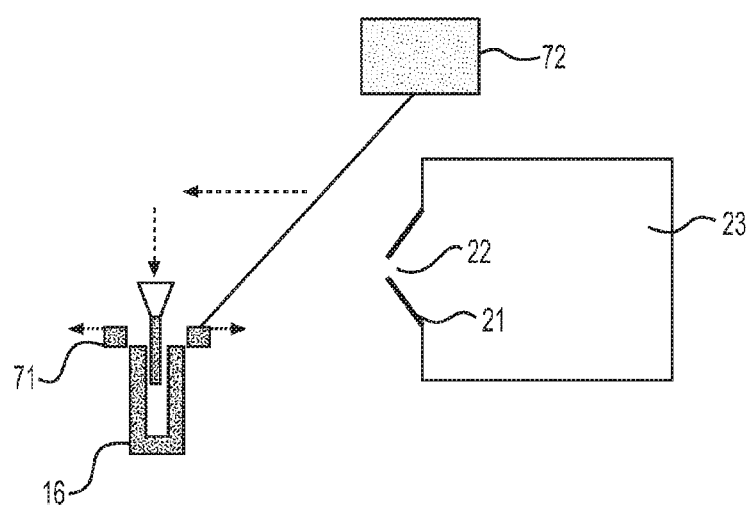
FIG. 25 is a diagram of an exemplary structure and a use form of the ion source according to the third embodiment (a discarding step).

The discarding step S6 is the step of discarding the used ionization needle 1 after finishing measurement (FIG. 25). The used ionization needle 1 is moved above the needle storage unit 16 using the transport drive unit 72 that drives the arm 71. After the ionization needle 1 is moved, the arm 71 is opened by the drive unit 72, and the ionization needle 1 is returned to the needle storage unit 16. After that, the ionization needle 1 may be discarded, or may be cleaned and reused as described in the second embodiment.

FIG. 26A is the structure of another contact terminal for applying a voltage. The difference from the first embodiment is in that a single spring is provided between the fixing unit 31 and the contact terminal 18 and one end of the contact terminal 18 is directly fixed. Similarly to the first embodiment, the metal capillary 3 of the ionization needle 1 contacts the contact terminal 18, and a voltage is applied.

FIG. 26B is the structure of still another contact terminal for applying a voltage. This is a method in which a contact terminal 33 connected to the high voltage power supply 19 is in a V-shaped structure and the metal capillary 3 enters and contacts the contact terminal 33.

Figure 26C:
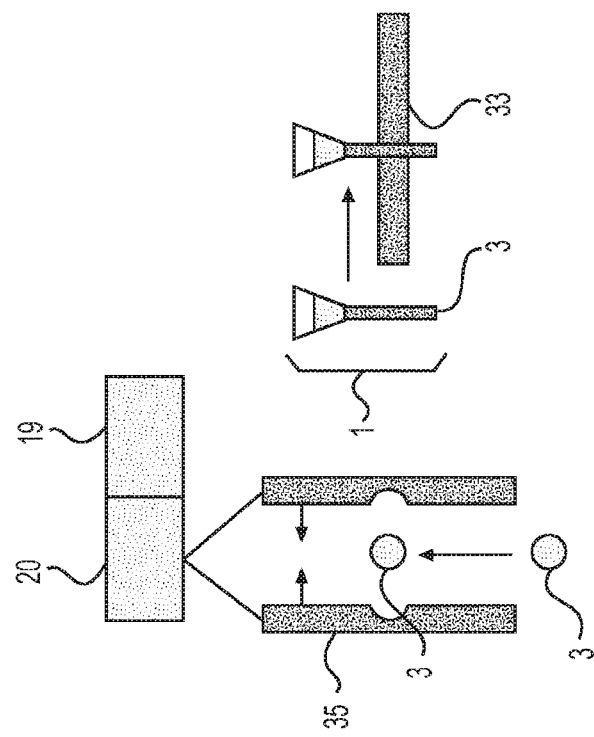
FIGS. 26(C) and 26(D) are diagrams of still another method for applying a voltage.

FIG. 26C is the structure of yet another contact terminal for applying a voltage. Two contact terminals 34 are moved by a drive unit 20 to hold the metal capillary 3 of the ionization needle 1 between the contact terminals 34. Moreover, a voltage is applied to the metal capillary 3 by the high voltage power supply 19 through the contact terminals 34.

Figure 26D:
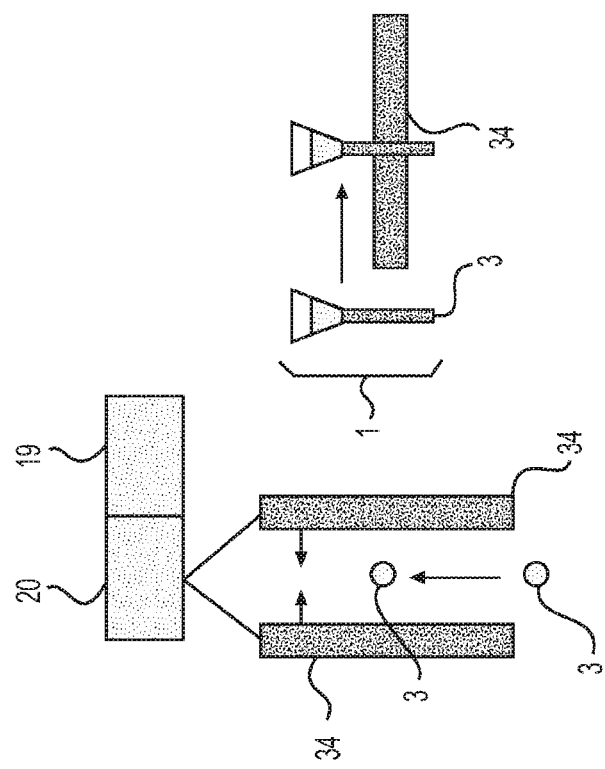

FIG. 26D is the structure of still yet another contact terminal for applying a voltage. A rounded concave cavity is provided on two contact terminals 35, and the contact areas with the metal capillary 3 are increased for easy contact. The other configurations are similar to the example in FIG. 26C.

Moreover, for another embodiment, a method will be described in which only the arm 71 and the drive unit 72 are used. In the foregoing embodiments, the arm 12 and the drive unit 13 are used. However, this embodiment is a method in which the arm 12 and the drive unit 13 are not used, and the arm 71 is joined to the metal capillary 3 of the ionization needle 1 in the joining step in FIG. 20. It is possible to directly catch the metal capillary 3 with the arm 71 when the structure of the needle storage unit 16 is devised. In other words, it may be fine that the wall of the needle storage unit 16 is eliminated only around the metal capillary 3. In this method, the structure is simple because a single arm is provided.

The method for applying a voltage described in the embodiment can be used also in the other embodiments.

Fourth Embodiment

In the ionization step S5 according to the embodiments so far, the tube 5 is moved upwardly (in the positive Z-axis direction side) when the tube 5 is detached from the ionization needle 1 in order to start ionization. However, at this time, it is likely that the liquid sample is sucked above because the pressure of the inside of the sample container 2 is reduced, and as a result, the tip end 4 of the metal capillary 3 includes a slight amount of air. As a result, in the case where the inner diameter of the metal capillary is small as a diameter of $\Phi 0.1$ mm or $\Phi 0.2$ mm, it is not sometimes enabled to supply a liquid according to a method for supplying a liquid sample due to gravity drop. Thus, such a method is disclosed in which air is prevented from entering the tip end 4 of the ionization needle 1 and a liquid is supplied.

A first embodiment is a method in which the tube 5 is detached while applying a pressure using the piston 7 of the syringe 6. In other words, it is a method in which in the ionization step S5 according to the first embodiment (FIG. 6), the tube 5 is detached while pushing the piston 7 downwardly using the syringe pump 8 in the drawing (in the negative Z-axis direction side). At this time, it is desirable to prevent air from entering the metal capillary 3 from the tip end thereof when a pressure is applied in such a manner that a slight amount of the liquid sample flows out of the tip end 4 of the metal capillary 3.

Figure 27:
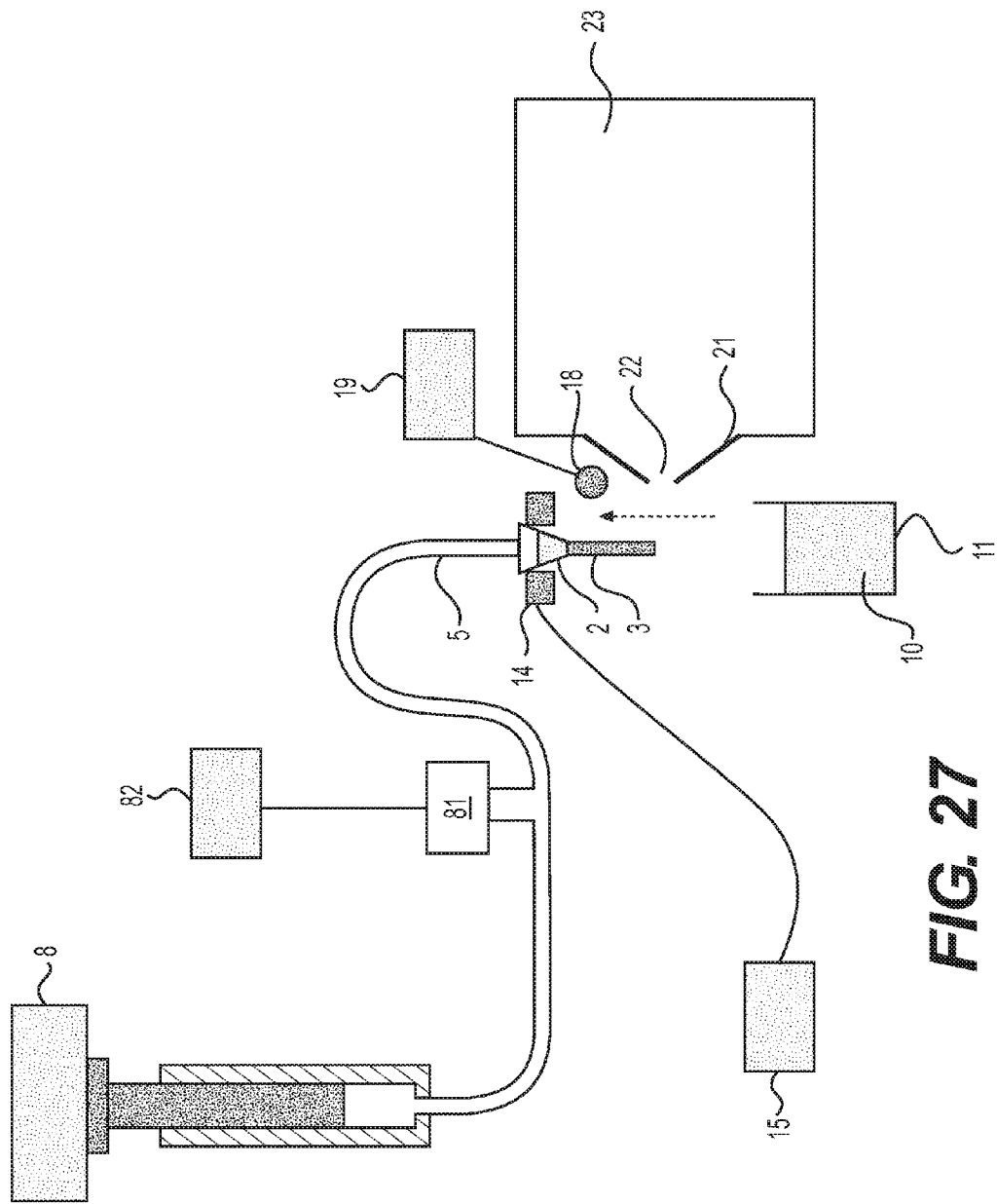
FIG. 27 is a diagram of an exemplary structure and a use form of an ion source according to a fourth embodiment and a fifth embodiment.

Another embodiment is a method in which a valve is provided in the midway point of the tube 5 and the valve is opened. As illustrated in FIG. 27, such a structure is formed in which a valve 81 is provided in the midway point of the tube 5 and the valve 81 can be opened and closed using a controller 82. The valve 81 is opened and released, the inside of the tube 5 is opened to the atmosphere, and the pressure is set to an atmospheric pressure. When the tube 5 is detached from the ionization needle 1 by this operation, it is possible to prevent events that the inside of the sample container 2 is not reduced pressure, the liquid sample 10 contained in the sample container 2 is not sucked together with lifting the tube, and air enters the tip end of the metal capillary. An example that the valve is taken is described. However, any methods may be possible as long as the methods are methods for setting the pressure of the inside of the tube 5 or the inside of the sample container 2 to an atmospheric pressure other than the method using the valve.

Moreover, still another embodiment is a method in which the tube 5 is slid in the X-direction (in the lateral direction)

and the tube 5 is detached from the sample container 2, which is not a method in which the tube 5 is detached by moving the tube 5 in the Z-direction (in the vertical direction) the same as the metal capillary. The tube 5 is slid, so that the pressure of the inside of the sample container 2 is not reduced, and the inside is opened to the atmosphere, and it is possible to prevent air from entering through the tip end of the metal capillary. It may be fine that a sliding type joining method is used, which is feasible by a known technique, for this method.

The methods described in the embodiment can be used also in the other embodiments.

Fifth Embodiment

An embodiment of a method for adjusting the liquid flow velocity of the supplying of the liquid sample in the ionization step will be described. In the first embodiment, the method is described in which the flow velocity of liquid sample is changed by varying the inner diameter of the metal capillary 3 of the ionization needle 1. However, in the embodiment, another method will be described.

The embodiment is illustrated in FIG. 27. In the embodiment, the supplying of the liquid sample and ionization are performed without detaching the tube 5 from the sample container 2. The control of the flow velocity of the liquid is adjusted by opening and closing the valve 81. When the valve is closed, the liquid is not dripped, and the flow velocity becomes zero. On the other hand, the valve is fully opened and released, the liquid flows at the flow velocity that is determined by the inner diameter of the metal capillary and the viscosity of the solvent as in FIG. 13. The flow velocity in the opening and closing of the valve can be adjusted by a ratio between the opening and closing of the valve. In other words, the opening and closing of the valve are adjusted, so that it is possible to set the velocity of sample supplying to a given flow velocity. The valve 81 is connected to the controller 82, and the flow velocity can also be changed individually for samples. Moreover, the controller 82 is connected to a personal computer, for example, and automatic control is also possible in a predetermined manner.

Figure 28:
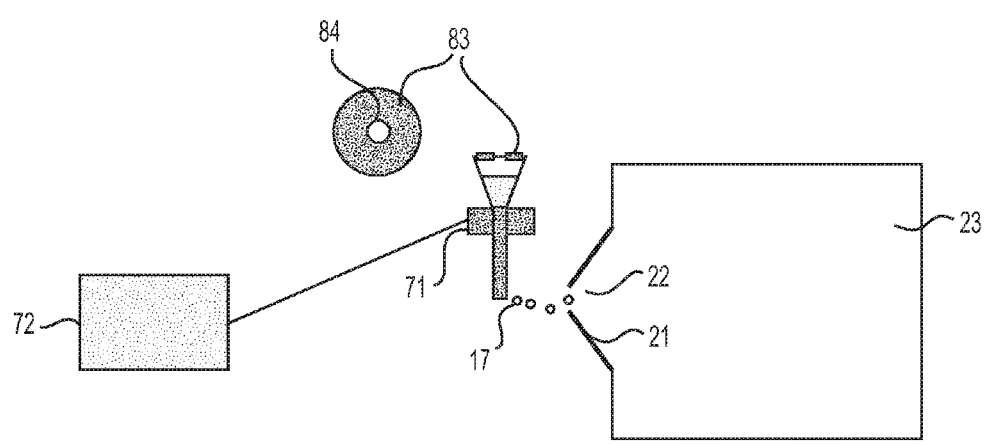
FIG. 28 is a diagram of an exemplary structure and a use form of the ion source according to the fifth embodiment.

Furthermore, FIG. 28 is another embodiment. The embodiment is a method in which in the ionization step, the tube 5 is detached, and the upper part of the sample container 2 is covered with a lid 83 having a hole 84. The flow velocity of liquid sample can be adjusted depending on the area of the hole 84. For example, the flow velocity becomes greater as the area of the hole 84 is greater, whereas the flow velocity becomes smaller as the area of the hole is smaller. It may be fine to provide a hole having a diameter ranging from about a few 100 μm to a few 10 mm. Such a mechanism may be provided that a plurality of lids having various hole sizes is prepared and the lid is automatically covered according to the flow velocity set by a personal computer.

Sixth Embodiment

Figure 29:
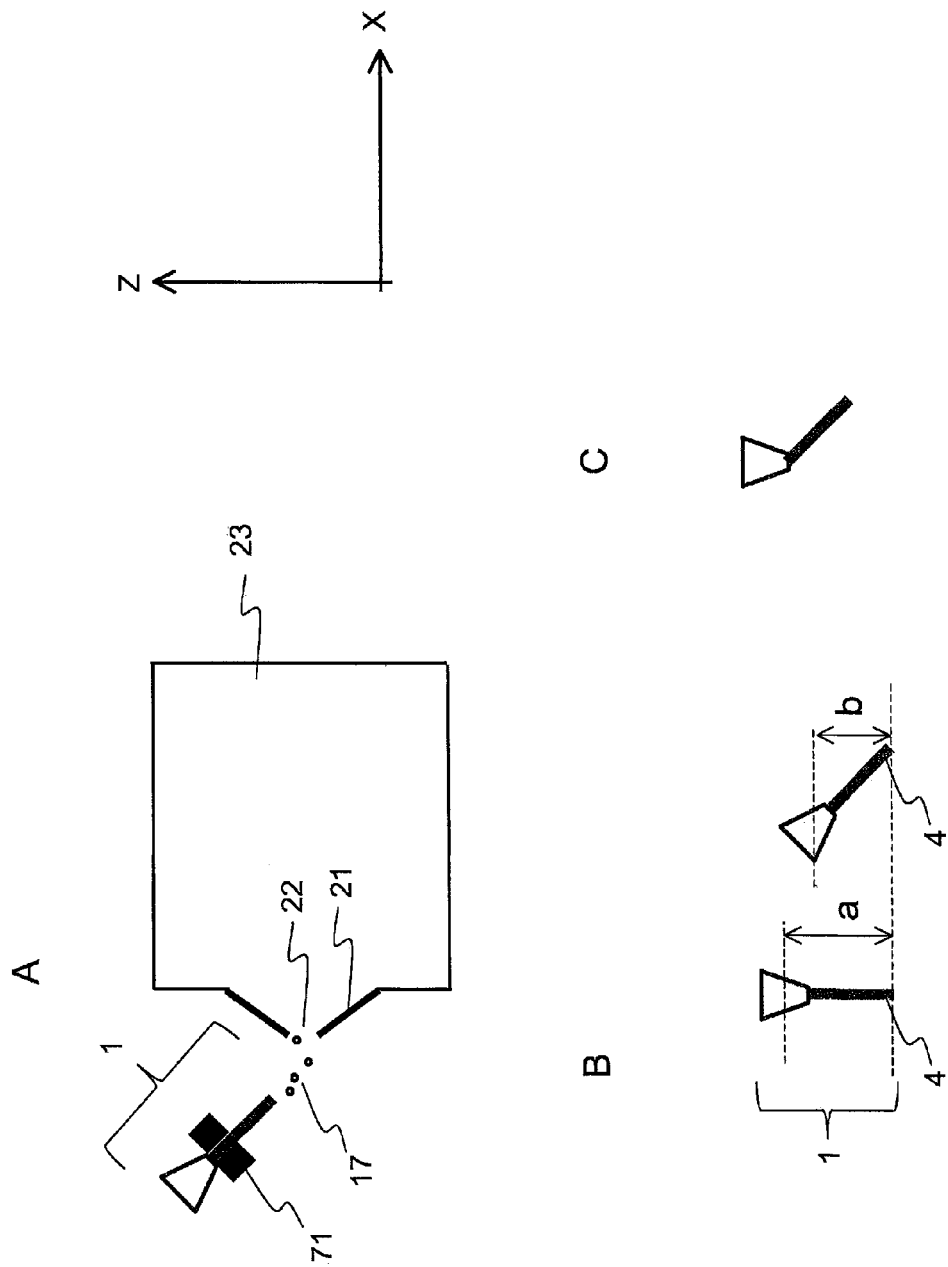
FIGS. 29A to 29C are diagrams of an exemplary structure and a use form of an ion source according to a sixth embodiment.

In both of the first embodiment and the result of the flow velocity of liquid sample in FIG. 13, the ionization needle 1 is disposed in parallel with the Z-axis, which is in parallel with the direction of gravity. In this embodiment, a method will be described for another method for adjusting the flow velocity of liquid sample in which the angle of the ionization needle 1 is tilted to adjust the flow velocity of liquid sample. FIG. 29A is an example that the ionization needle 1 is tilted at an angle of 45 degrees from the Z-axis direction. The ionization needle 1 is tilted at an angle of 45 degrees, and the velocity of sample supplying is reduced as compared with the case illustrated in FIG. 13. It is assumed that this is because the distance (the height) between the liquid surface and the needle tip end 4 in the Z-axis direction is reduced from distance a to distance b by tilting the needle and the flow velocity is reduced (FIG. 29B). Thus, the velocity of sample supplying can be freely adjusted by adjusting the angle of the needle. In this embodiment, the example is described in which the needle is tilted at an angle of 45 degrees. However, the flow velocity can be adjusted by appropriately adjusting various angles to achieve a predetermined flow velocity. Moreover, it is necessary to take measures when the needle is tilted that a part of the top face is covered, or that the structure of the sample container 2 is devised and the sample is not fallen off in order not to fall the sample off from the upper part of the sample container 2. Alternatively, it may be fine that the sample container 2 is disposed in parallel with the Z-axis and such a needle is provided that only the needle 1 is tilted (FIG. 29C).

Seventh Embodiment

Figure 30:
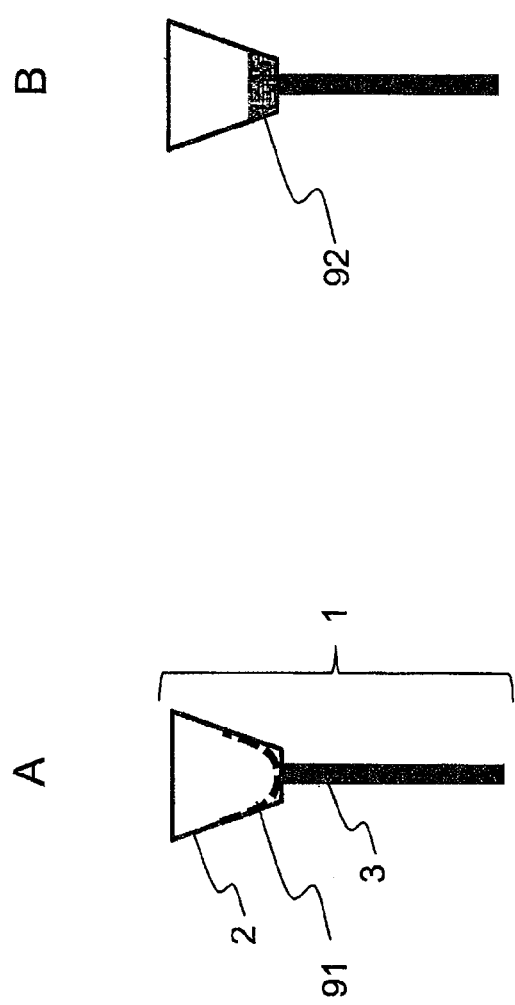
FIGS. 30A and 30B are diagrams of an ionization needle according to a seventh embodiment.

Another embodiment of a method for adjusting the velocity of sample supplying will be described. As illustrated in FIGS. 30A and 30B, the embodiment is a method in which a porous material such as paper is disposed on the bottom of the sample container 2 on the inner side. The porous material includes gaps in the inside of the material, so that a liquid sample can be passed through the porous material. However, the porous materials function as a resistance to the flow of the liquid, so that the liquid is not easily passed, and as a result, the flow velocity of liquid sample can be slowed. FIG. 30A is an example that a porous material 91 made of paper, cloth, or the like is disposed. FIG. 30B is an example that a porous material 92 made of wood, plastic, sponge, or the like is disposed. The porous material is disposed, so that it is possible to slow the flow velocity of liquid sample by drop. Moreover, the velocity of sample supplying can be adjusted by the amount and thickness of the porous material. This is similarly feasible even using other known porous materials.

Eighth Embodiment

Figure 31:
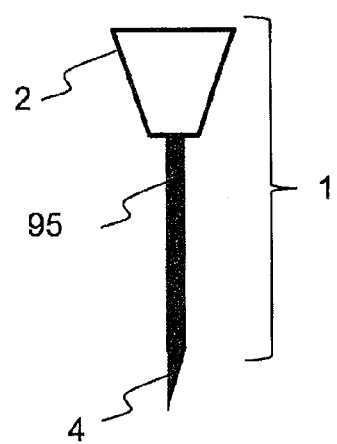
FIG. 31 is a diagram of an ionization needle according to an eighth embodiment.

This embodiment is an example that the tip end 4 of a metal capillary 95 of the ionization needle 1 is painted. FIG. 31 is an example of the embodiment. The tip end is pointed in the diameter ranging from about a few μm to a few 100 μm, for example, as an injection needle often used. The liquid is sprayed from the tip end 4 through the inside of the metal capillary 95 similarly to the examples so far. The tip end is pointed, so that it is likely that ionization becomes stable because of the stability of discharge and that local nano-spray can be achieved at the tip end part.

Ninth Embodiment

For another embodiment, such a method will be described in which a sample is sucked by vertically moving the ionization needle 1 as well as the sample pot as in the foregoing embodiments. The embodiment will be described as an exemplary application of the third embodiment. The steps of the measurement operation include the joining step S1, the moving step S2, the sucking step S3, the moving step S4, the ionization step S5, and the discarding step S6, and are the same as the first embodiment (FIG. 1A). The discarding step S6 may be replaced by the cleaning step S7.

The joining step S1 is omitted because the step is similar to the first and the third embodiments.

The moving step S2 is different from the embodiments so far, and is the step of moving both of the ionization needle 1 and the sample pot 11. The ionization needle 1 is moved at the ionization position in the mass spectrometer. After that, the sample pot 11 is moved to the position of the needle 1. The sample pot 11 containing the liquid sample 10 is placed on a stage 96, the stage 96 is reciprocated in the Z-axis direction by a controller 97, and thus the sample pot 11 is also simultaneously reciprocated. The sample pot 11 is moved in the positive Z-axis direction so as to dip the tip end 4 of the needle in the liquid sample 10 (from FIG. 32A to FIG. 32B). It may be fine that one sample pot 11 is picked up from the sample pot storage unit 41 in which a plurality of samples is arranged (FIG. 8) and is placed on the stage, 96.

The sucking step S3 is omitted because the step is similar to the first and the third embodiments.

Figure 32:
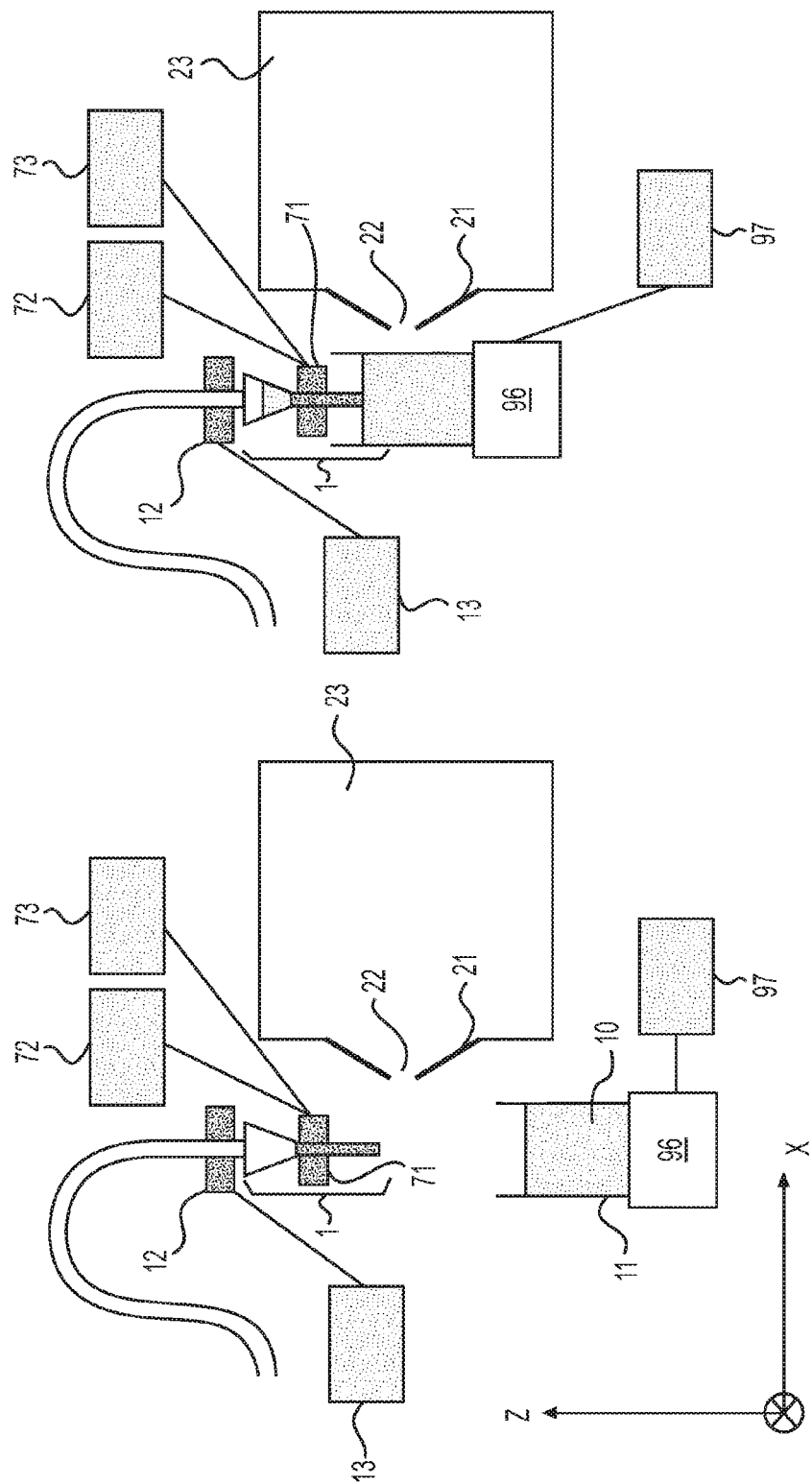
FIGS. 32A and 32B are diagrams of an exemplary structure and a use form of a ninth embodiment (a moving step).

The moving step S4 is the step of moving the sample pot 11. The stage 96 is moved in the negative Z-axis direction, and the sample pot is returned to the original position as illustrated in FIG. 32A. After that, the used sample pot is discarded or is moved to the sample pot storage unit 41.

The ionization step S5 and the discarding step S6 are omitted because the steps are similar to the first and the third embodiments.

Tenth Embodiment

The problems common in publicly known PTL1 to PTL3 are in that the improvement of the throughput of analysis is not enabled because the subsequent measurement sample is not sucked and not supplemented during ionization. In the following, the common problems and the specific problems will be individually described for PTL1 to PTL3.

PTL 1 has a problem in that in the process of ionization, since the sample suction-and-transport pipetter and the chip are joined to the silicon substrate that is the ionization needle, it is not enabled to suck the subsequent sample and to improve the throughput of analysis. Moreover, another problem is in that since the tube inner diameter of the ionization needle is a diameter of about a few μm and foreign particles and samples are apt to be clogged. More specifically, it is not enabled to use a sample from which foreign particles are not removed excellently in pre-processing, that is, a sample subjected to simple pre-processing. Furthermore, although nano-spray at a small flow velocity of liquid sample is feasible because a nebulizer gas for promoting ionization or the like is not used, it is predicted that sensitivity is degraded when the flow velocity of liquid sample becomes greater.

In PTL 2, since it is not enabled to physically suck and supply a sample to the needle in the process of ionization, ionization is performed intermittently and discretely, and it is not enabled to improve the throughput of analysis. Moreover, another problem is in that since the probe is reciprocated at high speed, there is a concern that ionization becomes unstable and ionic strength does not become stable.

PTL 3 has a problem in that since the sample suction-and-transport pipetter is joined to the ionization needle in the process of ionization, it is not enabled to suck the subsequent sample and to improve the throughput of analysis. Moreover, PTL 3 has a problem in that since the sample is also attached to the outer wall of the ionization needle when the sample is sucked, the inside of the gas spray tube is contaminated in inserting the ionization needle into the gas spray tube (the nebulizer gas tube) of the ionization unit after that. As a result, it is also likely that a carry-over is taken place and quantitative precision is degraded.

In the embodiment and embodiments later, there are disclosed a method and a configuration that solve a problem in that the throughput of analysis is reduced because the subsequent sample is not sucked during ionization, which is a common problem similarly to the embodiments so far. Moreover, there are disclosed a method and a configuration using a gas for promoting ionization that solve a problem in that the ionization needle diameter is small and the sample is apt to be clogged, which is the problem of PTL 1, and solve a problem in that it is only enabled to perform nano-spray ionization with a small flow velocity of liquid sample, and that also cope with an increased flow rate of the flow velocity of liquid sample. Furthermore, there are disclosed a method and a configuration that solve a problem in that ionization becomes unstable, which is the problem of PTL 2. In addition, there are disclosed a method and a configuration that solve a problem of a carry-over taken place by inserting the ionization needle into a spray tube after the sample is attached, which is the problem of PTL 3. There are disclosed methods that can solve the problems simultaneously.

Figure 33:
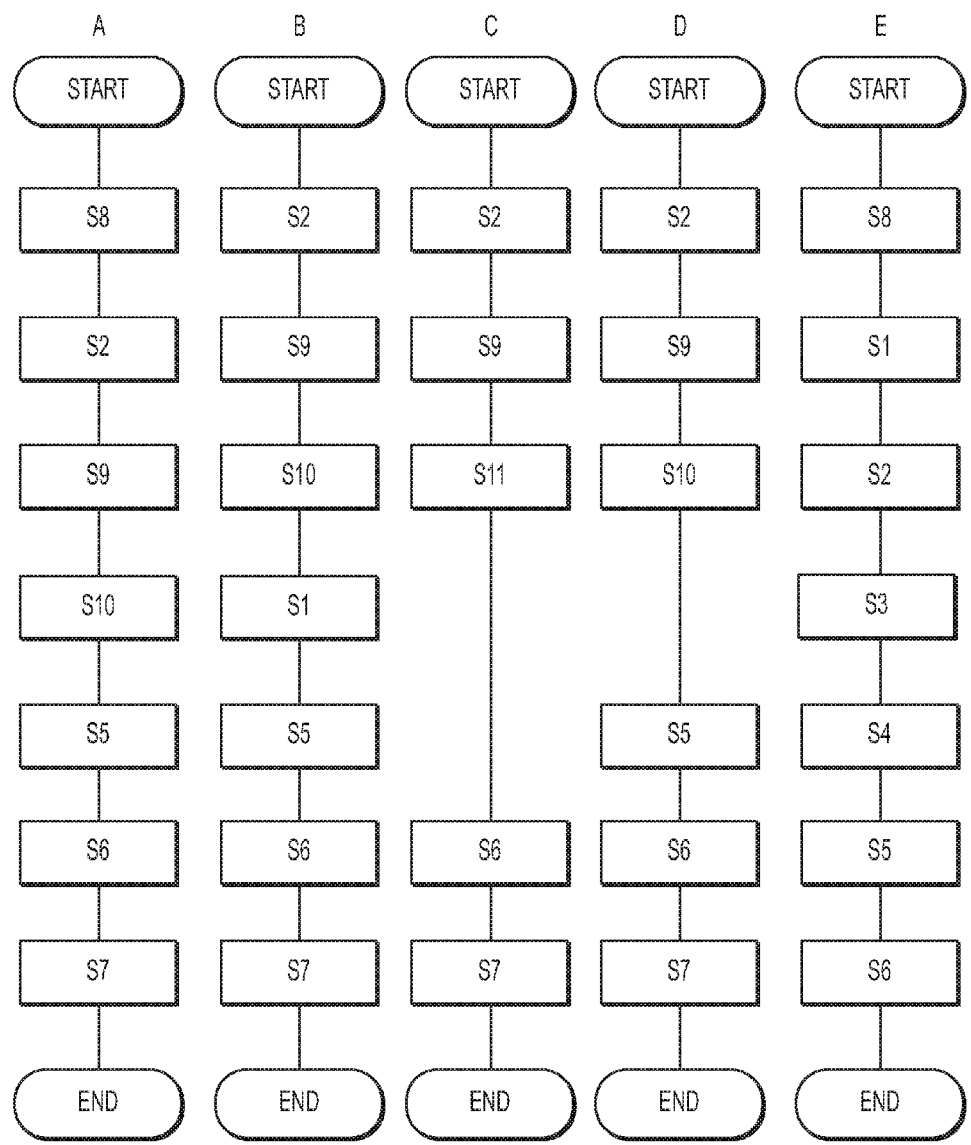
FIGS. 33A to 33E are diagrams of other exemplary flowcharts according to an embodiment.
Figure 34:
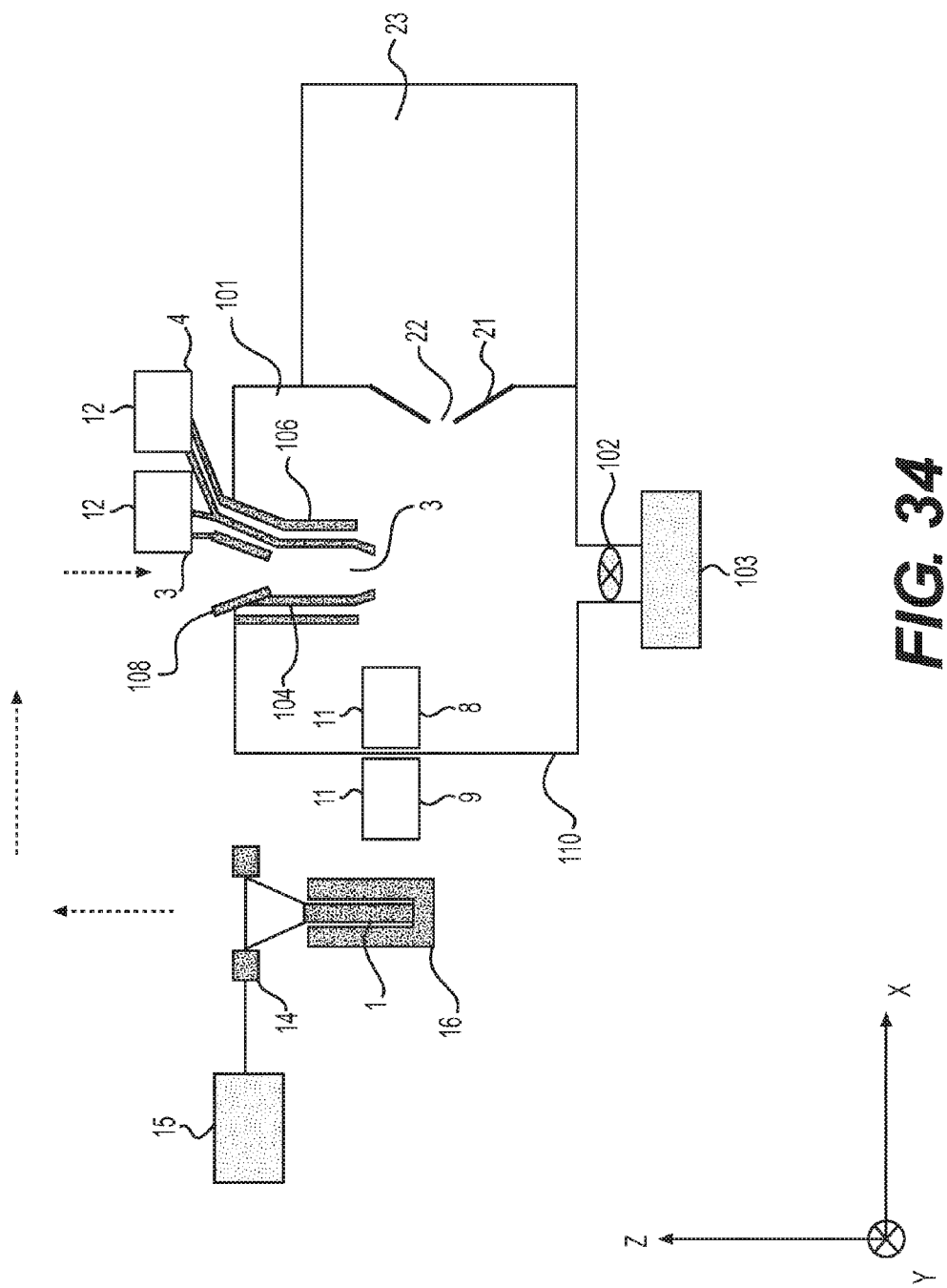
FIG. 34 is a diagram of an example that an ionization needle is moved to an ionization position.

The embodiment discloses a method in which the pressure difference is used to control the flow velocity of liquid sample of a sample solution. The advantage of the present disclosure is in that the flow velocity of liquid sample is controllable more highly accurately by controlling the pressure than in the control methods according to gravity so far. Moreover, the outer wall of the metal capillary 3 of the ionization needle 1 is not contaminated because the outer wall does not contact the liquid sample, and as a result, the contamination of the inside of a nebulizer gas tube 104 contacting the outer wall of the metal capillary 3 can be greatly reduced. In the foregoing embodiments, the method is the sample supplying method according to gravity and is a passive method that does not control the velocity of sample supplying positively. However, in the embodiment, an active method is disclosed in which the velocity of sample supplying is controllable. The method is a method in which the ionization needle 1 is placed on a stage 108 of an ionization chamber 101, and then the liquid sample 10 is supplied from the upper part to the sample container 2 for ionization. The configurations of the components are illustrated in FIG. 34. A method will be described in which the flow velocity of liquid sample is controlled using a difference between a pressure of air on the top face side of the liquid sample 10 in the sample container 2 and a pressure of air on the lower face side and sample supplying is controlled. As illustrated in FIG. 33A, the embodiment includes a pressure control step S8, the moving step S2, a voltage application step S9, a sample supplying step S10, the ionization step S5, the discarding step S6, and the cleaning step S7.

The pressure control step S8 is the step of adjusting and setting the pressure of the inside of the ionization chamber 101. The velocity of sample supplying according to the embodiment is controlled by a difference between an atmospheric pressure and a pressure of the ionization chamber. In order to make the velocity of sample supplying constant, it is necessary to control the pressure of the inside of the ionization chamber and to make the pressure difference constant. The detail will be described later.

The moving step S2 is the step of moving the ionization needle 1 to the ionization position in FIG. 34. A plurality of the ionization needles 1 is arranged and disposed in the needle storage unit 16. The arm 14 that is driven by the transport drive unit 15 is joined to the ionization needle 1, and the ionization needle 1 is moved to a fixing stage 108 of the ionization needle, which is the ionization position. The ionization needle is first moved upwardly from the storage unit 16 (in the positive Z-axis direction), moved horizontally above the stage 108 (in the positive Z-axis direction), and finally moved downwardly (in the negative Z-axis direction). The ionization needle 1 is inserted into the nebulizer gas tube 104 of the ionization chamber 101, and fixed to the stage 108.

Figure 35:
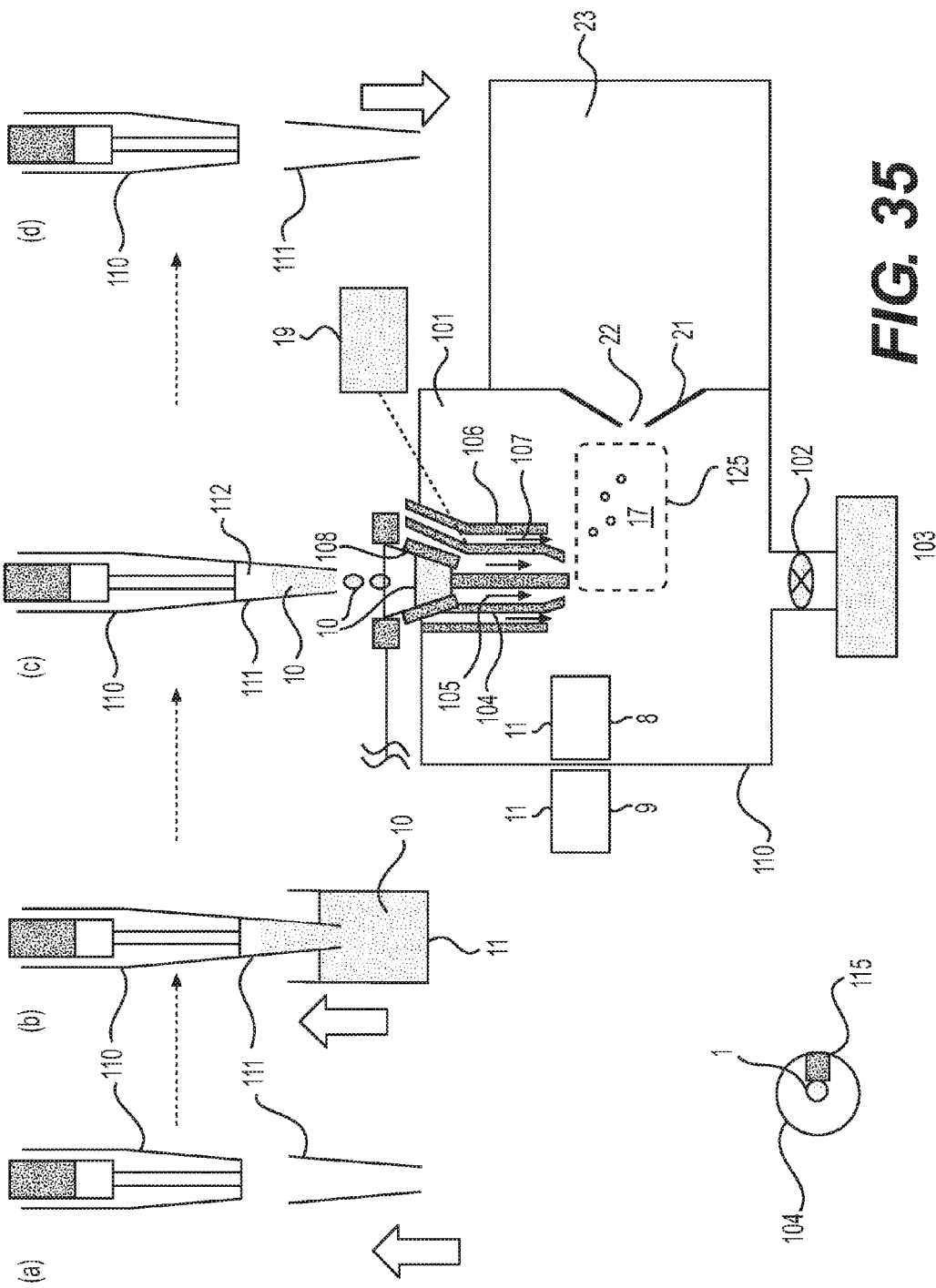
FIG. 35 is a diagram of an example that a voltage is applied to an ionization needle.

The voltage application step S9 is the step of applying a voltage to the ionization needle 1 for ionization (electrostatic spraying). The step and the configuration are illustrated in FIG. 35. Since sample supplying is immediately started by gravity or the pressure difference when the liquid sample 10 is supplied to the sample container 2, it is desirable to apply a voltage to the ionization needle 1 beforehand prior to the supply of the sample. The voltage is applied using the high voltage power supply 19. The high voltage power supply 19 is electrically connected to the nebulizer gas tube 104, and a high voltage is applied to the nebulizer gas tube beforehand. A contact terminal 115 is attached to the inside of the nebulizer tube, in the structure in which when the ionization needle 1 is inserted, the contact terminal 115 contacts the metal capillary 3. Thus, a voltage is applied to the metal capillary 3 of the ionization needle 1 through the contact terminal 115. Generally, a voltage of about a few kV is applied for electrospray ionization. Alternatively, such a method may be possible in which the ionization needle 1 is placed on the stage 108 and then a voltage is applied from the power supply. In this method, it is possible to prevent danger such as discharging electricity in moving the ionization needle 1 and to securely control the apparatus.

The sample supplying step S10 is the step of supplying the liquid sample 10 to the sample container 2 of the ionization needle 1. The pipetter is used to supply the liquid sample 10 to the wide opening side of the sample container 2 (on the upper part in the drawing). The sample is supplied using the pipetter according to the following procedure. (a) A disposable chip 111 is attached to a pipetter 110. (b) A certain amount of the liquid sample 10 contained in the pot 11 is sucked to the chip 111 using the pipetter 110. Typically, the amount ranges from about a few 100 nL to a few 100 µL (c) The chip 111 and the pipetter 110 containing the sample are moved above the ionization needle 1, and the liquid sample 10 is supplied to the sample container 2 using the pipetter 110. (d) After the supply of the sample, the chip 111 is discarded. Measurements can be repeated by repeating the operation.

The ionization step S5 is the step in which electrostatic spraying (spraying) is performed by supplying the liquid sample in the state in which a voltage is applied to the metal capillary 3 of the ionization needle 1. In other words, sample supplying is started simultaneously when the sample is supplied using the chip 111, that is, when ionization is started. A nebulizer gas 105 flows into the nebulizer gas tube 104, and promotes desolvation for ionization. A hot auxiliary gas 107 flows into an auxiliary gas tube 106 provided on the outer side of the nebulizer gas tube 104, and promotes the vaporization of the liquid. It is preferable to promote vaporization when the auxiliary gas is heated at a temperature of a few 100° C. Ionized ions 17 in an ionization region 125 enter the mass spectrometer, which is the detecting unit 23, for analysis. Upon finishing sample supplying, ionization is finished, that is, ionization is finished as the liquid sample 10 is gone from the sample container 2. Moreover, it is also possible that sample supplying is stopped in the midway point by putting a lid (a plug) on the wide opening of the upper part of the sample container 2 even though the liquid sample is left. It is desirable to fix the ionization needle 1 to the stage 108 using the arm 14 or the like in the ionization step S5. The ionization needle 1 is fixed, so that it is possible to perform stable electrostatic spraying without moving or displacing the ion needle 1 caused by a pressure difference, an air current, or the like.

The discarding step S6 is the step of discarding the used ionization needle 1. The ionization needle 1 whose measurement is finished is carried to a foreign particle bin 113 using the arm 14 that is driven by the transport drive unit 15, and is discarded.

The cleaning step S7 is the step of cleaning the nebulizer gas tube. In the discarding step S6, it is likely that the liquid sample remaining in the inside of the ionization needle 1 is attached to the inner wall of the nebulizer tube 104 and contaminates the inner wall when the ionization needle 1 used in measurement is extracted out of the nebulizer gas tube. As a result, a problem arises in that a carry-over is taken place in the subsequent measurement and the measurement accuracy is degraded. Therefore, it is necessary to clean the nebulizer gas tube for individual measurements or on a regular basis. The cleaning method is in which the ionization needle 1 is removed after measurement and the inside of the nebulizer gas tube 104 is cleaned by dripping a cleaning fluid from the upper part of the nebulizer gas tube 104 using a pipetter 116 containing a cleaning fluid 117. Generally, the cleaning fluid in an amount ranging from a few 10 µL to a few 10 mL is used for cleaning for about a few times. The cleaning tool is described in the example using the pipetter. However, the tool may be a syringe or other substitutes that can issue a cleaning solution. It is desirable to perform the cleaning step every time for individual measurements. However, it may be fine that cleaning is performed for once a few measurements as long as the measurements accept contamination. Moreover, the present invention is feasible when the cleaning step is not performed.

In the following, a control method for the velocity of sample supplying unique to the embodiment will be described.

In the following, the control method for the flow velocity of liquid sample will be described. The pressure is controlled for controlling the flow velocity. The pressure control step S8 will be described with reference to FIG. 34. The ionization chamber 101 is followed by a wall 100 for preventing the sample solution from scattering as illustrated in the drawing, in the state in which a gas can communicate between the inside of the ionization chamber and the outside (at an atmospheric pressure) only through the stage 108 and the nebulizer tube 104. Therefore, when the ionization needle 1 containing the liquid sample 10 is placed in the ionization chamber 101, the inside of the ionization chamber is blocked from the outside. Although the outside of the ionization chamber is at an atmospheric pressure, the inside of the ionization chamber is hermetically sealed. The pressure of the secret inside of the ionization chamber is increased with a nebulizer gas or an auxiliary gas, whereas the pressure of the inside of the ionization chamber is reduced by a pump provided on the mass spectrometer. Since the nebulizer gas or the auxiliary gas is a gas flowmeter, gas flow rate controllers 123 and 124 are used. Typically, since the pressure of the inside of the ionization chamber is increased with the nebulizer gas (1 L/min) or the auxiliary gas (4 L/min) and the pressure is reduced in the mass spectrometer (−1 L/min), the pressure of the inside of the ionization chamber is increased at about 4 L/min. It can be thought that in this state, it is not enabled that the liquid sample is dropped and the liquid is supplied only using gravity described in the foregoing embodiments for the liquid sample supplied to the ionization needle 1. Moreover, it can also be thought that such a problem arises in that the liquid sample 10 is issued to the upper part upon placing the ionization needle 1. Therefore, it is necessary to provide a method for reducing the pressure of the inside of the ionization chamber. Furthermore, in order to supply the liquid into the ionization chamber, it is necessary to reduce the pressure of the inside of the ionization chamber more than the pressure of the outside of the ionization chamber.

Here, a problem is the pressure fluctuation in the outside of the ionization chamber (at an atmospheric pressure). The atmospheric pressure fluctuates in a range of a pressure of 90 to 110 kPa (a fluctuation range of a pressure of 20 kPa) depending on the environment and days. On this account, even though the pressure of the inside of the ionization chamber is controlled constant, the pressure difference fluctuates day by day due to a change in the pressure of the atmospheric pressure, so that the velocity of sample supplying also fluctuates day by day. In order to solve the problem and to make the velocity of sample supplying constant, it is necessary to make the pressure difference between the inside of the ionization chamber and the outside (at an atmospheric pressure) constant. Therefore, it is necessary to change the pressure of the inside of the ionization chamber according to a change in the atmospheric pressure. In the embodiment, in order to supply the liquid at a constant velocity of sample supplying all the time for ionization, a method is disclosed in which the pressure difference from the outside (at an atmospheric pressure) is controlled by controlling the pressure of the inside of the ionization chamber. For a mechanism that adjusts the pressure of the inside of the ionization chamber, a pump 103 and a valve 102 are provided.

It is estimated that it is necessary to control the pressure at what degree of accuracy in order to make the velocity of sample supplying constant. The pressure difference between the top face and the lower face of a liquid is estimated when the liquid exists at a height of about 5 cm in the inside of the tube of the ionization needle 1 at an atmospheric pressure (to 100 kPa).

$$100 \text{ kPa} \times \frac{5 \text{ cm}}{10 \text{ m}} = 0.5 \text{ kPa} \quad \text{(Equation 1)}$$

A water column of 5 cm has a pressure difference of a pressure of 0.5 kPa by Equation 1 above, and the liquid is started to flow downwardly by the pressure difference. In order to keep a pressure difference of a pressure of about 0.5 kPa constant all the time, it is necessary to control the pressure difference constant in the accuracy at a pressure of at least 0.1 kPa (about 1/1,000 of the atmospheric pressure) or less. On the other hand, it is the fluctuation of the atmospheric pressure that has the greatest influence in the factors of pressure fluctuation, which are factors to vary the velocity of sample supplying. In order to solve the problem, it is necessary that the pressure of the inside of the ionization chamber be controlled once to a few times everyday to make the pressure difference constant and that the flow velocity of liquid sample be controlled constant.

For a method for controlling the pressure of the inside of the ionization chamber, the pump 103 and the valve 102 are used. Moreover, pressure sensors 118 and 119 that measure a pressure are provided in the inside and the outside of the ionization chamber, and pressures are monitored. The pressure of the inside of the ionization chamber is adjusted and controlled in such a manner that two pressure differences measured by the pressure sensors are made constant. For the control method, such a method may be fine that a human checks the pressure differences on a regular basis to manually control the pump 103 and the valve 102. However, it is desirable to perform automatic control by a computer. For a method for changing the pressure of the inside of the ionization chamber, such a method is used in which the discharge velocity of the pump is changed, or the effective discharge velocity is changed using the valve.

For another method for changing the pressure of the inside of the ionization chamber, it is also possible to use an exhaust fan, a flowmeter, or the like. Moreover, it may be fine to use other known methods for reducing a pressure.

For a method for monitoring a pressure, there may be a method using a differential pressure gauge. In the embodiment, the object is to make the velocity of sample supplying constant, so that it is desirable to provide a method for monitoring the velocity of sample supplying on a regular basis by controlling the pressure of the inside of the ionization chamber using a differential pressure gauge in such a manner that the pressure difference is made constant. One method is a method in which the liquid level is detected using a liquid level sensor such as an ultrasonic wave and a laser, and positional information about the liquid top face is checked. It is possible that the liquid amount consumed is calculated from the positional information about the top face and the elapsed time and the flow velocity of liquid sample of the liquid is calculated. As a result of monitoring, in the case where the velocity of sample supplying is displaced from the specified value, it is also possible to again adjust the pressure of the inside of the ionization chamber. For the frequency of controlling the pressure, the pressure may be controlled every time when the remaining amount of the liquid is changed in measurement, or every time when a measurement sample is changed. Since the pressure fluctuation of the atmospheric pressure in a day is not great so much, such a method may be possible in which the pressure is controlled once or a few times a day.

For another method for monitoring the flow velocity of liquid sample, there is a method in which the weight of the liquid sample 10 is measured to calculate the flow velocity of liquid sample and the flow velocity of liquid sample is controlled. It is also possible that a weight measurement function is provided to the stage 108, the weight of the liquid sample is measured all the time, and the velocity of sample supplying is calculated. In addition to this, it is also possible to calculate the velocity of sample supplying according to a known method for detecting the liquid level or for measuring the weight of the liquid.

In the embodiment, the discarding step is provided. However, it is also possible to reuse the ionization needle 1. At this time, the discarding step is changed to the cleaning step. In order to clean and reuse the ionization needle 1, the ionization needle 1 is moved to the cleaning position. It is fine that the cleaning method is the same as the method described in the foregoing embodiments.

Figure 36:
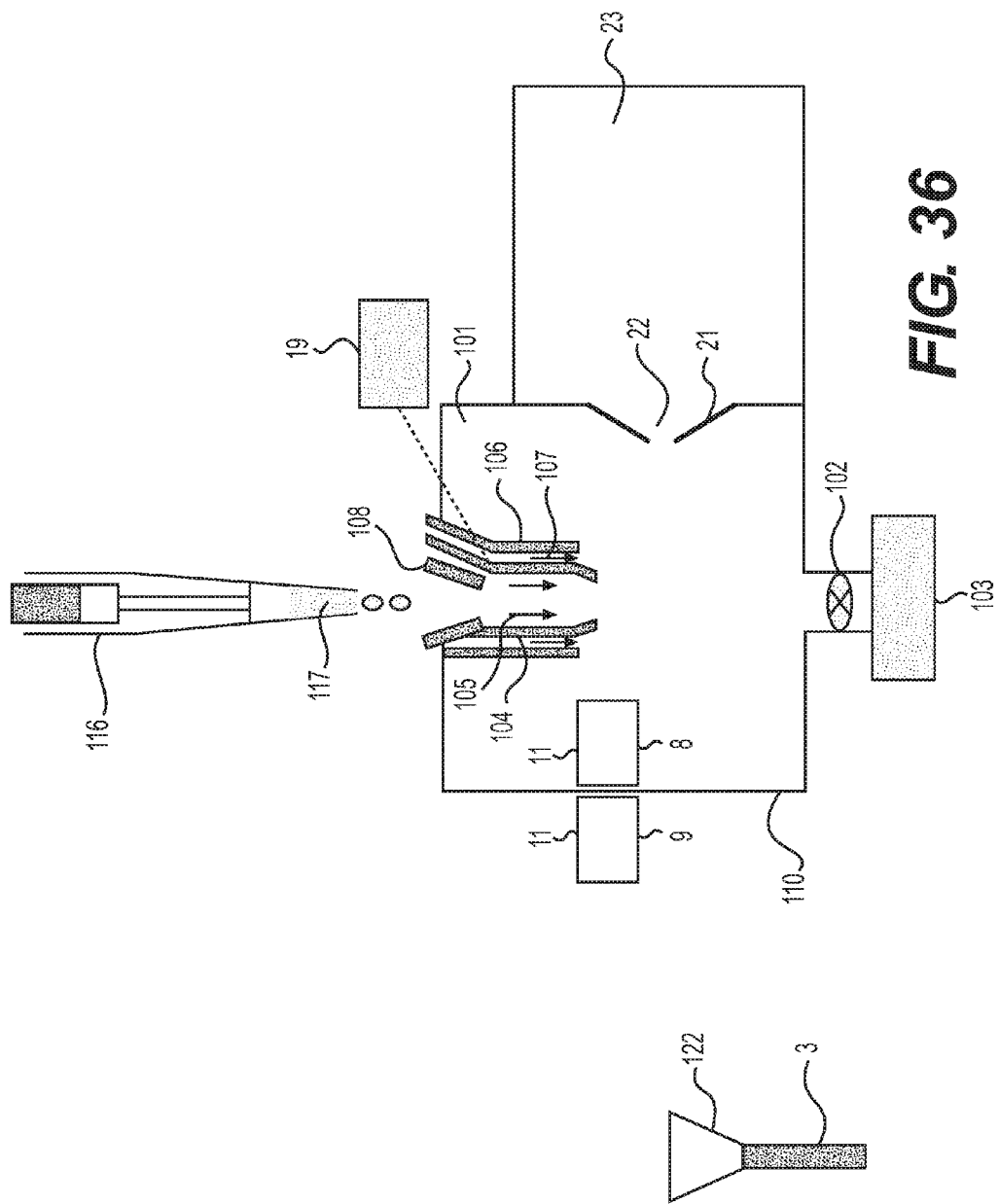
FIG. 36 is a diagram of an example that a voltage is applied to a metal capillary of an ionization needle.

The method for applying a voltage to the metal capillary 3 of the ionization needle 1 may be other methods. One method is in which as illustrated in FIG. 36, the outer wall of the sample container 2 is plated with a conductive material 122 such as a metal, and electrically conducted to the metal capillary 3. A voltage is applied from the high voltage power supply 19 to the stage 108 made of an electric conductor, voltage is also applied to the conductive material 122 of the ionization needle 1 placed on the stage 108, and a voltage is applied to the conducting metal capillary 3 for spraying.

Generally, the pressure of the outside of the ionization chamber is a pressure of about 100 kPa, which is an atmospheric pressure, whereas the pressure of the inside of the ionization chamber can be used at a pressure of 1 kPa to 100 kPa, for example. The lower limit of the pressure is determined according to the inner diameter of the needle depending on how long the liquid is supplied when both of the liquid samples are determined. Moreover, such a method may be possible in which the pressure difference is made zero, that is, the pressure is controlled to be the same between the inside and the outside of the ionization chamber. In this case, the method is a method according to drop sample supplying by gravity, not sample supplying by the pressure difference.

Eleventh Embodiment

Figure 37:
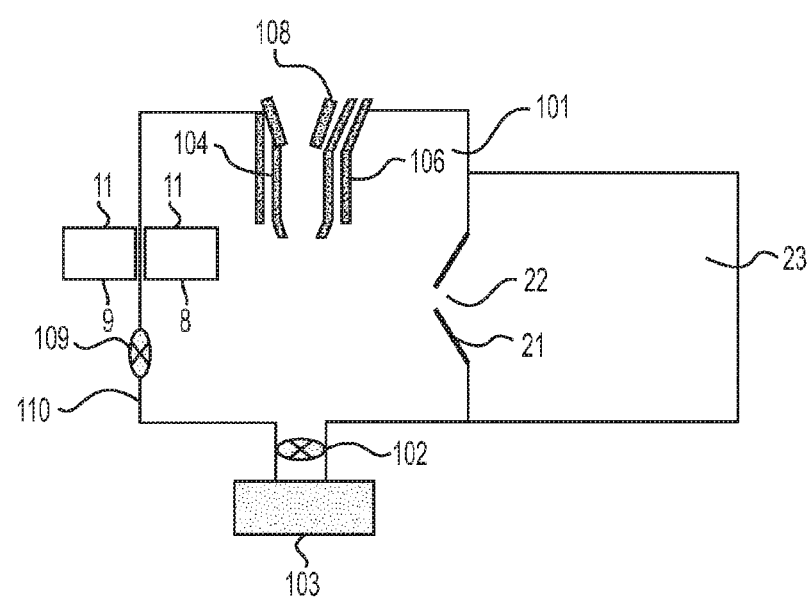
FIG. 37 is a diagram of examples of the wall and valve of an ionization chamber.

Another embodiment will be described. The steps and configurations according to the embodiment are almost the same as those of the tenth embodiment. In the following, the configuration and the pressure control step, which are different from the tenth embodiment, will be described. The embodiment is performed in the configuration as illustrated in FIG. 37. The difference from the tenth embodiment is in that a valve 109 is provided on the wall 100 of the ionization chamber 101. The spaces in the inside and the outside of the ionization chamber are connected to each other through the hole of the valve to adjust the conductance between the two spaces in the inside and the outside of the ionization chamber. When the valve 109 is opened, a gas flows from the space at a high pressure to the space at a low pressure, and the pressure difference between the outside and the inside of the ionization chamber becomes small. The valve 109 is thus provided, so that it is possible to reduce the pressure difference between the inside and the outside of the ionization chamber or to make the pressure difference small or constant. As a result, a merit is obtained that the range controlled by the valve 102 or the pump 103 is narrowed or eliminated. It may be fine that the diameter of a hole formed in the valve 109 ranges from about 0.1 mm to about a few 100 mm. The conductance can be adjusted by opening and closing the valve, and the pressure difference can be adjusted.

Twelfth Embodiment

For another embodiment, a method will be described in which a liquid is supplied using a syringe and a sample supplying pump. The advantage of the embodiment is in that a liquid can be supplied at a constant, stable flow velocity of liquid sample more than in sample supplying using a sample supplying pump. As illustrated in FIG. 33B, the embodiment includes the moving step S2, the voltage application step S9, the sample supplying step S10, the joining step S1, the ionization step S5, the discarding step S6, and the cleaning step S7. Only the joining step S1 and the ionization step S5 will be described, which are different from the tenth embodiment. The other steps are the same as the tenth embodiment.

Figure 38:
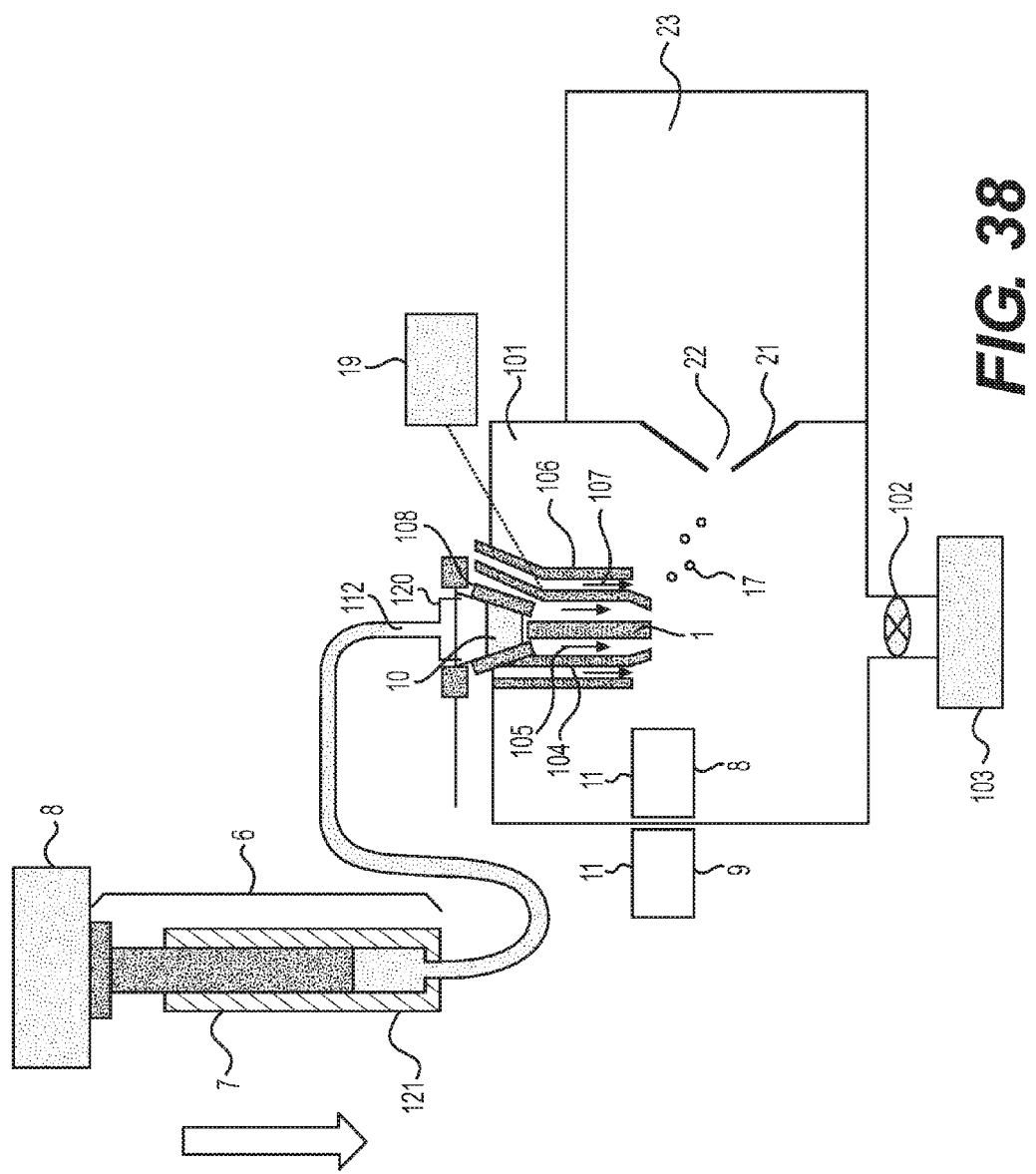
FIG. 38 is a diagram of an example of joining a tube to an ionization needle for sample supplying.

The joining step S1 is the step of joining a tube 114 for sample supplying to the ionization needle 1. As illustrated in FIG. 38, a tube 120 is connected to the syringe 6, and the insides of the tube 120 and the syringe 6 are almost filled with a liquid 121. The tube 120 is joined to the sample container 2 of the ionization needle 1 as illustrated in the drawing. At this time, an air layer 112 is provided beforehand so as not to allow the liquid sample 10 to contact the tube 120 or the liquid 121. Thus, it is possible to prevent the tube 120 or the liquid 121 from being contaminated and to reduce a carry-over in measurement.

In this method, it can be thought that when the volume of the air layer 112 is great, it is difficult to accurately apply a pressure from the syringe 6 to the liquid sample 10 at the tip end due to the expansion or compression of the air layer 112 even though the syringe 6 is pressed using the syringe pump 8, so that it is not enabled to press the liquid at a constant velocity, and as a result, the velocity of sample supplying becomes unstable. Therefore, it is desirable to provide the air layer 112 having a tiny volume to the extent that the liquid sample 10 is not mixed with the liquid 113. In other words, it is desirable to fill the liquid 113 in a greater amount as much as possible. The liquid 113 may be water, an organic solvent, a solvent for the sample, or the like.

The ionization step S5 is the step in which the liquid is supplied by pressing the syringe 6 using the syringe pump 8 and spray is started for ionization. Similarly to the method using a previously existing sample supplying pump, it is possible to supply the liquid at a stable flow velocity by pressing the piston 7 of the syringe 6 at a pre-specified velocity of sample supplying.

Moreover, for another method, such a method may be possible in which the sample is supplied from the upper part using the pipetter, the syringe 6 is then connected, a pressure is applied to the syringe 6 as the syringe is used for a sample supplying syringe, and a liquid is supplied as in the tenth embodiment. According to this method, it is possible to stably supply a liquid at a determined velocity of sample supplying.

Furthermore, for still another method, such a method may be possible in which two syringes, a sample sucking syringe and a sample supplying syringe, are prepared. It is possible to improve the throughput of analysis by sharing the roles. Also in these methods placed, it is desirable to provide the air layer 112 having a tiny volume to the extent that the liquid sample 10 is not mixed with the liquid 113. In other words, it is desirable to fill the liquid 113 in a greater amount as much as possible.

Thirteenth Embodiment

Figure 39:
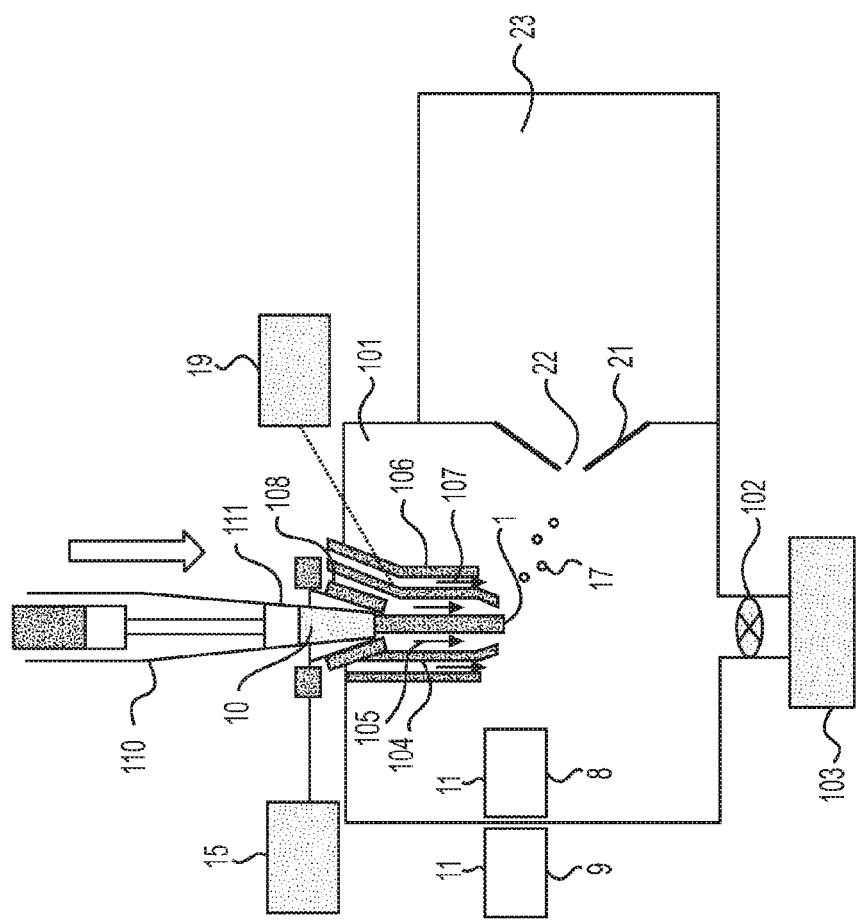
FIG. 39 is a diagram of an example of sample supplying using a pipetter.

For another embodiment, a method will be described with reference to FIG. 39 in which a pipetter is used to supply a liquid as well as to supply the liquid. As illustrated in FIG. 33C, the embodiment includes the moving step S2, the voltage application S9, a sample supply and ionization step S11, the discarding step S6, and the cleaning step S7, and the steps are the same as those in the twelfth embodiment except the sample supply and ionization step S11. Only the sample supply and ionization step S11 will be described which is the step different from the twelfth embodiment.

The sample supply and ionization step S11 is the step of supplying a sample to the ionization needle 1. However, ionization is started simultaneously together with the supply. Similarly to the tenth embodiment, the ionization needle 1 is inserted into the ionization chamber 101, and placed on the stage 108. The chip 111 is attached to the pipetter 110, and the pipetter serves to move the liquid sample 10 from the pot 11 into the ionization needle 1. The pipetter 110 sucks a certain amount of the liquid sample 10 into the chip 111. After that, the pipetter 110 is moved above the ionization needle 1 in the ionization chamber 101, and the ionization needle 1 is intimately joined to the chip 111 so as not to leak the liquid. In the joined state, the pipetter is pressed at a constant velocity, and the liquid sample is stably supplied at a constant flow velocity. The pipetter can supply the liquid at a constant velocity by providing a syringe pump or the like.

Fourteenth Embodiment

Figure 40:
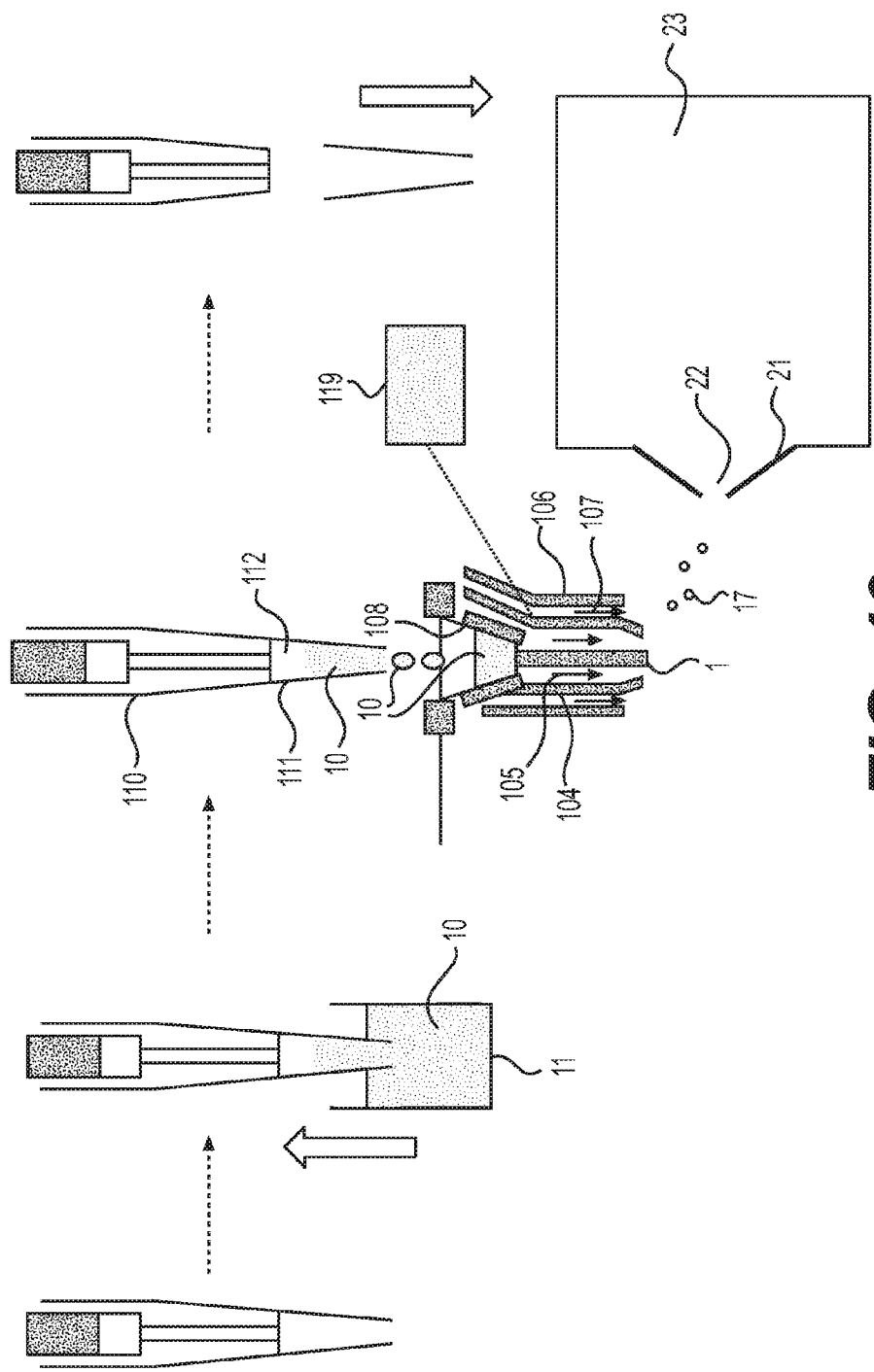
FIG. 40 is a diagram of an example that an ionization chamber is not provided.
Figure 41:
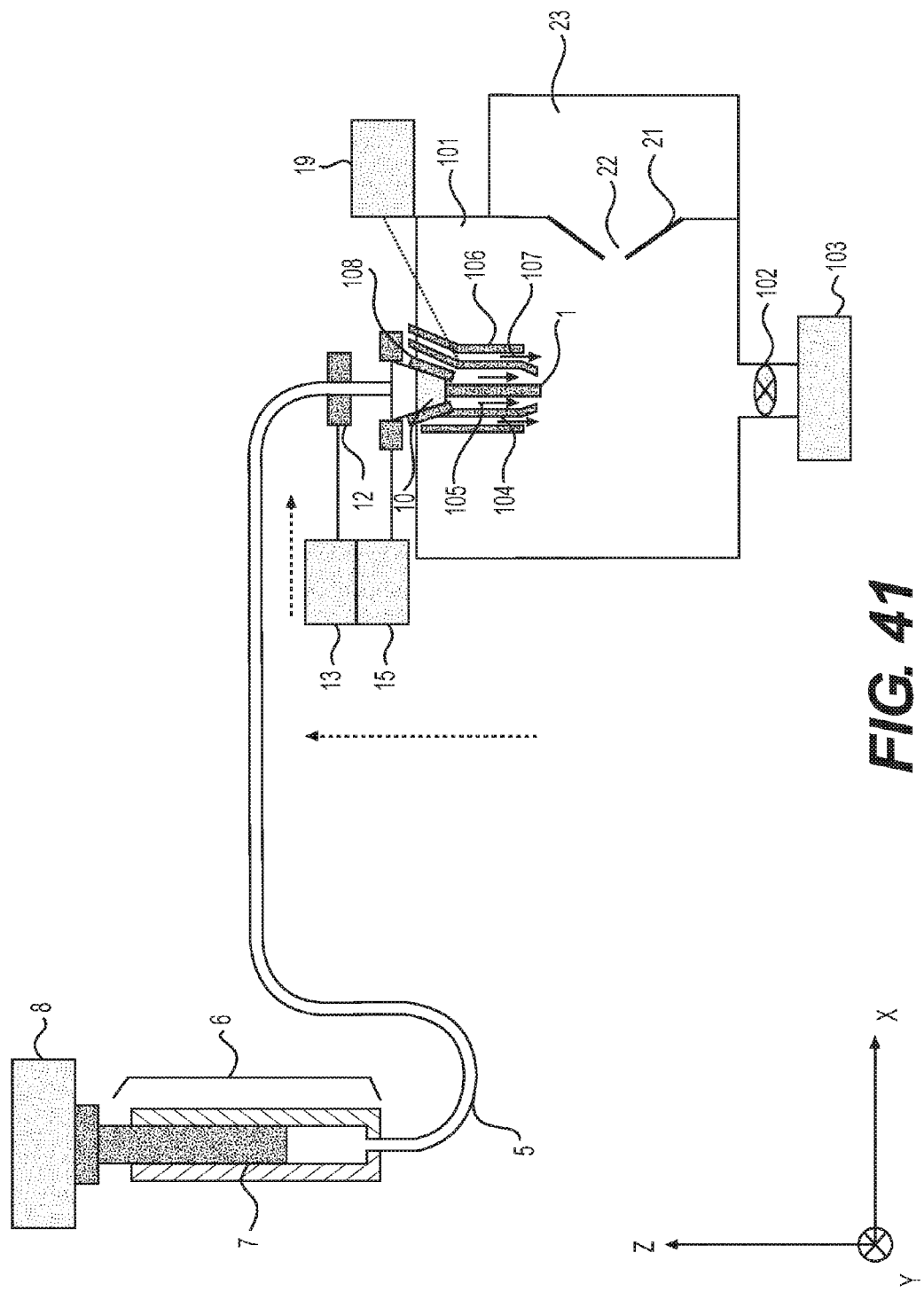
FIG. 41 is a diagram of an example of joining a tube to an ionization needle for sample supplying.

For another embodiment, an embodiment will be described with reference to FIG. 40 in a configuration in which the ionization chamber is not provided in the tenth embodiment.

As illustrated in FIG. 33D, the embodiment includes the moving step S2, the voltage application step S9, the sample supplying step S10, the ionization step S5, the discarding step S6, and the cleaning step S7. Since the ionization chamber is not provided, the pressure difference is eliminated, and pressure control is unnecessary. On this account, the steps are the same as the steps according to the tenth embodiment except that the pressure control step S8 is not provided. In a sample supplying method for a sample solution according to the embodiment, a liquid is supplied by gravity (the pressure difference between liquid levels) similarly to the first embodiment. The difference from the first embodiment is a method for supplying the liquid sample 10 to the ionization needle 1. Similarly to the tenth embodiment, the liquid sample 10 is sucked into the chip 111 using the pipetter 110, and introduced into the upper part of the ionization needle 1. Upon introducing the sample, sample supplying is started, and ionization is performed.

Fifteenth Embodiment

For another embodiment, an exemplary application of the tenth embodiment will be described. Although the configuration is the same as the configuration according to the tenth embodiment, a method for supplying the sample to the ionization needle 1 is different. The sample is supplied to the ionization needle by sucking the sample from the tip end of the ionization needle. The steps of the measurement operation according to the embodiment include the pressure control step S8, the joining step S1, the moving step S2, the sucking step S3, the moving step S4, the ionization step S5, and the discarding step S6 (FIG. 33E).

The pressure control step S8 is the step of controlling the pressure of the ionization chamber. As described in the tenth embodiment, the valve 102 or the pump 103 is controlled so as to achieve a predetermined flow velocity of liquid sample beforehand, and the pressure of the inside of the ionization chamber is adjusted.

The methods for performing the joining step S1, the moving step S2, the sucking step S3, and the moving step S4 are the same as the first embodiment.

Figure 42:
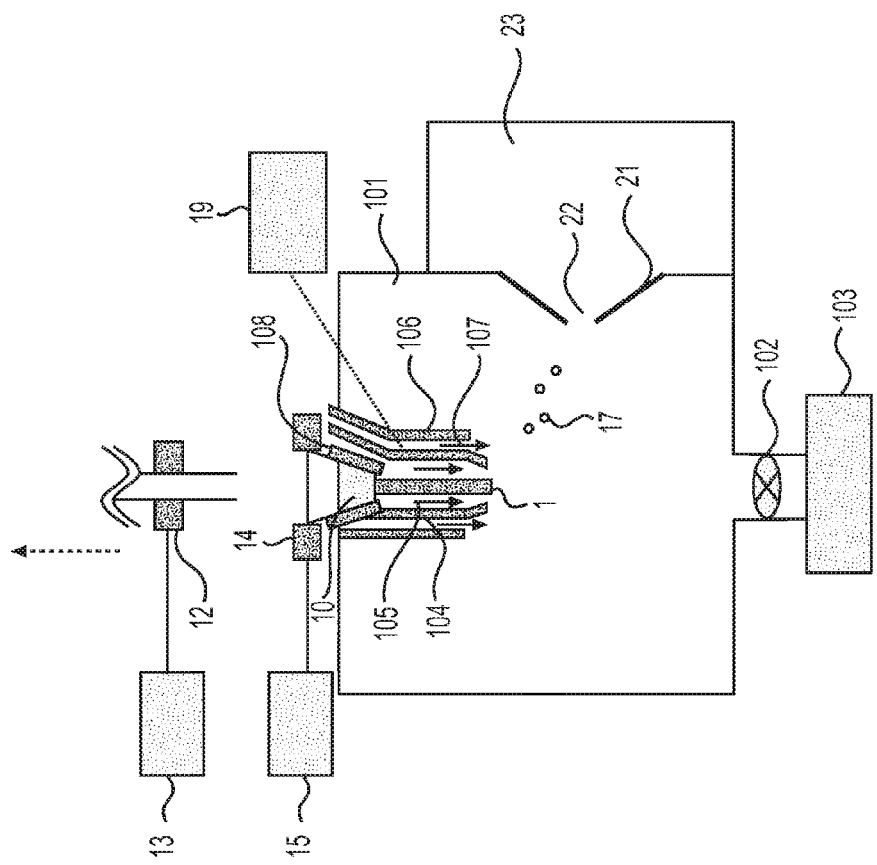
FIG. 42 is a diagram of an example that a tube is detached from an ionization needle.

The ionization step S5 is the step in which a voltage is applied to the metal capillary 3 of the ionization needle 1, the liquid sample is supplied, and electrostatic spraying (spraying) is performed. Sample supplying is started together with the application of a voltage and the supply of the sample, and ionization is started. The supplying of the liquid sample for ionization is started by detaching the tube 5 from the ionization needle 1. These are illustrated in FIG. 42. Similarly to the tenth embodiment, the liquid is supplied using the pressure difference.

The discarding step S6 is the step of discarding the used ionization needle 1. The ionization needle 1 whose measurement is finished is discarded into the foreign particle bin using the arm 14 that is controlled by the transport drive unit 15.

It may be possible to replace the discarding step S6 by the cleaning step as described in the tenth embodiment.

Sixteenth Embodiment

For another embodiment, an exemplary application of the first embodiment will be described. The embodiment is a method in which an ionization chamber is further provided on the configuration of the first embodiment and spraying is performed in the inside of the ionization chamber for ionization. The steps of the measurement operation according to the embodiment include the joining step S1, the moving step S2, the sucking step S3, the moving step S4, the ionization step S5, and the discarding step S6, and the steps are the same as the first embodiment as illustrated in FIG. 1A. The configuration and the method are different only in the ionization step S5, and the description will be given with reference to FIG. 43.

Figure 43:
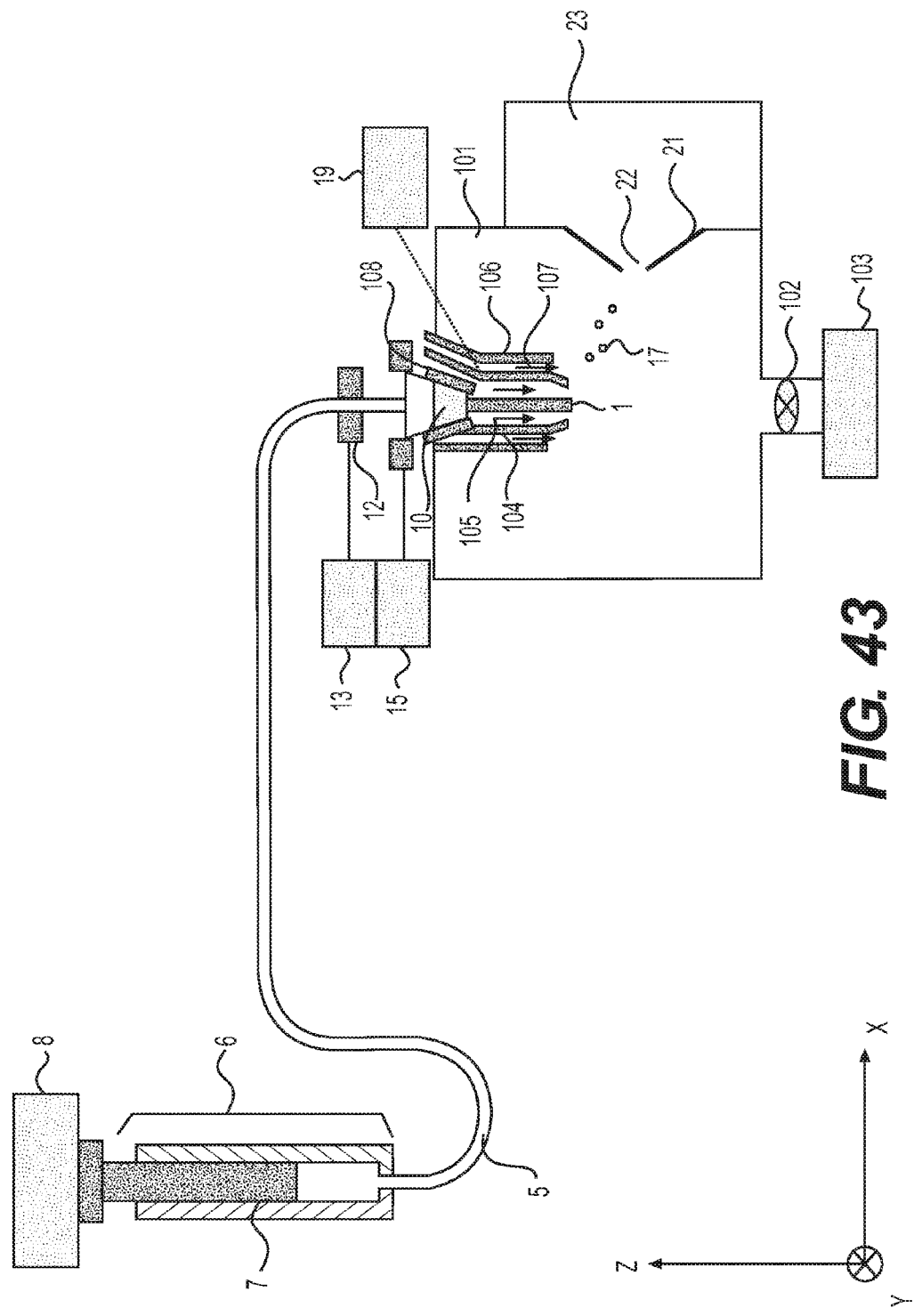
FIG. 43 is a diagram of an example that a pressure is applied using a syringe without detaching a tube.
Figure 44:
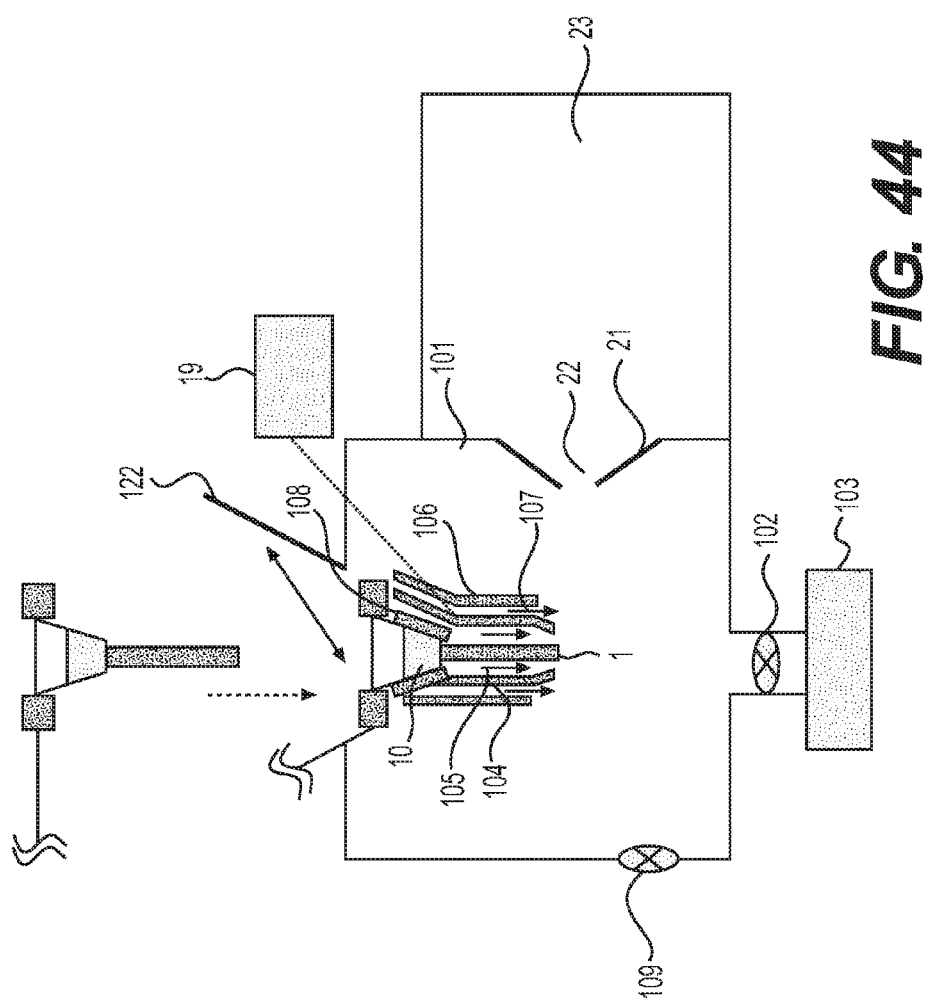
FIG. 44 is a diagram of an example that the pressure of an ionization chamber is controlled.

The ionization step S5 is the step in which a voltage is applied to the metal capillary 3 of the ionization needle 1, the liquid sample is supplied, and electrostatic spraying (spraying) is performed. The difference from the first embodiment is in that as illustrated in FIG. 43, the tube 5 is not detached, a pressure is applied using the syringe 6 and the syringe pump 8 as they are, and the liquid is supplied. The syringe pump 8 is used, so that it is possible to stably supply the liquid at a constant flow velocity all the time.

Seventeenth Embodiment

For another embodiment, exemplary applications of the twelfth, thirteenth, and sixteenth embodiments will be described. In these embodiments, in the case where the ionization unit is not covered with the ionization chamber 101, that is, even in the case of an open system, ionization is feasible. These methods are methods using a sample supplying pump such as a syringe pump and a pipetter for the supplying of the liquid sample, which allow a stable supplying of the liquid sample regardless of the presence or absence of the ionization chamber.

Eighteenth Embodiment

For another embodiment, in the first to ninth embodiments, such a configuration may be possible in which a nebulizer gas or an auxiliary gas is used. The advantage is in that a nebulizer gas or a heated auxiliary gas is flown to a liquid sample, by which desolvation is promoted and the improvement of sensitivity can be expected. However, on the other hand, the nebulizer gas tube is contaminated with the sample, which causes a carry-over. On this account, it is necessary to clean the nebulizer gas tube as described in the tenth embodiment.

Because of the similar reason, after the tenth embodiment, such a configuration may be possible in which a nebulizer gas or an auxiliary gas is not provided. Although a problem arises in that the sensitivity is reduced, a merit is achieved that a carry-over caused by contamination is reduced.

Moreover, the auxiliary gas tube 106 through which the auxiliary gas 107 flows is described as the coaxial tube with the metal capillary 3. However, such a method may be possible in which a flow of a gas is applied to the liquid sample from a different location as in the publicly known techniques.

Nineteenth Embodiment

For another embodiment, an exemplary application of the first embodiment will be described. The embodiment is in a configuration in which an openable and closable door 122 is provided in the configuration according to the tenth embodiment, which is different from the tenth embodiment in that the ionization needle and the sample solution are entirely included in the ionization chamber, so that the pressure difference is not produced between the top face and the lower face of the sample solution. In other words, the embodiment is a method in which the liquid is supplied due to gravity drop in the inside of the ionization chamber. The liquid sample is supplied in the outside of the ionization chamber, and it is possible to use any of the method for supplying the sample from the tip end of the ionization needle 1 as in the first embodiment and the method for supplying the sample from the upper part of the sample container 2 of the ionization needle 1 as in the tenth embodiment. Moreover, another supplying method may be possible. After the sample is supplied to the ionization needle, the door 122 is opened, which is provided on the ionization chamber 101, and the ionization needle 1 is placed on the stage 108 in the inside of the ionization chamber. Since the ionization needle 1 is provided in the inside of the ionization chamber, the atmospheric pressure is the same between the upper part and the lower part of the liquid level. Therefore, the liquid is supplied due to gravity drop similarly to the first embodiment. In addition to this, the detailed method is the same as the first embodiment. The embodiment is also feasible regardless of using or not using a nebulizer gas or an auxiliary gas.

It is noted that the present invention is not limited to the foregoing embodiments, and includes various exemplary modifications. For example, the foregoing embodiments are described in detail for easily understanding the present invention, and are not limited to ones including all the configurations described above. Moreover, a part of the configuration of a certain embodiment can be replaced by the configuration of another embodiment, and the configuration of a certain embodiment can also be added with the configuration of another embodiment. Furthermore, a part of the configuration of the embodiments can be added with, deleted from, and replaced by the configurations of another embodiment.

REFERENCE SIGNS LIST 1 ionization needle
2 sample container
3 metal capillary
4 needle tip end
5 tube
6 syringe
7 syringe piston
8 syringe pump
10 liquid sample
11 sample pot
12 arm
13 transport drive unit
14 arm
15 transport drive unit
16 needle storage unit
17 ion
18 contact terminal
19 high voltage power supply
20 drive unit
21 counter electrode
22 pore
23 detecting unit
25 support
26 fixed point
27 to 28 container holder
31 fixing unit
32 spring
33 contact terminal
34 contact terminal
35 contact terminal
41 sample pot storage unit
42 to 46 position of an analysis sample (pot)
51 to 57 position of an ionization needle
61 cleaning position
62 arm
63 transport drive unit
64 cleaning fluid
65 cleaning pot
66 ultrasonic cleaner
67 high pressure cleaner
68 cleaning tube
69 container
71 arm
72 transport drive unit
73 high voltage power supply
74 support
75 to 76 container holder
77 drive unit
78 support
79 to 80 container holder
81 valve
82 controller
83 lid
84 hole
85 drive unit
86 to 87 container holder
88 drive unit
89 to 90 container holder
91 porous material
92 porous material
93 drive unit
95 metal capillary
96 stage
97 controller
100 wall
101 ionization chamber
102 valve
103 pump
104 nebulizer gas tube
105 gas flow
106 auxiliary gas tube
107 gas flow
108 stage
109 valve
110 pipetter
111 chip
112 air layer
113 foreign particle bin
115 contact terminal
116 pipetter
117 cleaning fluid
118 to 119 pressure sensor
120 tube
121 liquid
122 door
123 to 124 gas controller
125 ionization region

The invention claimed is:
1. An ionization method using an ionization unit having a sample holder configured to hold a sample,
an ionization unit drive unit configured to drive the ionization unit,
a power supply configured to apply a voltage to the ionization unit, and
a sample suction tube,
the method comprising the steps of:
joining the ionization unit to the tube;
sucking the sample from a sample container into a sample holder of the ionization unit to hold the sample;
moving the ionization unit holding the sample to a detecting unit using the ionization unit drive unit; and
separating the ionization unit and the tube and applying a voltage to the ionization unit using the power supply to ionize the sample by electrostatically spraying the sample from the sample holder, wherein the ionization is performed upon opening of one end of the sample holder by the separation of the ionization unit from the tube thereby allowing the sample to drop from the sample holder from another open end of the sample holder due to the force of gravity.

2. The ionization method according to claim 1, further comprising the step of moving the sample container containing the sample to the ionization unit.

3. The ionization method according to claim 1, further comprising the step of moving the ionization unit from the detecting unit to discard the ionization unit using the ionization unit drive unit.

4. The ionization method according to claim 1, wherein:
the ionization unit is an ionization needle including a metal capillary and a sample holding container having a tapered opening; and
in the joining step, the opening of the sample holding container is joined to the tube.

5. The ionization method according to claim 1, wherein in the ionization step, sample supplying is started at the same time when the voltage is applied or after the voltage is applied, and application of the voltage is canceled at the same time when sample supplying is stopped or after sample supplying is stopped.

6. The ionization method according to claim 4, wherein in the ionization step, the tube is detached in a state in which a pressure of the inside of the sample holder of the ionization unit is not reduced.

7. The ionization method according to claim 1, further comprising a flow velocity controller configured to control a velocity of sample supplying of the ionization unit,
wherein in the ionization step, a flow velocity of the sample supplying is controlled using the flow velocity controller.

8. The ionization method according to claim 4, wherein a velocity of sample supplying is controlled by an inner diameter of the metal capillary, or a velocity of sample supplying is controlled by a slope of the metal capillary.

9. The ionization method according to claim 1, further comprising a plurality of the ionization units and a plurality of the sample containers,
wherein the ionization unit and the sample container are transported using a transport unit.

10. The ionization method according to claim 1, wherein the ionization unit comprises a needle or a metallic capillary connected to the sample holder, and the method further comprising a step of washing the ionization unit.

11. The ionization method according to claim 6, wherein the pressure of the inside of the sample holder of the ionization unit is not reduced in the ionization step by a pressure from a pump, a pressure control by a valve, or a horizontally slide of the tube.

12. The ionization method according to claim 7, wherein the ionization unit has a porous material, and the flow of sample supplying is controlled so that the sample passes through the porous material.

13. An ionization apparatus comprising:
an ionization unit having a sample holder configured to hold a sample;
an ionization unit drive unit configured to drive the ionization unit;
a power supply configured to apply a voltage to the ionization unit;
a sample suction tube;
a coupling unit configured to join the ionization unit to the tube;
a sucking unit configured to suck the sample from a sample container into a sample holder of the ionization unit and hold the sample;
a moving unit configured to move the ionization unit holding the sample to a detecting unit using the ionization unit drive unit; and
an ion source unit configured to apply a voltage to the ionization unit using the power supply to ionize the sample by electrostatically spraying the sample from the sample holder after the coupling unit separates the ionization unit and the tube,
wherein the ion source is configured to perform the ionization upon opening of one end of the sample holder by the coupling unit separating the ionization unit from the tube thereby allowing the sample to drop from the sample holder from another open end of the sample holder due to the force of gravity.

14. A mass analysis system comprising: an ionization unit having a sample holder configured to hold a sample;
an ionization unit drive unit configured to drive the ionization unit;
a power supply configured to apply a voltage to the ionization unit;
a sample suction tube;
a coupling unit configured to join the ionization unit to the tube;
sucking unit configured to suck the sample from a sample container into a sample holder of the ionization unit and hold the sample;
a moving unit configured to move the ionization unit holding the sample to a detecting unit using the ionization unit drive unit;
an ion source unit configured to apply a voltage to the ionization unit using the power supply to ionize the sample by electrostatically spraying the sample from the sample holder after the coupling unit separates the ionization unit and the tube; and
a mass analyzing unit configured to analyze the ionized sample,
wherein the ion source is configured to perform the ionization upon opening of one end of the sample holder by the coupling unit separating the ionization unit from the tube thereby allowing the sample to drop from the sample holder from another open end of the sample holder due to the force of gravity.

* * * * *